United States Patent
Cmiljanovic et al.

(10) Patent No.: US 9,556,203 B2
(45) Date of Patent: Jan. 31, 2017

(54) CONFORMATIONALLY RESTRICTED P13K AND MTOR INHIBITORS

(71) Applicants: UNIVERSITAET BASEL, Petersgraben (CH); PIQUR THERAPEUTICS AG, Basel (CH)

(72) Inventors: Vladimir Cmiljanovic, Basel (CH); Paul Hebeisen, Basel (CH); Eileen Jackson, Basel (CH); Florent Beaufils, Bartenheim (FR); Thomas Bohnacker, Basel (CH); Matthias Wymann, Bern (CH)

(73) Assignees: PIQUR THERAPEUTICS AG, Basel (CH); UNIVERSITAET BASEL, Basel (CH)

( * ) Notice: Subject to any disclaimer, the term of this patent is extended or adjusted under 35 U.S.C. 154(b) by 0 days.

(21) Appl. No.: 15/026,431

(22) PCT Filed: Oct. 3, 2014

(86) PCT No.: PCT/EP2014/071227
§ 371 (c)(1),
(2) Date: Mar. 31, 2016

(87) PCT Pub. No.: WO2015/049369
PCT Pub. Date: Apr. 9, 2015

(65) Prior Publication Data
US 2016/0244463 A1    Aug. 25, 2016

(30) Foreign Application Priority Data
Oct. 4, 2013  (EP) ...................................... 13187386

(51) Int. Cl.
C07D 519/00 (2006.01)
C07D 498/14 (2006.01)
C07D 513/14 (2006.01)

(52) U.S. Cl.
CPC ........... C07D 498/14 (2013.01); C07D 513/14 (2013.01); C07D 519/00 (2013.01)

(58) Field of Classification Search
CPC .................................................... C07D 519/00
See application file for complete search history.

(56) References Cited

FOREIGN PATENT DOCUMENTS

WO    WO 2012/167606    12/2012

OTHER PUBLICATIONS

T. Kato et al., 24 Chemical & Pharmaceutical Bulletin, 2461-2469 (1976).*

* cited by examiner

*Primary Examiner* — Alexander R Pagano
(74) *Attorney, Agent, or Firm* — Medler Ferro Woodhouse & Mills PLLC

(57) ABSTRACT

The invention relates to novel phosphoinositide 3-kinase (PI3K) and mammalian target of rapamycin (mTOR) inhibitor compounds of formula (I) and (II), which are conformationally restricted, and for which the meaning of the substituents are listed in the description. Preferred compounds are those wherein X isoxygen, $R_1$ is morpholino and $R_2$ is substituted phenyl or heteroaryl. These compounds are useful, either alone or in combination with further therapeutic agents, for treating disorders mediated by lipid kinases.

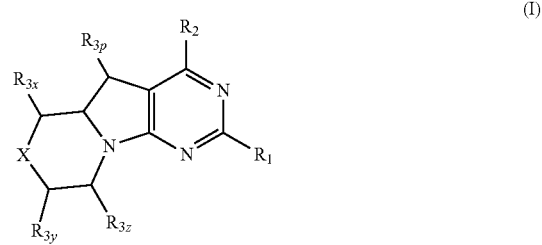

(I)

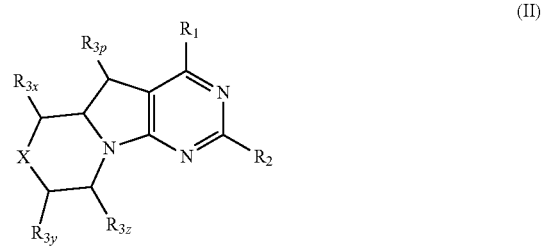

(II)

16 Claims, No Drawings

CONFORMATIONALLY RESTRICTED PI3K AND MTOR INHIBITORS

FIELD OF THE INVENTION

The invention relates to new morpholino-dihydropyrrolopyrimidines and related compounds as therapeutic agents and diagnostic probes useful for modulating cellular activities such as signal transduction, proliferation, differentiation, programmed cell death, migration and cytokine secretion. The compounds of the invention modulate kinase activity, in particular phosphoinositide 3-kinase (PI3K), mammalian target of rapamycin (mTOR), DNA-PK and ATM kinase activity.

BACKGROUND OF THE INVENTION

Protein kinases participate in the signaling events which control the activation, growth, differentiation, survival and migration of cells in response to extracellular mediators or stimuli including growth factors, cytokines or chemokines. In general, these kinases are classified in two groups, those that preferentially phosphorylate tyrosine residues and those that preferentially phosphorylate serine and/or threonine residues. The tyrosine kinases include membrane-spanning growth factor receptors, for example the epidermal growth factor receptor (EGFR) and cytosolic non-receptor kinases including Src family kinases, the Syk family kinases and the Tec family kinases.

Inappropriately high protein kinase activity is involved in many diseases including cancer, metabolic diseases, immunological diseases and inflammatory disorders. This can be caused either directly or indirectly by the failure of control mechanisms due to mutation, overexpression or inappropriate activation of the enzyme.

Protein tyrosine kinases—both receptor tyrosine kinases and non-receptor kinases—are essential for the activation and proliferation of cells of the immune system. Among the earliest detectable events upon immunoreceptor activation in mast cells, T cells and B cells, is the stimulation of non-receptor tyrosine kinases.

Phosphoinositide 3-kinases (PI3Ks) were early on identified as lipid kinases associated with viral oncogens [Whitman et al., Nature 315:239-242 (1985)], and for the last 20 years, the connection between cancer and PI3K has been further substantiated [Wymann et al., Curr. Opin. Cell Biol. 17:141-149 (2005)]. PI3Ks have since been recognized to modulate a wide range of cellular activities, and to be central to the growth and metabolic control. Genetically modified mice targeting the PI3K pathway, and the elucidation of human hereditary disease like Cowden's syndrome, tuberous sclerosis, ataxia telangiectasia, X-linked myotubular myopathy and Charcot-Marie-Tooth neuropathy, have provided further insight in the cellular and systemic role of phosphoinositide signaling. Deregulation of phosphoinositide levels, and in particular the product of class I PI3Ks, PtdIns (3,4,5)P3, is involved in the pathogenesis of cancer, chronic inflammation, allergy, metabolic disease, diabetes and cardiovascular problems.

PI3Ks are a family of enzymes, which phosphorylate the 3'-OH position of the inositol ring of phosphoinositides. They have been divided into three classes on the basis of structural features and in vitro lipid substrate specificity [Marone et al., Biochimica et Biophysica Acta 1784:159-185 (2008)]. Class I PI3Ks form heterodimers, which consist of one of the four closely related approx. 110 kDa catalytic subunits, and an associated regulatory subunit belonging to two distinct families. In vitro they are capable to convert PtdIns to PtdIns-3-P, PtdIns-4-P to PtdIns(3,4)P2, and PtdIns{4,5)P2 to PtdIns(3,4,5)P3, but the in vivo substrate is PtdIns(4,5)P2 [Cantley et at., Science 296:1655-1657 (2002)]. Class I PI3Ks are activated by a large variety of cell-surface receptors, comprising growth factor receptors as well as G protein-coupled receptors.

Class II PI3Ks are capable to phosphorylate PtdIns and PtdIns-4-P in vitro, but their relevant in vivo substrates are still under investigation. This class of large (170-200 kDa) enzymes has three members, all characterized by a C-terminal C2 homology domain. No adaptor molecules for class II PI3Ks have been identified so far. Class III PI3Ks are solely able to phosphorylate PtdIns, and thus generate only PtdIns-3-P. The single member of this class is Vps34, of which the S. cerevisiae Vps34p (vacuolar protein sorting mutant 34 protein) is the prototype, and has been shown to play an essential role in trafficking of newly synthesized proteins from the Golgi to the yeast vacuole, an organelle equivalent to lysosomes in mammals [Schu et al., Science 260:88-91 (1993)].

Phosphoinositide 4-kinases (PI4Ks) phosphorylate the 4'-OH position of the inositol ring of PtdIns, and thereby generate PtdIns-4-P. This lipid can then be further phosphorylated by PtdIns-4-P 5-kinases to generate PtdIns (4,5)P2, which is the main source for phospholipase C and PI3K signaling at the plasma membrane. Four PI4Ks isoforms are known: PI4KIIα and β and PI4KIIIα and β. The PI4KIIIs are most closely related to PI3Ks.

The class of PI3K-related proteins, referred to as class IV PI3Ks, consists of high molecular weight enzymes with a catalytic core similar to PI3Ks and PI4Ks and include the target of rapamycin (mTOR, also known as FRAP), DNA-dependent protein kinase (DNA-PKcs), the ataxia telangiectasia mutated gene product (ATM), ataxia telangiectasia related (ATR), SMG-1 and transformation/transcription domain-associated protein (TRRAP). The first five members are active protein serine-threonine kinases that are involved in cell growth control and genome/transcriptome surveillance [Marone et al., Biochimica et Biophysica Acta 1784: 159-185 (2008)]. DNA-PKcs, ATM, ATR and SMG-1 are involved in DNA-damage responses. The only active kinase not involved in DNA-damage is mTOR, which is regulated by growth factors and nutrient availability, and coordinates protein synthesis, cell growth and proliferation. Target of rapamycin (mTOR) complexes 1 and integrate growth factor signaling (via PI3K/PKB and the Ras/MAPK cascade), energy status (LKB1 and AMPK) and nutrient detection. TOR is positively regulated by PKB/Akt, which phosphorylates the negative regulator TSC2 in the tuberous sclerosis complex (TSC), resulting in activation of the GTPase Rheb and mTOR. In parallel, mTOR stimulates translation of ribosomal proteins and therefore ribosome biogenesis via the activation [Wullschleger et al., Cell 124:471 (2006)]. Rapamycin, and its derivatives RAD001 and CCI-779, bind to FKBP12, and the complex blocks mTOR complex 1 (mTORC1) activity very selectively. Various clinical trials were initiated using rapamycin and derivatives, mostly in patients with tumors displaying elevated PI3K signaling and hyperactive mTOR.

The PI3K pathway is a key signaling transduction cascade controlling the regulation of cell growth, proliferation, survival as well as cell migration. PI3Ks are activated by a wide variety of different stimuli including growth factors, inflammatory mediators, hormones, neurotransmitters, and immunoglobulins and antigens [Wymann et al., Trends Pharmacol. Sci. 24:366-376 (2003)]. The class IA PI3K isoforms PI3Kα, β and δ, are all bound to one of the p85/p55/p50 regulatory subunits, which all harbor two SH2 domains that bind with high affinity to phosphorylated Tyr-X-X-Met motifs. These motifs are present in activated growth factor receptors, their substrates and numerous adaptor proteins. As described above, activation of the PI3K/PKB signaling cascade has a positive effect on cell growth, survival and proliferation. Constitutive up-regulation of PI3K signaling can have a deleterious effect on cells leading to uncontrolled proliferation, enhanced migration and adhesion-independent growth. These events favor not only the formation of malignant tumors, but also the development of inflammatory and autoimmune disease.

SUMMARY OF THE INVENTION

The invention relates to conformationally restricted compounds of formula (I) or (II)

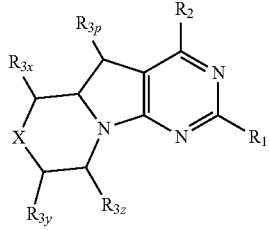
(I)

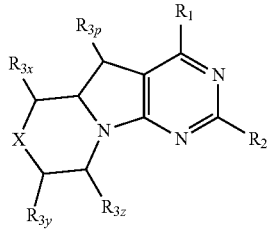
(II)

pharmaceutical compositions comprising these, and their use as therapeutic agents and diagnostic probes.

The invention further relates to the use of these compounds as kinase inhibitors and kinase diagnostic probes, in particular as phosphoinositide 3-kinase (PI3K) and mammalian target of rapamycin (mTOR) inhibitor compounds with anti-cancer activity.

The compounds of the invention are potentially useful in the treatment of diseases, conditions and/or disorders modulated by PI3K and mTOR kinases. The compounds inhibit tumor growth in mammals, show anti-cancer activity, anti-inflammatory activity, immunoregulatory properties, and beneficial properties in associated pathological conditions.

The invention also relates to methods of using the compounds for in vitro, in situ, and in vivo diagnosis or treatment of mammalian cells and organisms, in particular human cancer patients.

More specifically, the invention provides enantio-enriched pyrimidine compounds of formula (Ia), (Ib), (IIa) and (IIb)

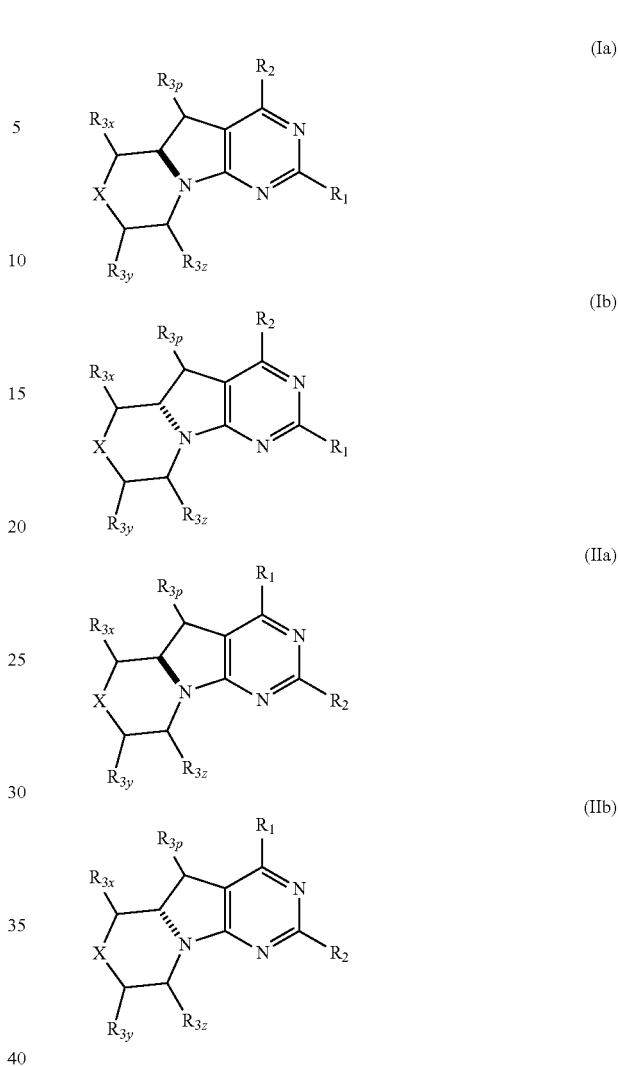

and stereoisomers, geometric isomers, tautomers, solvates and pharmaceutically acceptable salts thereof.

The substituents $R_1$, $R_2$ and $R_3$ are described hereinbelow.

In another aspect, the invention provides a pharmaceutical composition comprising compounds of formula (I) or (II), in particular of formula (Ia), (Ib), (IIa) or (IIb), and a pharmaceutically acceptable carrier. The pharmaceutical composition may further comprise one or more additional therapeutic agents selected from anti-proliferative agents, anti-inflammatory agents, immunomodulatory agents, neurotropic factors, agents for treating blood disorders, agents for treating diabetes, and agents for treating immunodeficiency disorders.

In another aspect, the invention provides a method of inhibiting PI3 kinase activity, comprising contacting a PI3 kinase with an effective inhibitory amount of a compound of formula (I) or (II), in particular of formula (Ia), (Ib), (IIa) or (IIb), or a stereoisomer, geometric isomer, tautomer, solvate, or pharmaceutically acceptable salt thereof.

In another aspect, the invention provides a method of preventing or treating a disease or disorder modulated by PI3 kinase, comprising administering to a mammal in need of such treatment an effective amount of a compound of formula (I) or (II), in particular of formula (Ia), (Ib), (IIa) and (IIb), or a stereoisomer, geometric isomer, tautomer, solvate, or pharmaceutically acceptable salt thereof.

Examples of such diseases, conditions and disorders include, but are not limited to, hyperproliferative disorders (e.g., cancer, including melanoma and other cancers of the skin), neurodegeneration, cardiac hypertrophy, pain, migraine, neurotraumatic diseases, stroke, diabetes, hepatomegaly, cardiovascular disease, Alzheimer's disease, cystic fibrosis, autoimmune diseases, atherosclerosis, restenosis, psoriasis, allergic disorders, inflammation, neurological disorders, hormone-related diseases, conditions associated with organ transplantation, immunodeficiency disorders, destructive bone disorders, hyperproliferative disorders, infectious diseases, conditions associated with cell death, thrombin-induced platelet aggregation, chronic myelogenous leukaemia (CML), liver disease, pathologic immune conditions involving T cell activation, and CNS disorders.

In another aspect, the invention provides a method of preventing or treating a hyperproliferative disorder, comprising administering to a mammal in need of such treatment an effective amount of a compound of formula (I) or (II), in particular of formula (Ia), (Ib), (IIa) or (IIb), or a stereoisomer, geometric isomer, tautomer, solvate, or pharmaceutically acceptable salt or thereof, alone or in combination with one or more additional compounds having anti-hyperproliferative properties. In a further aspect the present invention provides a method of using a compound of this invention to treat a disease or condition modulated by PI3 kinase and/or mTOR in a mammal.

An additional aspect of the invention is the use of a compound of this invention in the preparation of a medicament for the treatment or prevention of a disease or condition modulated by PI3 kinase in a mammal.

Another aspect of the invention includes kits comprising a compound of formula (I) or (II), in particular of formula (Ia), (Ib), (IIa) or (IIb), or a stereoisomer, geometric isomer, tautomer, solvate, or pharmaceutically acceptable salt thereof, a container, and optionally a package insert or label indicating a treatment.

Another aspect of the invention includes methods of preparing, methods of separating, and methods of purifying compounds of formula (I) or (II), in particular of formula (Ia), (Ib), (IIa) or (IIb), and novel intermediates useful for preparing compounds formula (I) or (II), in particular of formula (Ia), (Ib), (IIa) or (IIb).

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials herein described.

DEFINITIONS

The term "alkyl" as used herein refers to a saturated linear or branched-chain monovalent hydrocarbon group of one to twelve carbon atoms ($C_1$-$C_{12}$), wherein the alkyl group may be optionally substituted independently with one or more substituents described below. In another embodiment, an alkyl group is one to eight carbon atoms ($C_1$-$C_8$), or one to six carbon atoms ($C_1$-$C_6$). Examples of alkyl groups include, but are not limited to, methyl, ethyl, 1-propyl (n-propyl), 2-propyl (i-propyl), 1-butyl (n-butyl), 2-methyl-1-propyl (i-butyl), 2-butyl (s-butyl), 2-methyl-2-propyl (t-butyl), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like.

The term "alkenyl" refers to linear or branched-chain monovalent hydrocarbon radical of two to eight carbon atoms ($C_2$-$C_8$) with at least one site of unsaturation, i.e., a carbon-carbon, sp2 double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=CH$_2$), allyl (—CH$_2$CH=CH$_2$), and the like.

The term "alkynyl" refers to a linear or branched monovalent hydrocarbon radical of two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —CH$_2$C≡CH), and the like.

The term "halogen" (or halo) preferably represents chloro or fluoro, but may also be bromo or iodo.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene(phenyl), substituted benzenes, naphthalene, anthracene, biphenyl, indenyl, indanyl, 1,2-dihydronapthalene, 1,2,3,4-tetrahydronaphthyl, and the like. Aryl groups are optionally substituted independently with one or more substituents described herein.

The terms "heterocycle", "heterocyclyl" and "heterocyclic ring" are used interchangeably herein and refer to a saturated or a partially unsaturated (i.e., having one or more double and/or triple bonds within the ring) carbocyclic radical of 3 to 20 ring atoms in which at least one ring atom is a heteroatom selected from nitrogen, oxygen, phosphorus and sulphur, the remaining ring atoms being carbon atoms, wherein one or more ring atoms are optionally substituted independently with one or more substituents described below. A heterocycle may be a monocycle having 3 to 7 ring members (1 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly chapters 1, 3, 4, 6, 7, and 9; "The Chemistry of Heterocyclic Compounds, A series of Monographs" (John Wiley & Sons, New York, 1950 to present), in particular volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydro-furanyl, dihydrofuranyl, tetrahydrothienyl, tetrahydropyranyl, dihydropyranyl, tetrahydro-thiopyranyl, piperidino, morpholino, thiomorpholino, thioxanyl, piperazinyl, homo-piperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyclo [3.1.0]hexanyl, 3-azabicyclo[4.1.0]heptanyl, azabicyclo[2.2.2]octanyl, 3H-indolyl, and quinolizinyl. Spiro moieties are also included within the scope of this definition. Examples of a heterocyclic group wherein ring carbon atoms are substituted with oxo (=O) moieties are pyrimidinonyl and 1,1-dioxo-thiomorpholinyl. The heterocyclic groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulphur. Examples of heteroaryl groups are pyridinyl (including, for example, 2-hydroxy-pyridinyl), imidazolyl, imidazopyridinyl, pyrimidinyl (including, for example, 4-hydroxy-pyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydro-isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocyclic or heteroaryl groups may be bound through carbon (carbon-linked), or nitrogen (nitrogen-linked) where such is possible. By way of example and not limitation, carbon-linked heterocycles or heteroaryls are bound at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen-linked heterocycles or heteroaryls are bound at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole or 13-carboline.

The term "monocyclic heteroaryl" refers to a five- or six-membered, unsubstituted or substituted, monocyclic heteroaryl radical which contains 1, 2, 3 or 4 ring heteroatoms independently selected from N, O and S. Monocyclic heteroaryl radicals include, but are not limited to: 2-pyridyl, 3-pyridyl, 4-pyridyl, 3-isoxazolyl, 4-isoxazolyl, 5-isoxazolyl, 2-midazolyl, 4-imidazolyl, 3-pyrazolyl, 4-pyrazolyl, 2-pyrrolyl, 3-pyrrolyl, 2-thiazolyl, 4-thiazolyl, 5-thiazolyl, 3-pyridazinyl, 4-pyridazinyl, 5-pyridazinyl, 2-pyrimidinyl, 5-pyrimidinyl, 6-pyrimidinyl, 2-pyrazinyl, 2-oxazolyl, 4-oxazolyl, 5-oxazolyl, 2-furanyl, 3-furanyl, 2-thienyl, 3-thienyl, 3-triazolyl, 1-triazolyl, 5-tetrazolyl, 1-tetrazolyl, and 2-tetrazolyl. Monocyclic heteroaryl are optionally substituted independently with one or more substituents described herein.

The terms "treat" and "treatment" refer to both therapeutic treatment and prophylactic or preventative measures, wherein the object is to prevent or slow down (lessen) an undesired pathological change or disorder, such as the development or spread of cancer. For purpose of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may be reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TIP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukaemia or lymphoid malignancies.

More particular examples of such cancers include squamous cell cancer (e.g., epithelial squamous cell cancer), lung cancer including small-cell lung cancer, non-small cell lung cancer ("NSCLC"), adenocarcinoma of the lung, and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, bile duct cancer, mantle cell lymphoma, CNS lymphoma, chronic lymphocytic leukemia, non-Hodgkin's lymphoma, as well as head and neck cancer.

A "chemotherapeutic agent" is a chemical compound useful in the treatment of cancer. Examples of known chemotherapeutic agents include trastuzumab, pertuzumab, erlotinib (TARCEVA®, Genentech/Roche/OSI Pharm.), bortezomib (VELCADE®, Millennium Pharm.), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafarnib (SCH 66336), sorafenib (NEXAVAR, Bayer Labs), and gefitinib (IRESSA®, AstraZeneca), AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins; a camptothecin (including the synthetic analog topotecan); bryostatin; callystatin; CC-1065 (including its adozelesin, carzelesin and bizelesin synthetic analogs); cryptophycins; dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chloro-phosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammal 1 and calicheamicin omegal 1; dynemicin, including dynemicin A; biphosphonates, such as clodronate; an esperamicin; as well as neocarzinostatin chromophore and related chromoprotein enediyne antibiotic chromophores, aclacinomysins, actinomycin, authramycin, azaserine, bleomycins, cactinomycin, carabicin, carminomycin, carzinophillin, chromomycinis, dactinomycin, daunorubicin, detorubicin, 6-diazol-5-oxo-L-norleucine, ADRIAMYCIN® (doxorubicin), morpholino-doxorubicin, cyanomorpholino-doxorubicin, 2-pyrrolino-doxorubicin and deoxydoxorubicin, epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex; razoxane; rhizoxin; sizofiran; spirogermanium; tenuazonic acid; triaziquone; trichothecenes; urethane; indesine; dacarbazine; mannomustine; mitobronitol; mitolactol; pipobroman; gacytosine; arabinoside; taxoids, e.g., TAXOL® (paclitaxel; Bristol-Myers Squibb), ABRAXANE™ (Cremophor-free), albumin-engineered nanoparticle formulations of paclitaxel, and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide; ifosfamide; mitoxantrone; vincristine; NAVELBINE® (vinorelbine); novantrone; teniposide; edatrexate; daunomycin; aminopterin; capecitabine (XELODA®); ibandronate; CP-11; topoisomerase inhibitor RFS 2000; difluoromethyl-ornithine (DMFO); retinoids such as retinoic acid; and pharmaceutically acceptable salts; acids and derivatives of any of the above.

Also included in the definition of "chemotherapeutic agent" are: (i) anti-hormonal agents that act to regulate or inhibit hormone action on tumors such as anti-estrogens and selective receptor modulators (SERMs), including, for example, tamoxifen (including NOLVADEX®; tamoxifen citrate), raloxifene, droloxifene, and FARESTON® (toremifine citrate); (ii) aromatase inhibitors that inhibit the enzyme aromatase, which regulates estrogen production in the adrenal glands, such as, for example, 4(5)-imidazoles, MEGASE® (megestrol acetate); AROMASIN® (exemestane; Pfizer), formestanie, fadrazole, RIVISOR® (vorozole), FEMARA® (letrozole; Novartis), and ARIMIDEX® (anastrozole; AstraZeneca); (iii) anti-androgens such as flutamide, nilutamide; (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Raf I and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rII-2; a topoisomerase 1 inhibitor such as LURTOTECANE®; ABARELIX® rmRH; (ix) anti-angiogenic agents such as bevacizumab (AVASTIN®, Genentech/Roche); and (x) pharmaceutically acceptable salts, acids and derivatives of any of the above.

The term "prodrug" as used in this application refers to a precursor or derivative form of a compound of the invention that may be less cytotoxic to cells compared to the parent compound or drug and is capable of being enzymatically or hydrolytically activated or converted into the more active parent form. The prodrugs of this invention include, but are not limited to, phosphate-containing prodrugs, thiophosphate-containing prodrugs, sulfate-containing prodrugs, peptide-containing prodrugs, O-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

A "liposome" is a small vesicle composed of various types of lipids, phospholipids and/or surfactant, which is useful for delivery of a drug (such as the PI3K and mTOR kinase inhibitors disclosed herein and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules, which have the property of non-superimposability of the mirror image partner, while the term "achiral" refers to molecules, which are superimposable on their mirror image partner.

The term "stereoisomers" refers to compounds, which have identical chemical constitution, but differ with regard to the arrangement of the atoms or groups in space.

"Diastereomer" refers to a stereoisomer with two or more centers of chirality in which the compounds are not mirror images of one another. Diastereomers have different physical properties, e.g. melting points, boiling points, spectral properties, and chemical and biological reactivities. Mixtures of diastereomers may be separated under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McRaw-Hiff Dictionary of Chemical Terms* (1984), McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate. The term "tautomer" or "tautomeric form" refers to structural isomers of different energies, which are interconvertible via a low energy barrier. For example, proton tautomers include interconversions via migration of a proton, such as keto-enol and imine-enamine isomerizations.

The phrase "pharmaceutically acceptable salt" as used herein, refers to pharmaceutically acceptable organic or inorganic salts of a compound of the invention. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate (mesylate), ethanesulfonate, benzenesulfonate, p-toluenesulfonate, and pamoate salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine, an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminium and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, dimethyl sulfoxide (DMSO), ethyl acetate, acetic acid, and ethanolamine. The term "hydrate" refers to the complex where the solvent molecule is water.

The term "protecting group" refers to a substituent that is commonly employed to block or protect a particular functionality during the reaction of other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl and 9-fluorenylmethylenoxycarbonyl (Fmoc). For a general description of protecting groups and their use, see T. W. Greene, Protective Groups I Organic Synthesis, John Wiley & Sons, New York, 1991.

The terms "compound of this invention" and "compounds of the present invention" and "compounds of formula (I) or (II)" or "compounds of formula (Ia), (Ib), (IIa) and (IIb)" include stereoisomers, geometric isomers, tautomers, solvates, and pharmaceutically acceptable salts thereof.

The term "mammal" includes, but is not limited to, humans, mice, rats, guinea, pigs, monkeys, dogs, cats, horses, cows, pigs, and sheep.

The present invention provides new morpholino-dihydropyrrolo-pyrimidines and related compounds, and pharmaceutical formulations thereof, which are useful as therapeutic agents and novel diagnostic probes. Moreover, these compounds are potentially useful in the treatment of diseases, conditions and/or disorders modulated by protein kinases and lipid kinases.

More specifically, the present invention provides compounds of formula (I) and (II),

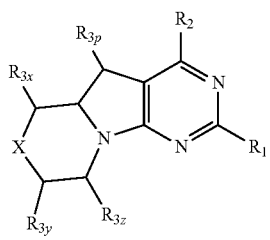

(I)

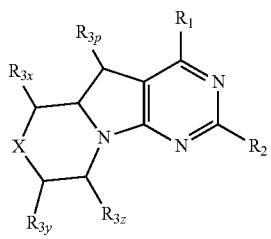

(II)

and stereoisomers, geometric isomers, tautomers, solvates, and pharmaceutically acceptable salts thereof, wherein $R_1$ is

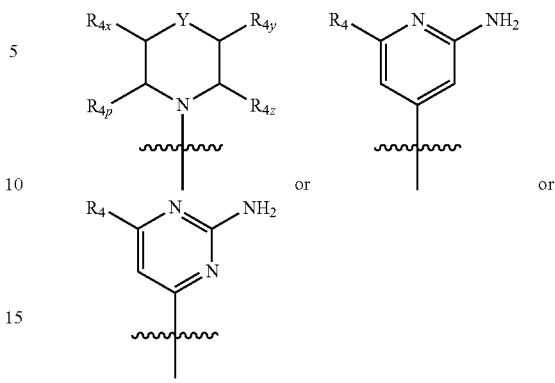

X and Y are independently selected from the group consisting of $C(R_8)_2$, O, S, SO, $SO_2$, and $NR_7$;

$R_{3x}$, $R_{3y}$, $R_{3z}$, $R_{3p}$ and $R_4$ are independently selected from the group consisting of hydrogen, D (i.e. deuterium), F, Cl, Br, I, $C_1$-$C_{12}$ alkyl, $C_2$-$C_8$ alkenyl, $C_2$-$C_8$ alkynyl, —($C_1$-$C_{12}$ alkylene)-($C_3$-$C_{12}$ carbocyclyl), —($C_1$-$C_{12}$ alkylene)-(heterocyclyl having 3-20 ring atoms), —($C_1$-$C_{12}$ alkylene)-C(=O)-(heterocyclyl having 3-20 ring atoms), —($C_1$-$C_{12}$ alkylene)-($C_6$-$C_{20}$ aryl) and —($C_1$-$C_{12}$ alkylene)-(heteroaryl having 5-20 ring atoms), —C($C_1$-$C_6$ alkyl)$_2$NR$_5$R$_6$, —(CR$_8$R$_9$)$_n$NR$_5$R$_6$, —(CR$_8$R$_9$)$_n$NR$_7$C(=Z)R$_8$, (CR$_8$R$_9$)$_n$NR$_7$ S(O)$_2$R$_5$, —CH(OR$_5$)R$_6$, —(CR$_8$R$_9$)$_n$OR$_5$, —(CR$_8$R$_9$)$_n$ S(O)$_2$R$_5$, —(CR$_8$R$_9$)$_n$S(O)$_2$NR$_5$R$_6$, —C(=Z)R$_5$, —C(=Z)OR$_5$, C(=Z)NR$_5$R$_6$, —C(=Z)NR$_7$OR$_5$, —C(=O)NR$_7$S(O)$_2$R$_5$, —C(=O)NR$_7$(CR$_8$R$_9$)$_m$—NR$_5$R$_6$, —NO$_2$, —NHR$_7$, —NR$_7$C(=Z)R$_5$, —NR$_7$C(=Z)OR$_5$, —NR$_7$C(=Z)NR$_5$R$_6$, —NR$_7$S(O)$_2$R$_5$, —NR$_7$SO$_2$NR$_5$R$_6$, —S(O)$_2$R$_5$, —S(O)$_2$NR$_5$R$_6$, —SC(=Z)R$_5$, —SC(=Z)OR$_5$, $C_3$-$C_{12}$ carbocyclyl, $C_2$-$C_{20}$ heterocyclyl, $C_6$-$C_{20}$ aryl, and $C_1$—C=NR$_7$, OR$_5$, —OC(=Z)R$_5$, —OC(=Z)OR$_5$, —OC(=Z)NR$_5$R$_6$, and —OS(O)$_2$(OR$_5$);

$R_{4x}$, $R_{4y}$, $R_{4z}$ and $R_{4p}$ are independently selected from the group consisting of hydrogen, D, F, Cl, Br, I, $C_1$-$C_{12}$ alkyl, $C_2$-$C_8$ alkenyl, $C_2$-$C_8$ alkynyl, or one or two of $R_{4x}$, $R_{4y}$, $R_{4z}$ and $R_{4p}$ are two geminal substituents methyl and the other ones are hydrogen, or $R_{4x}$ and $R_{4p}$, or $R_{4y}$ and $R_{4z}$ form together an annullated five- or six-membered carbocyclyl, heterocyclyl, aryl or heteroaryl ring, or $R_{4x}$ and $R_{4y}$ form together bridging ethylene or methylene, $R_{4p}$ and $R_{4z}$ form together bridging ethylene or methylene, or $R_{4y}$ and $R_{4p}$ form together bridging ethylene or methylene;

wherein said alkyl, alkenyl, alkynyl, carbocyclyl, heterocyclyl, aryl and heteroaryl are optionally substituted with one or more groups independently selected from F, Cl, Br, I, CN, CF$_3$, NO$_2$, oxo, —C(=Z)R$_5$, —C(=Z)OR$_5$, —C(=Z)NR$_5$R$_6$, —(CR$_8$R$_9$)$_n$NR$_5$R$_6$, —(CR$_8$R$_9$)$_n$C(=Z)NR$_5$R$_6$, —(CR$_8$R$_9$)$_n$C(=Z)OR$_5$, —(CR$_8$R$_9$)$_n$NR$_7$SO$_2$R$_5$, —(CR$_8$R$_9$)$_n$OR$_5$, —(CR$_8$R$_9$)$_n$R$_5$, —(CR$_8$R$_9$)$_n$SO$_2$R$_5$, —NR$_5$R$_6$, —NR$_7$C(=Z)R$_5$, —NR$_7$C(=Z)OR$_5$, —NR$_7$C(=Z)NR$_5$R$_6$, —NR$_7$SO$_2$R$_5$), —OP(OR$_5$)(OR$_6$), SR$_5$, —S(O)R$_5$, —S(O)$_2$R$_5$, —S(O)$_2$NR$_5$R$_6$, —S(O)(OR$_5$), —S(O)$_2$(OR$_5$), —SC(=Z)R$_5$, —SC(=Z)OR$_5$, —SC(=Z)NR$_5$R$_6$, optionally substituted $C_1$-$C_{12}$ alkyl, optionally substituted $C_2$-$C_8$ alkenyl, optionally substituted $C_2$-$C_8$ alkynyl, optionally substituted $C_3$-$C_{12}$ carbocyclyl, optionally substituted $C_2$-$C_{20}$ heterocyclyl, optionally substituted $C_6$-$C_{20}$ aryl, and optionally substituted $C_1$-$C_{20}$ heteroaryl;

$R_5$, $R_6$ and $R_7$ are independently selected from H, D, $C_1$-$C_{12}$ alkyl, $C_2$-$C_8$ alkenyl, $C_3$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl, or $R_5$ and $R_6$ together with the nitrogen to which they are attached form a $C_3$-$C_{20}$ heterocyclic ring optionally containing one or more additional ring atoms selected from N, O or S, wherein said heterocyclic ring is optionally substituted with one or more groups independently selected from oxo, $CF_3$, F, Cl, Br, I, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl and $C_1$-$C_{20}$ heteroaryl;

$R_8$ and $R_9$ are independently selected from H, D, $C_1$-$C_{12}$ alkyl, and —$(CH_2)_n$-aryl, or $R_8$ and $R_9$ together with the atoms to which they are attached form a saturated or partially unsaturated $C_3$-$C_{12}$ carbocyclic ring;

m is 0, 1, 2, 3, 4, 5 or 6;

n is 1, 2, 3, 4, 5, or 6;

t is 2, 3, 4, 5 or 6; and $R_2$ is independently selected from the groups consisting of a monocyclic or bicyclic aryl or heteroaryl with 1-6 heteroatoms selected from O, N, S, with 1-4 substituents selected from $C_1$-$C_4$ alkyl, D, F, Cl, Br, I, —$OR_5$, —COOH, $COOR_5$, —$CONR_5R_6$, —$SO_2NR_5R_6$, CN, $CF_3$, $CHF_2$, $CFH_2$, $OCF_3$, $OCOR_5$, $NR_7COR_5$, $NR_7SO_2R_5$, $NR_5R_6$, $SO_2R_5$, $SOR_5$, and $SR_5$.

$R_2$ with the meaning monocyclic aryl is preferably phenyl, meta- or para-substituted phenyl or 2,4-, 3,4- or 3,5-disubstituted phenyl, wherein the substituents are selected from halogen, $C_1$-$C_6$-alkyl, halo-$C_1$-$C_6$-alkyl, hydroxy, $C_1$-$C_6$-alkoxy, or optionally $C_1$-$C_6$-alkylated or $C_1$-$C_{20}$-acylated amino.

$R_2$ with the meaning heteroaryl is preferably selected from optionally substituted pyridinyl, imidazolyl, pyrimidinyl, furyl, indolyl, benzimidazolyl, indazolyl, oxadiazolyl, and thiadiazolyl, wherein the substituents are selected from $C_1$-$C_6$-alkyl, halo-$C_1$-$C_6$-alkyl, pyridyl, aminopyridyl, amino or $C_1$-$C_8$-acylamino, wherein $C_1$-$C_8$-acyl is a $C_1$-$C_7$-alkyl, halo-$C_1$-$C_7$-alkyl, $C_2$-$C_7$-alkenyl, pyridyl or aminopyridyl group connected to carbonyl, oxycarbonyl such as methoxycarbonyl, or aminocarbonyl such as methylaminocarbonyl or optionally substituted arylaminocarbonyl, for example [4-(4-dimethylaminopiperidino)-carbonylphenyl]aminocarbonyl; and combinations thereof.

More preferably, $R_2$ with the meaning heteroaryl is pyridinyl or pyrimidinyl, wherein the substituents are selected from $C_1$-$C_6$-alkyl, halo-$C_1$-$C_6$-alkyl, pyridyl, aminopyridyl, amino or $C_1$-$C_8$-acylamino, wherein $C_1$-$C_8$-acyl is a $C_1$-$C_7$-alkyl, halo-$C_1$-$C_7$alkyl, $C_2$-$C_7$alkenyl, pyridyl or aminopyridyl group connected to carbonyl, oxycarbonyl such as methoxycarbonyl, or aminocarbonyl such as methylaminocarbonyl or optionally substituted arylaminocarbonyl; and combinations thereof.

Preferred examples of $R_2$ are selected from the group consisting of

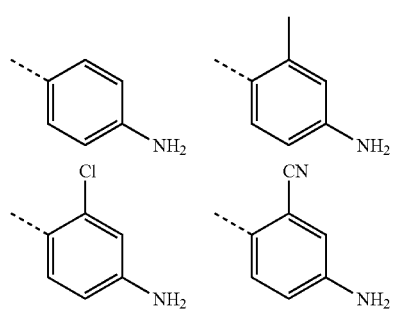

-continued

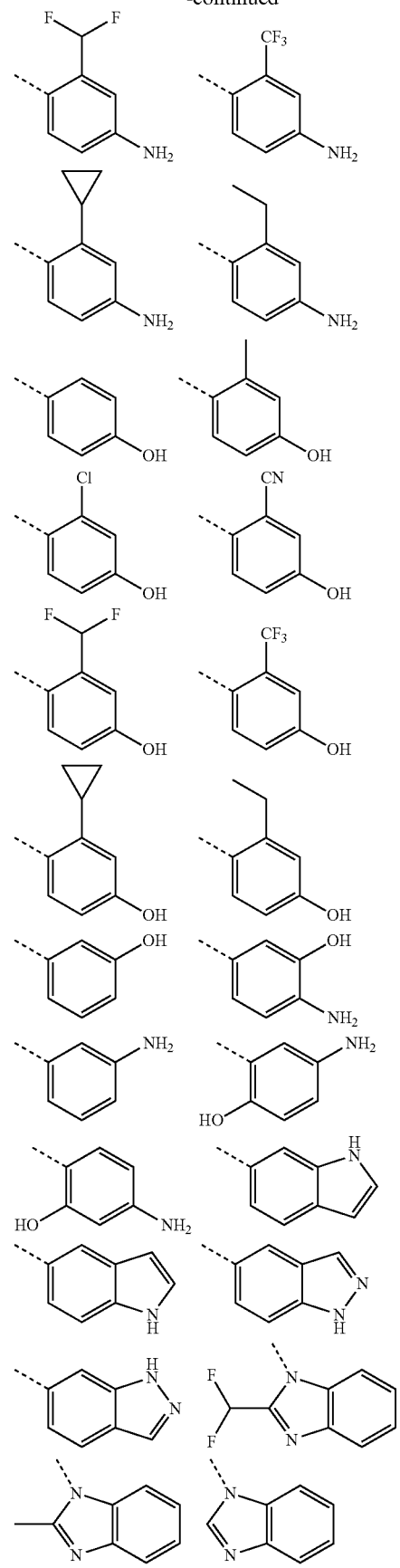

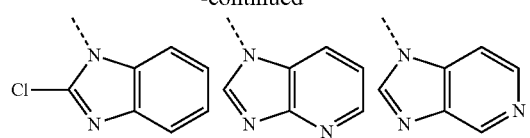
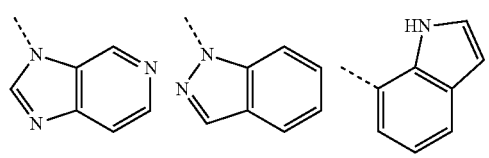
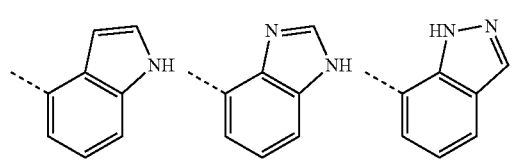
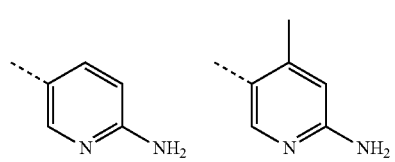
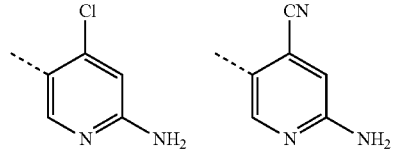
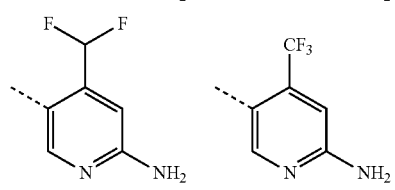
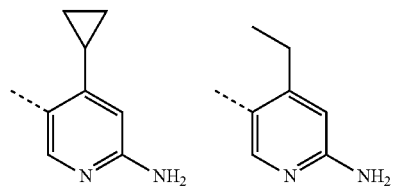
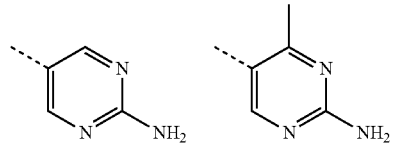
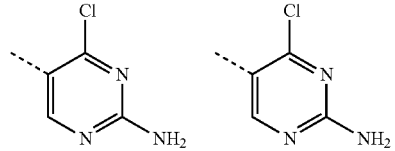
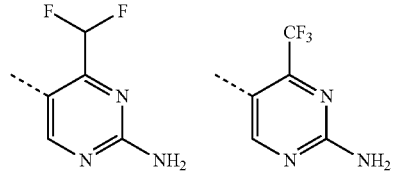
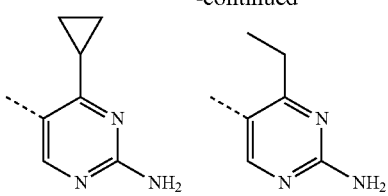
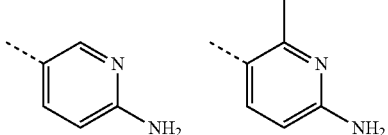
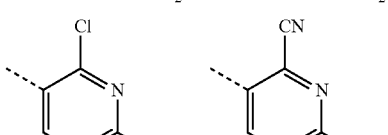
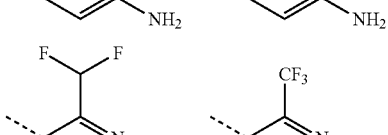
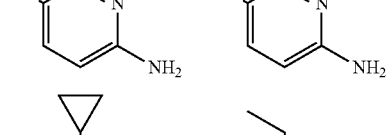
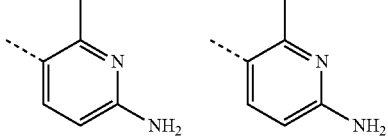
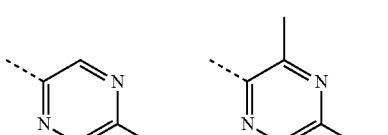
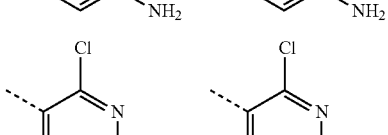
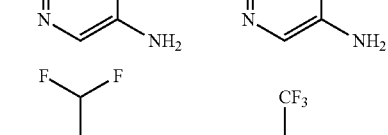
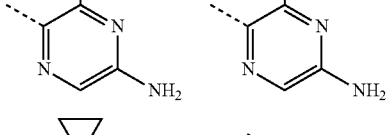
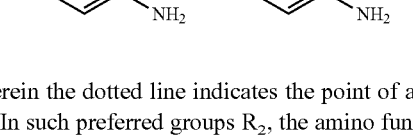
wherein the dotted line indicates the point of attachment of $R_2$. In such preferred groups $R_2$, the amino function may be further substituted with $C_1$-$C_8$-acyl, oxycarbonyl or aminocarbonyl as defined above.

Most preferred examples of R₂ are listed below:
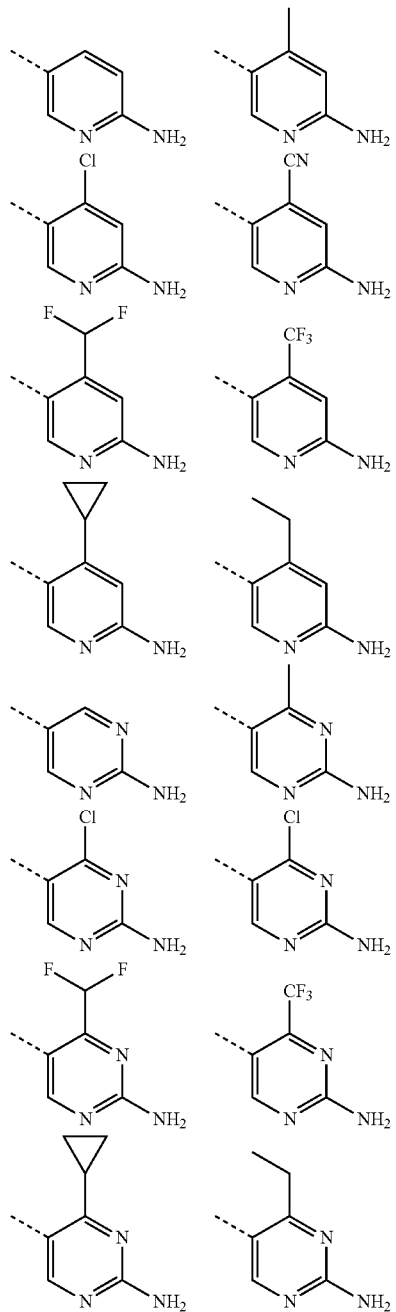
Preferably Y is O (the ring containing Y being morpholine). In such preferred morpholines, the substituents $R_{4x}$, $R_{4y}$, $R_{4z}$ and $R_{4p}$ are preferably chosen such that morpholines correspond to substituents $R_1$ of the following structures:
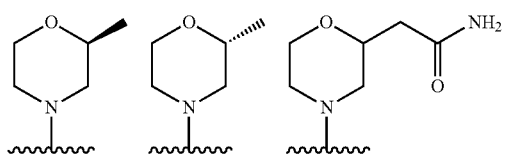
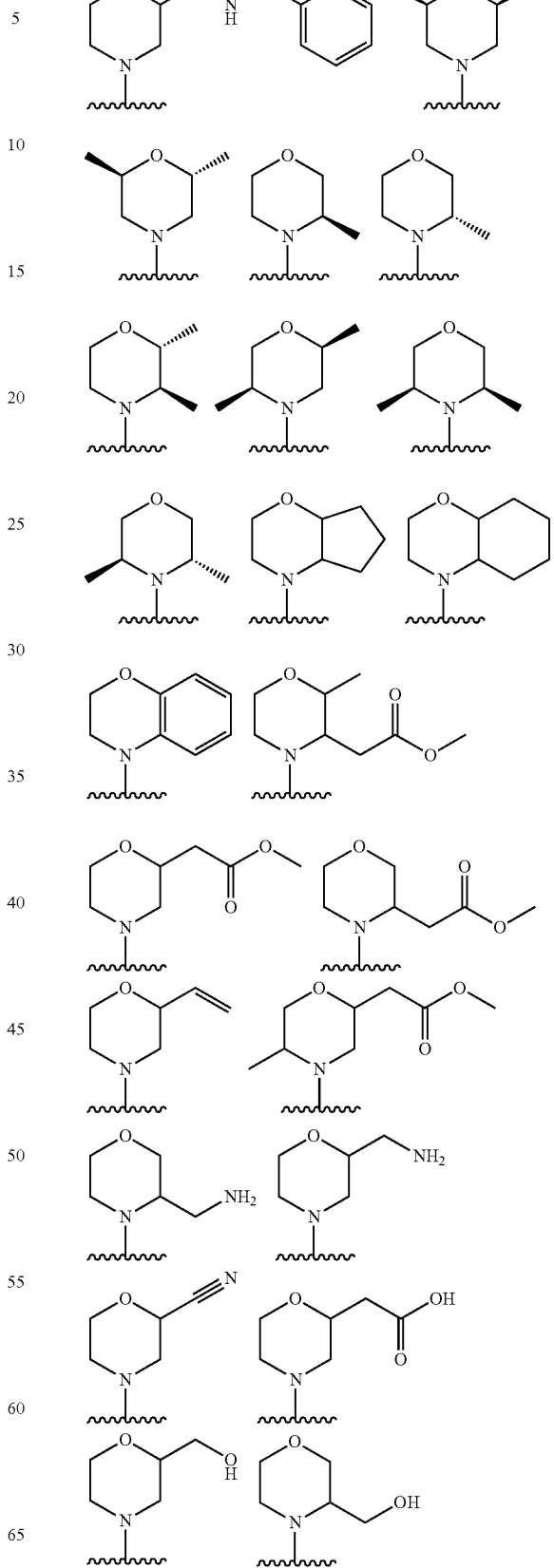

-continued

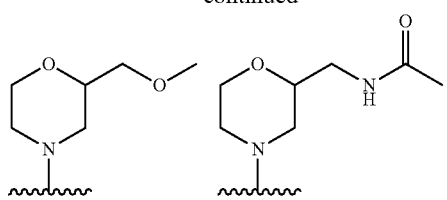

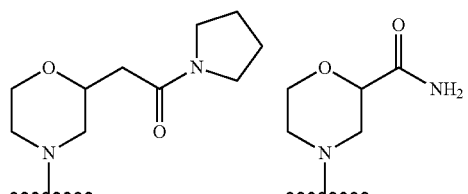

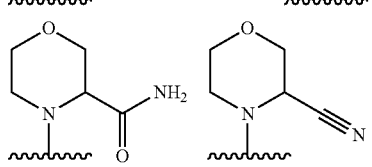

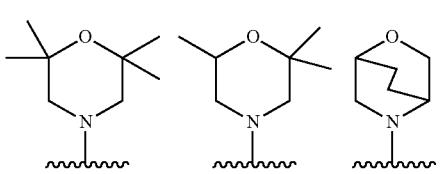

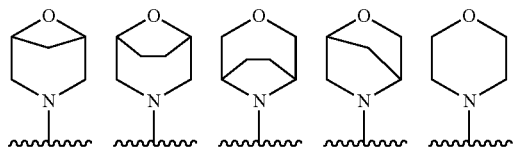

optionally further substituted with one or more groups independently selected from D, F, Cl, Br, I, —CH₃, —CH₂CH₃, —CH₂CH₂CH₃, —CH(CH₃)₂, —C(CH₃)₃, —CH₂OCH₃, —CHF₂, —CN, —CF₃, —CH₂OH, —CH₂OCH₃, —CH₂CH₂OH, —CH₂C(CH₃)₂OH, —CH(CH₃)OH, —CH(CH₂CH₃)OH —CH₂CH(OH)CH₃, —C(CH₃)₂OH, —C(CH₃)₂OCH₃, —CH(CH₃)F, —C(CH₃)F₂, —CH(CH₂CH₃)F, —C(CH₂CH₃)₂F, —CO₂H, —CONH₂, —CON(CH₂CH₃)₂, —COCH₃, —CON(CH₃)₂, —NO₂, —NH₂, —NHCH₃, —N(CH₃)₂, —NHCH₂CH₃, —NHCH(CH₃)₂, —NHCH₂CH₂OH, —NHCH₂CH₂OCH₃, —NHCOCH₃, —NHCOCH₂CH₃, —NHCOCH₂OH, —NHS(O)₂CH₃, —N(CH₃)S(O)₂CH₃, =O, —OH, —OCH₃, —OCH₂CH₃, —OCH(CH₃)₂, —SH, —NHC(=O)NHCH₃, —NHC(=O)NHCH₂CH₃, —S(O)CH₃, —S(O)CH₂CH₃, —S(O)₂CH₃, —S(O)₂NH₂, —S(O)₂NHCH₃, —S(O)₂N(CH₃)₂, and —CH₂S(O)₂CH₃; wherein the wavy line indicates the attachment of R₁ to the pyrimidine ring.

Preferred examples of R₁ are listed below:

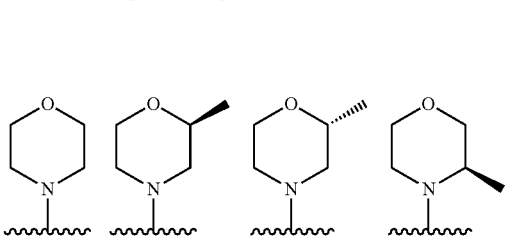

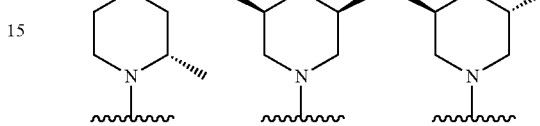

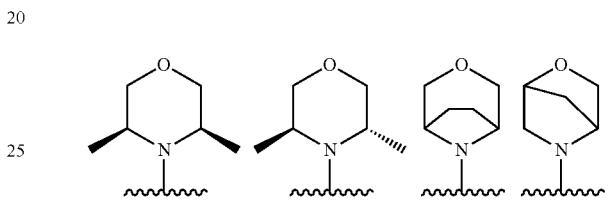

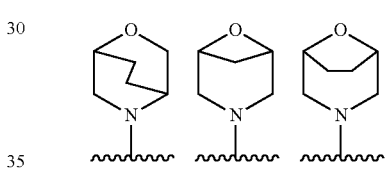

Most preferred example of R₁ is morpholino.

Preferably X is O or S (the ring containing X being an annullated morpholine or thiomorpholine, respectively). Most preferably X is O.

Most preferred R₃ₓ is H. Most preferred R₃ᵧ is H. Most preferred R₃ᵤ is H. Most preferred R₃ₚ is H. Most preferred R₄ is H. Most preferred R₄ₓ is H. Most preferred R₄ᵧ is H. Most preferred R₄ᵤ is H. Most preferred R₄ₚ is H. Most preferred R₅ is H. Most preferred R₆ is H. Most preferred R₇ is H. Most preferred R₈ is H. Most preferred R₉ is H. Most preferred m is 1. Most preferred n is 1. Most preferred t is 1.

Preferably, the present invention provides compounds of formula (Ia) and (Ib):

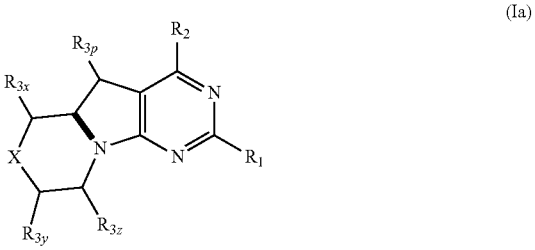

(Ia)

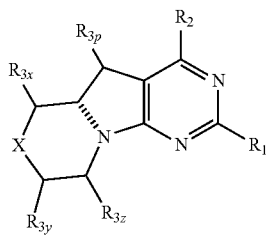

(Ib)

and stereoisomers, geometric isomers, tautomers, solvates, and pharmaceutically acceptable salts thereof, wherein $R_1$, $R_2$, $R_{3x}$, $R_{3y}$, $R_{3z}$, and $R_{3p}$ are as defined above for formula (I).

The preferences, particular aspects and embodiments set forth above for $R_1$, $R_2$, $R_{3x}$, $R_{3y}$, $R_{3z}$, and $R_{3p}$ in formula (I) apply likewise to these structures in formula (Ia) and (Ib).

In another aspect, the invention provides compounds of formula (IIa) and (IIb)

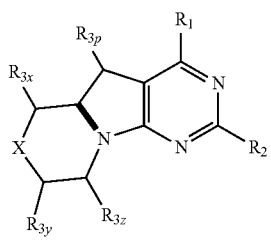

(IIa)

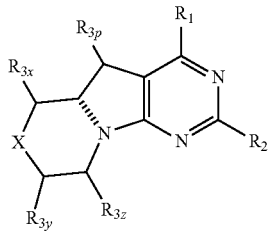

(IIb)

and stereoisomers, geometric isomers, tautomers, solvates, and pharmaceutically acceptable salts thereof, wherein $R_1$, $R_2$, $R_{3x}$, $R_{3y}$, $R_{3z}$, $R_{3p}$ are as defined above for formula (II).

The preferences, particular aspects and embodiments set forth above for $R_1$, $R_2$, $R_{3x}$, $R_{3y}$, $R_{3z}$, and $R_{3p}$ in formula (II) apply likewise to these structures in formula (IIa) and (IIb).

Most preferred examples are described in Tables 1 to 4.

Table 1 gives the structures and the corresponding IUPAC names (using ChemDraw Ultra, Version 13.0.1 as well as lower and upper software versions thereof, CambridgeSoft Corp., Cambridge Mass.) of exemplary compounds (Cpd) Nos. 1-16 of formula (Ia).

| Cpd No. | Structure | Name |
|---|---|---|
| 1 | 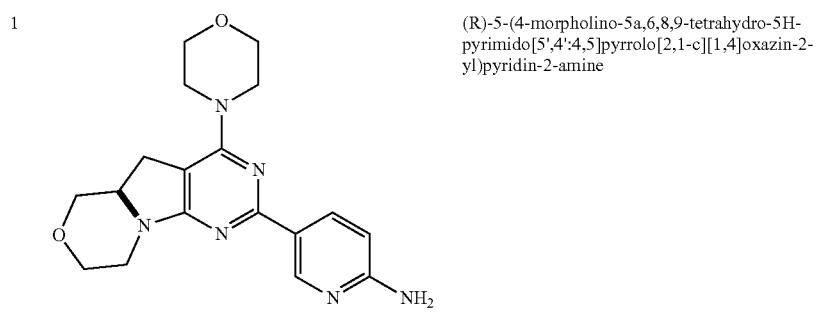 | (R)-5-(4-morpholino-5a,6,8,9-tetrahydro-5H-pyrimido[5',4':4,5]pyrrolo[2,1-c][1,4]oxazin-2-yl)pyridin-2-amine |
| 2 | 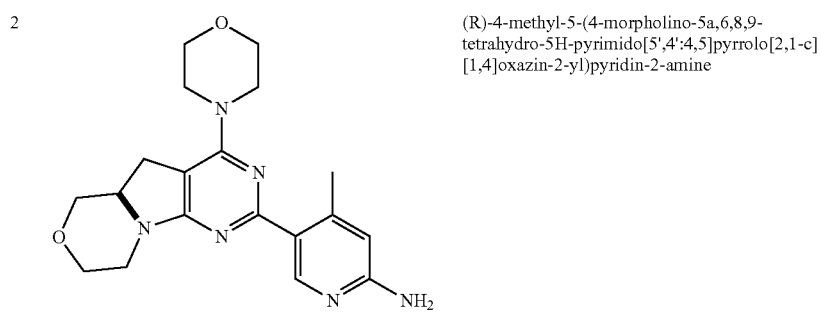 | (R)-4-methyl-5-(4-morpholino-5a,6,8,9-tetrahydro-5H-pyrimido[5',4':4,5]pyrrolo[2,1-c][1,4]oxazin-2-yl)pyridin-2-amine |

-continued

| Cpd No. | Structure | Name |
|---|---|---|
| 3 | 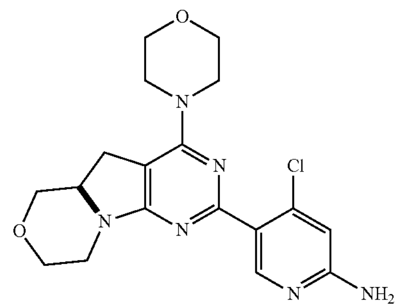 [SMILES: Nc1cc(Cl)c(-c2nc(N3CCOCC3)c3c(n2)N2CCOC[C@H]2C3)cn1] | (R)-4-chloro-5-(4-morpholino-5a,6,8,9-tetrahydro-5H-pyrimido[5',4':4,5]pyrrolo[2,1-c][1,4]oxazin-2-yl)pyridin-2-amine |
| 4 | 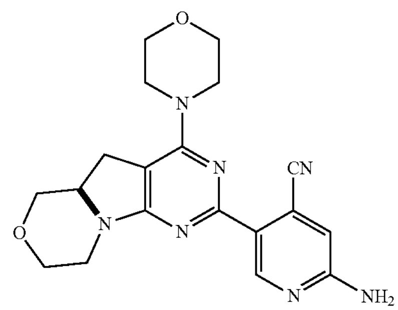 | (R)-2-amino-5-(4-morpholino-5a,6,8,9-tetrahydro-5H-pyrimido[5',4':4,5]pyrrolo[2,1-c][1,4]oxazin-2-yl)isonicotinonitrile |
| 5 | 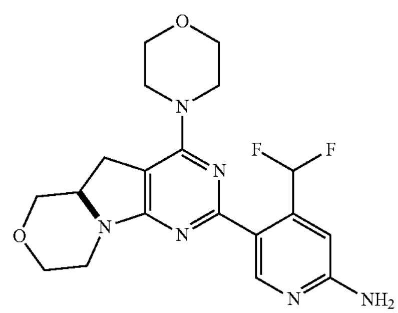 [SMILES: Nc1cc(C(F)F)c(-c2nc(N3CCOCC3)c3c(n2)N2CCOC[C@H]2C3)cn1] | (R)-4-(difluoromethyl)-5-(4-morpholino-5a,6,8,9-tetrahydro-5H-pyrimido[5',4':4,5]pyrrolo[2,1-c][1,4]oxazin-2-yl)pyridin-2-amine |
| 6 | 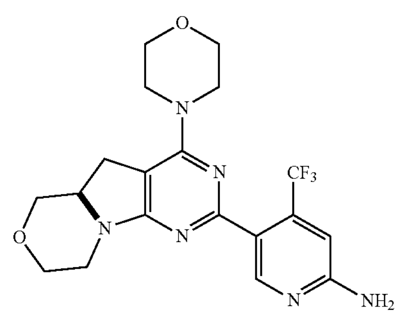 | (R)-5-(4-morpholino-5a,6,8,9-tetrahydro-5H-pyrimido[5',4':4,5]pyrrolo[2,1-c][1,4]oxazin-2-yl)-4-(trifluoromethyl)pyridin-2-amine |
| 7 | 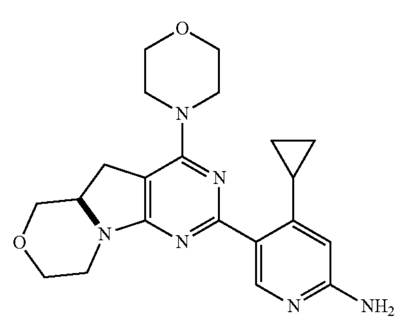 [SMILES: Nc1cc(C2CC2)c(-c2nc(N3CCOCC3)c3c(n2)N2CCOC[C@H]2C3)cn1] | (R)-4-cyclopropyl-5-(4-morpholino-5a,6,8,9-tetrahydro-5H-pyrimido[5',4':4,5]pyrrolo[2,1-c][1,4]oxazin-2-yl)pyridin-2-amine |

-continued

| Cpd No. | Structure | Name |
|---|---|---|
| 8 | 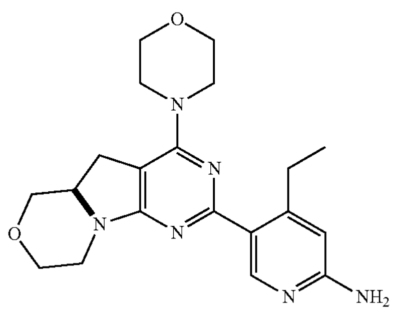 [SMILES: CCc1cc(N)ncc1-c1nc(N2CCOCC2)c2c(n1)N1CCOC[C@H]1C2] | (R)-4-ethyl-5-(4-morpholino-5a,6,8,9-tetrahydro-5H-pyrimido[5',4':4,5]pyrrolo[2,1-c][1,4]oxazin-2-yl)pyridin-2-amine |
| 9 | 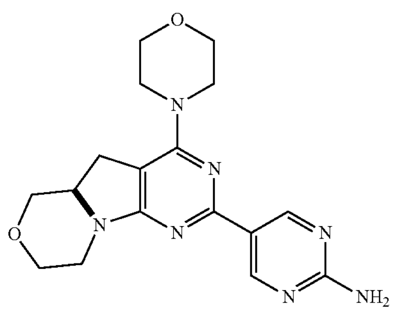 [SMILES: Nc1ncc(-c2nc(N3CCOCC3)c3c(n2)N2CCOC[C@H]2C3)cn1] | (R)-5-(4-morpholino-5a,6,8,9-tetrahydro-5H-pyrimido[5',4':4,5]pyrrolo[2,1-c][1,4]oxazin-2-yl)pyrimidin-2-amine |
| 10 | 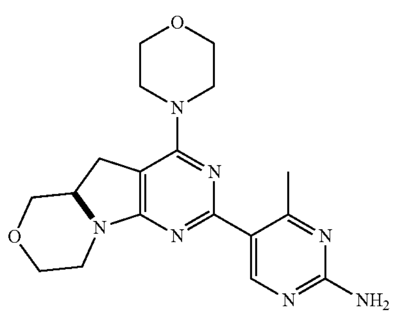 [SMILES: Cc1nc(N)ncc1-c1nc(N2CCOCC2)c2c(n1)N1CCOC[C@H]1C2] | (R)-4-methyl-5-(4-morpholino-5a,6,8,9-tetrahydro-5H-pyrimido[5',4':4,5]pyrrolo[2,1-c][1,4]oxazin-2-yl)pyrimidin-2-amine |
| 11 | 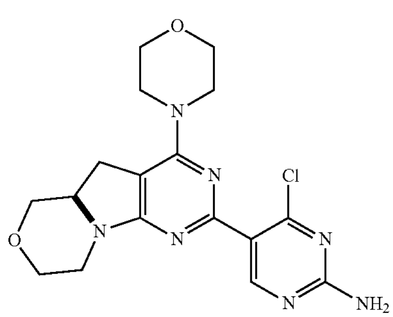 | (R)-4-chloro-5-(4-morpholino-5a,6,8,9-tetrahydro-5H-pyrimido[5',4':4,5]pyrrolo[2,1-c][1,4]oxazin-2-yl)pyrimidin-2-amine |
| 12 | 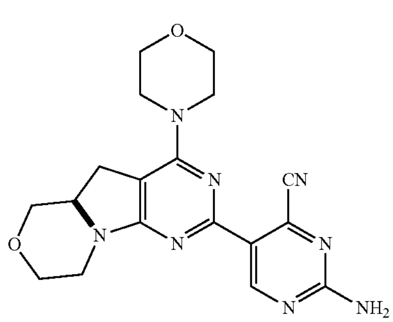 [SMILES: N#Cc1nc(N)ncc1-c1nc(N2CCOCC2)c2c(n1)N1CCOC[C@H]1C2] | (R)-2-amino-5-(4-morpholino-5a,6,8,9-tetrahydro-5H-pyrimido[5',4':4,5]pyrrolo[2,1-c][1,4]oxazin-2-yl)pyrimidine-4-carbonitrile |

| Cpd No. | Structure | Name |
|---|---|---|
| 13 | 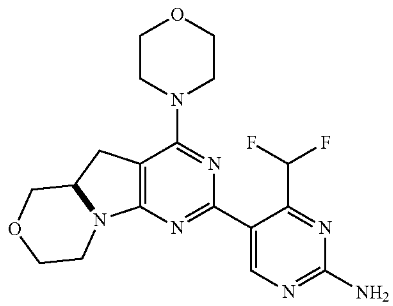 | (R)-4-(difluoromethyl)-5-(4-morpholino-5a,6,8,9-tetrahydro-5H-pyrimido[5',4':4,5]pyrrolo[2,1-c][1,4]oxazin-2-yl)pyrimidin-2-amine |
| 14 | 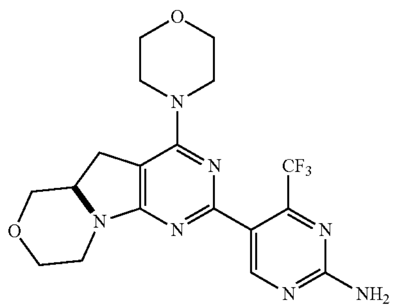 | (R)-5-(4-morpholino-5a,6,8,9-tetrahydro-5H-pyrimido[5',4':4,5]pyrrolo[2,1-c][1,4]oxazin-2-yl)-4-(trifluoromethyl)pyrimidin-2-amine |
| 15 | 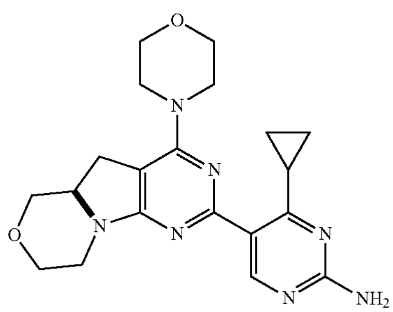 [SMILES: Nc1ncc(-c2nc(N3CCOCC3)c3c(n2)N2CCOC[C@H]2C3)c(C2CC2)n1] | (R)-4-cyclopropyl-5-(4-morpholino-5a,6,8,9-tetrahydro-5H-pyrimido[5',4':4,5]pyrrolo[2,1-c][1,4]oxazin-2-yl)pyrimidin-2-amine |
| 16 | 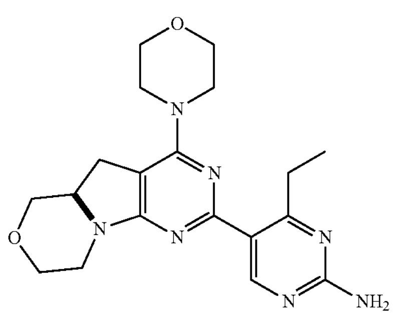 | (R)-4-ethyl-5-(4-morpholino-5a,6,8,9-tetrahydro-5H-pyrimido[5',4':4,5]pyrrolo[2,1-c][1,4]oxazin-2-yl)pyrimidin-2-amine |

Table 2 gives the structures and the corresponding IUPAC names (using ChemDraw Ultra, Version 13.0.1 as well as lower and upper software versions thereof, CambridgeSoft Corp., Cambridge Mass.) of exemplary compounds (Cpd) Nos. 17-32 of formula (Ib).

| Cpd No. | Structure | Name |
|---|---|---|
| 17 | 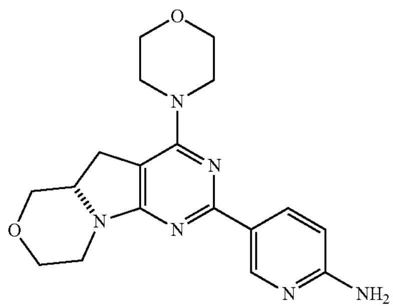 [SMILES: Nc1ccc(-c2nc(N3CCOCC3)c3c(n2)N2CCOC[C@@H]2C3)cn1] | (S)-5-(4-morpholino-5a,6,8,9-tetrahydro-5H-pyrimido[5',4':4,5]pyrrolo[2,1-c][1,4]oxazin-2-yl)pyridin-2-amine |
| 18 | 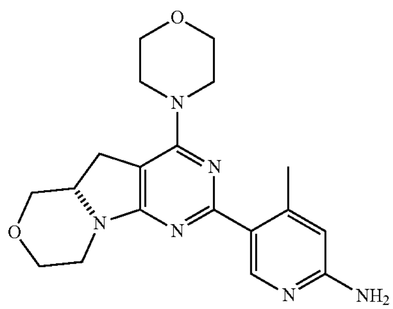 | (S)-4-methyl-5-(4-morpholino-5a,6,8,9-tetrahydro-5H-pyrimido[5',4':4,5]pyrrolo[2,1-c][1,4]oxazin-2-yl)pyridin-2-amine |
| 19 | 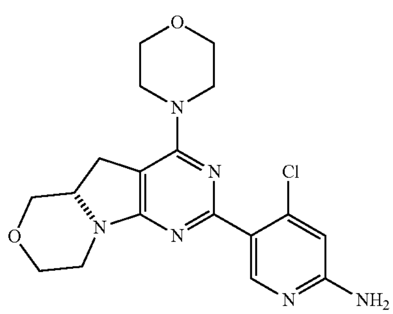 [SMILES: Nc1cc(Cl)c(-c2nc(N3CCOCC3)c3c(n2)N2CCOC[C@@H]2C3)cn1] | (S)-4-chloro-5-(4-morpholino-5a,6,8,9-tetrahydro-5H-pyrimido[5',4':4,5]pyrrolo[2,1-c][1,4]oxazin-2-yl)pyridin-2-amine |
| 20 | 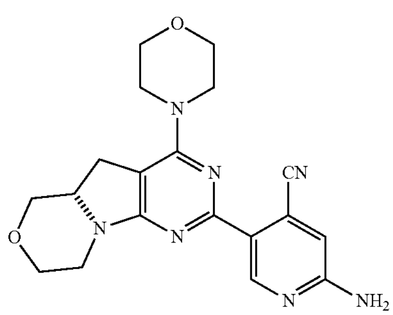 | (S)-2-amino-5-(4-morpholino-5a,6,8,9-tetrahydro-5H-pyrimido[5',4':4,5]pyrrolo[2,1-c][1,4]oxazin-2-yl)isonicotinonitrile |
| 21 | 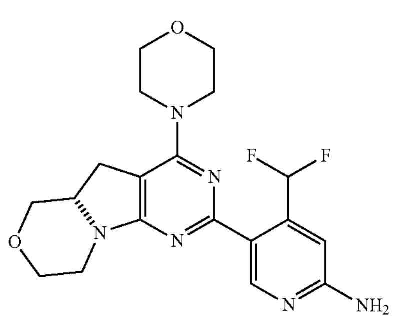 [SMILES: Nc1cc(C(F)F)c(-c2nc(N3CCOCC3)c3c(n2)N2CCOC[C@@H]2C3)cn1] | (S)-4-(difluoromethyl)-5-(4-morpholino-5a,6,8,9-tetrahydro-5H-pyrimido[5',4':4,5]pyrrolo[2,1-c][1,4]oxazin-2-yl)pyridin-2-amine |

| Cpd No. | Structure | Name |
|---|---|---|
| 22 | 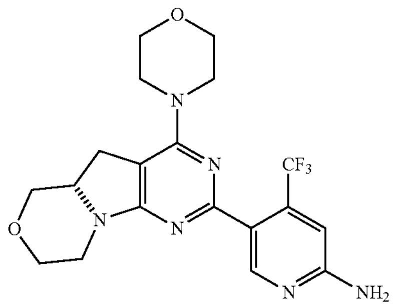 | (S)-5-(4-morpholino-5a,6,8,9-tetrahydro-5H-pyrimido[5',4':4,5]pyrrolo[2,1-c][1,4]oxazin-2-yl)-4-(trifluoromethyl)pyridin-2-amine |
| 23 | 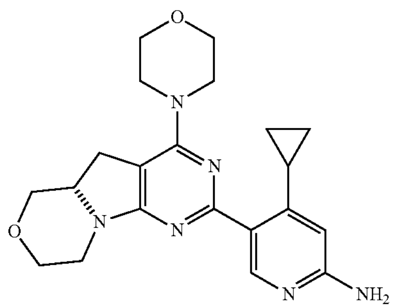 [SMILES: Nc1cc(C2CC2)c(-c2nc(N3CCOCC3)c3c(n2)N2CCOC[C@@H]2C3)cn1] | (S)-4-cyclopropyl-5-(4-morpholino-5a,6,8,9-tetrahydro-5H-pyrimido[5',4':4,5]pyrrolo[2,1-c][1,4]oxazin-2-yl)pyridin-2-amine |
| 24 | 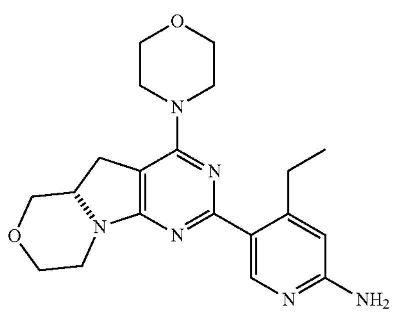 [SMILES: CCc1cc(N)ncc1-c1nc(N2CCOCC2)c2c(n1)N1CCOC[C@@H]1C2] | (S)-4-ethyl-5-(4-morpholino-5a,6,8,9-tetrahydro-5H-pyrimido[5',4':4,5]pyrrolo[2,1-c][1,4]oxazin-2-yl)pyridin-2-amine |
| 25 | 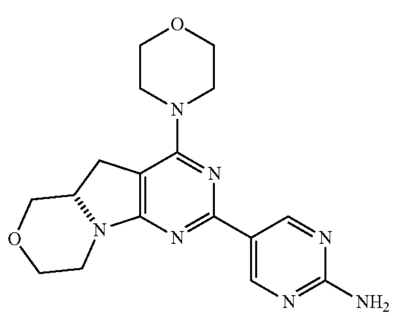 | (S)-5-(4-morpholino-5a,6,8,9-tetrahydro-5H-pyrimido[5',4':4,5]pyrrolo[2,1-c][1,4]oxazin-2-yl)pyrimidin-2-amine |
| 26 | 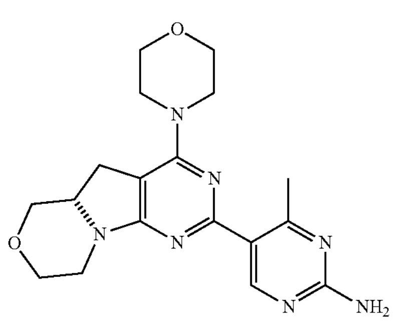 [SMILES: Nc1ncc(-c2nc(N3CCOCC3)c3c(n2)N2CCOC[C@@H]2C3)c(Cl)n1] | (S)-4-methyl-5-(4-morpholino-5a,6,8,9-tetrahydro-5H-pyrimido[5',4':4,5]pyrrolo[2,1-c][1,4]oxazin-2-yl)pyrimidin-2-amine |

-continued

| Cpd No. | Structure | Name |
|---|---|---|
| 27 | 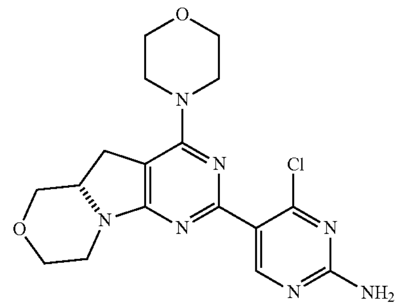 | (S)-4-chloro-5-(4-morpholino-5a,6,8,9-tetrahydro-5H-pyrimido[5',4':4,5]pyrrolo[2,1-c][1,4]oxazin-2-yl)pyrimidin-2-amine |
| 28 | 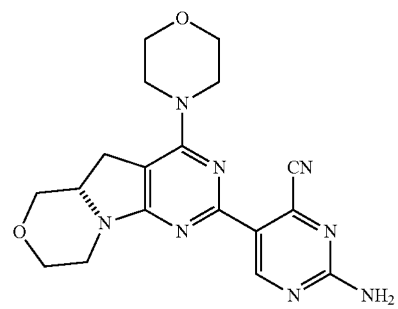 [SMILES: N#Cc1nc(N)ncc1-c1nc(N2CCOCC2)c2c(n1)N1CCOC[C@@H]1C2] | (S)-2-amino-5-(4-morpholino-5a,6,8,9-tetrahydro-5H-pyrimido[5',4':4,5]pyrrolo[2,1-c][1,4]oxazin-2-yl)pyrimidine-4-carbonitrile |
| 29 | 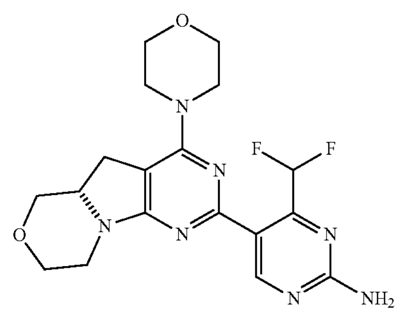 [SMILES: Nc1ncc(-c2nc(N3CCOCC3)c3c(n2)N2CCOC[C@@H]2C3)c(C(F)F)n1] | (S)-4-(difluoromethyl)-5-(4-morpholino-5a,6,8,9-tetrahydro-5H-pyrimido[5',4':4,5]pyrrolo[2,1-c][1,4]oxazin-2-yl)pyrimidin-2-amine |
| 30 | 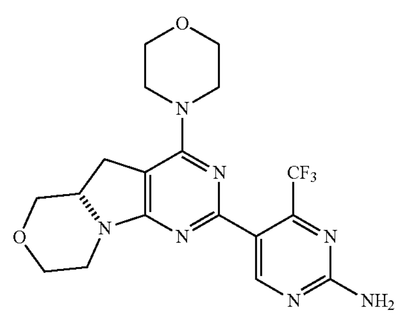 | (S)-5-(4-morpholino-5a,6,8,9-tetrahydro-5H-pyrimido[5',4':4,5]pyrrolo[2,1-c][1,4]oxazin-2-yl)-4-(trifluoromethyl)pyrimidin-2-amine |
| 31 | 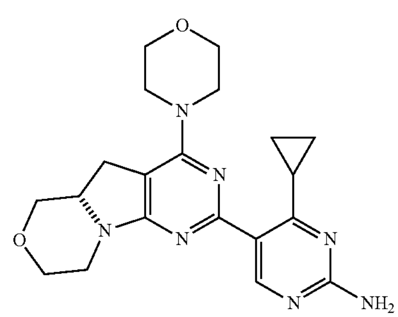 | (S)-4-cyclopropyl-5-(4-morpholino-5a,6,8,9-tetrahydro-5H-pyrimido[5',4':4,5]pyrrolo[2,1-c][1,4]oxazin-2-yl)pyrimidin-2-amine |

| Cpd No. | Structure | Name |
|---|---|---|
| 32 | 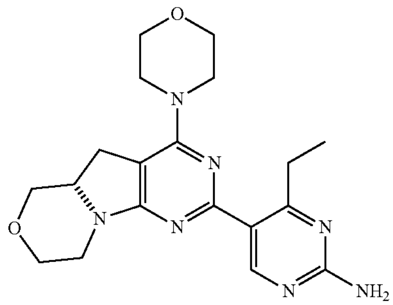 | (S)-4-ethyl-5-(4-morpholino-5a,6,8,9-tetrahydro-5H-pyrimido[5',4':4,5]pyrrolo[2,1-c][1,4]oxazin-2-yl)pyrimidin-2-amine |

Table 3 gives the structures and the corresponding IUPAC names (using ChemDraw Ultra, Version 13.0.1 as well as lower and upper software versions thereof, CambridgeSoft Corp., Cambridge Mass.) of exemplary compounds (Cpd) Nos. 33-48 of formula (IIa).

| Cpd No. | Structure | Name |
|---|---|---|
| 33 | 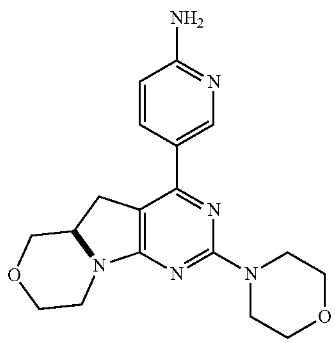 [SMILES: Nc1ccc(-c2nc(N3CCOCC3)nc3c2C[C@@H]2COCCN32)cn1] | (R)-5-(2-morpholino-5a,6,8,9-tetrahydro-5H-pyrimido[5',4':4,5]pyrrolo[2,1-c][1,4]oxazin-4-yl)pyridin-2-amine |
| 34 | 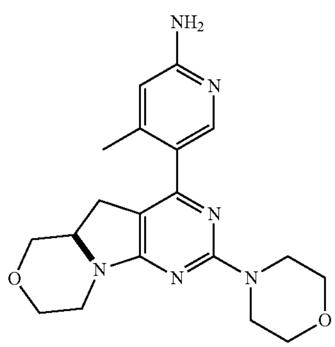 [SMILES: Cc1cc(N)ncc1-c1nc(N2CCOCC2)nc2c1C[C@@H]1COCCN21] | (R)-4-methyl-5-(2-morpholino-5a,6,8,9-tetrahydro-5H-pyrimido[5',4':4,5]pyrrolo[2,1-c][1,4]oxazin-4-yl)pyridin-2-amine |
| 35 | 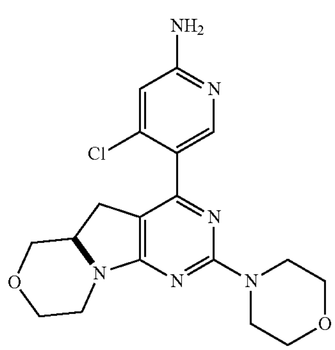 [SMILES: Nc1cc(Cl)c(-c2nc(N3CCOCC3)nc3c2C[C@@H]2COCCN32)cn1] | (R)-4-chloro-5-(2-morpholino-5a,6,8,9-tetrahydro-5H-pyrimido[5',4':4,5]pyrrolo[2,1-c][1,4]oxazin-4-yl)pyridin-2-amine |

| Cpd No. | Structure | Name |
|---|---|---|
| 36 | 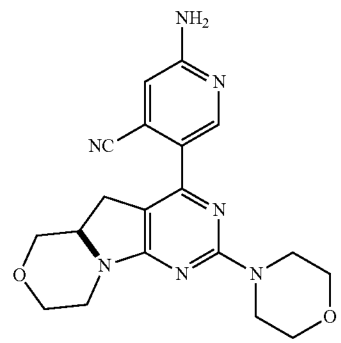 [SMILES: N#Cc1cc(N)ncc1-c1nc(N2CCOCC2)nc2c1C[C@@H]1COCCN21] | (R)-2-amino-5-(2-morpholino-5a,6,8,9-tetrahydro-5H-pyrimido[5',4':4,5]pyrrolo[2,1-c][1,4]oxazin-4-yl)isonicotinonitrile |
| 37 | 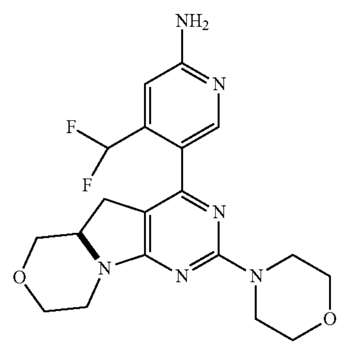 [SMILES: Nc1cc(C(F)F)c(-c2nc(N3CCOCC3)nc3c2C[C@@H]2COCCN32)cn1] | (R)-4-(difluoromethyl)-5-(2-morpholino-5a,6,8,9-tetrahydro-5H-pyrimido[5',4':4,5]pyrrolo[2,1-c][1,4]oxazin-4-yl)pyridin-2-amine |
| 38 | 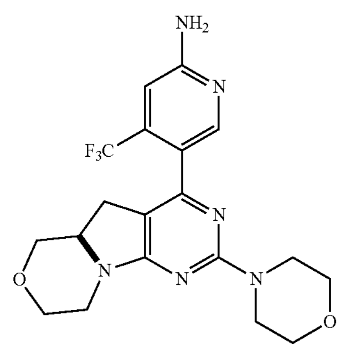 [SMILES: Nc1cc(C(F)(F)F)c(-c2nc(N3CCOCC3)nc3c2C[C@@H]2COCCN32)cn1] | (R)-5-(2-morpholino-5a,6,8,9-tetrahydro-5H-pyrimido[5',4':4,5]pyrrolo[2,1-c][1,4]oxazin-4-yl)-4-(trifluoromethyl)pyridin-2-amine |
| 39 | 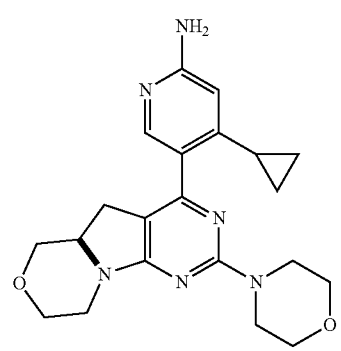 [SMILES: Nc1cc(C2CC2)c(-c2nc(N3CCOCC3)nc3c2C[C@@H]2COCCN32)cn1] | (R)-4-cyclopropyl-5-(2-morpholino-5a,6,8,9-tetrahydro-5H-pyrimido[5',4':4,5]pyrrolo[2,1-c][1,4]oxazin-4-yl)pyridin-2-amine |

| Cpd No. | Structure | Name |
|---|---|---|
| 40 | 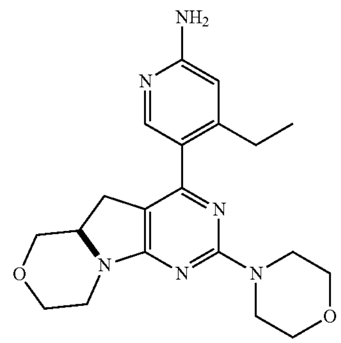 [SMILES: CCc1cc(N)ncc1-c1nc(N2CCOCC2)nc2c1C[C@@H]1COCCN21] | (R)-4-ethyl-5-(2-morpholino-5a,6,8,9-tetrahydro-5H-pyrimido[5',4':4,5]pyrrolo[2,1-c][1,4]oxazin-4-yl)pyridin-2-amine |
| 41 | 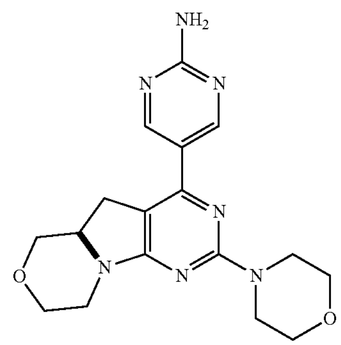 [SMILES: Nc1ncc(-c2nc(N3CCOCC3)nc3c2C[C@@H]2COCCN32)cn1] | (R)-5-(2-morpholino-5a,6,8,9-tetrahydro-5H-pyrimido[5',4':4,5]pyrrolo[2,1-c][1,4]oxazin-4-yl)pyrimidin-2-amine |
| 42 | 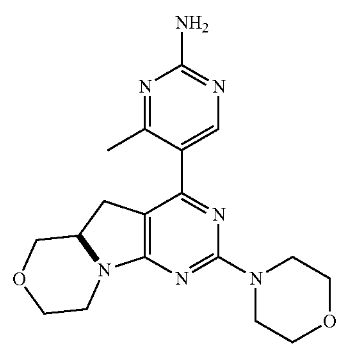 [SMILES: Cc1nc(N)ncc1-c1nc(N2CCOCC2)nc2c1C[C@@H]1COCCN21] | (R)-4-methyl-5-(2-morpholino-5a,6,8,9-tetrahydro-5H-pyrimido[5',4':4,5]pyrrolo[2,1-c][1,4]oxazin-4-yl)pyrimidin-2-amine |
| 43 | 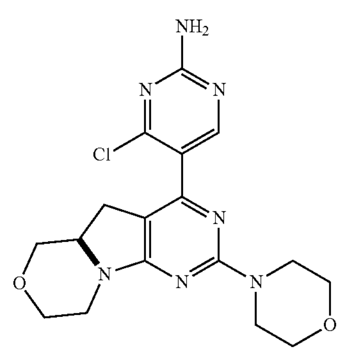 [SMILES: Nc1ncc(-c2nc(N3CCOCC3)nc3c2C[C@@H]2COCCN32)c(Cl)n1] | (R)-4-chloro-5-(2-morpholino-5a,6,8,9-tetrahydro-5H-pyrimido[5',4':4,5]pyrrolo[2,1-c][1,4]oxazin-4-yl)pyrimidin-2-amine |

| Cpd No. | Structure | Name |
|---|---|---|
| 44 | 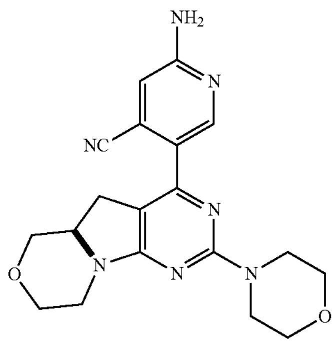 [SMILES: N#Cc1cc(N)ncc1-c1nc(N2CCOCC2)nc2c1C[C@@H]1COCCN21] | (R)-2-amino-5-(2-morpholino-5a,6,8,9-tetrahydro-5H-pyrimido[5',4':4,5]pyrrolo[2,1-c][1,4]oxazin-4-yl)isonicotinonitrile |
| 45 | 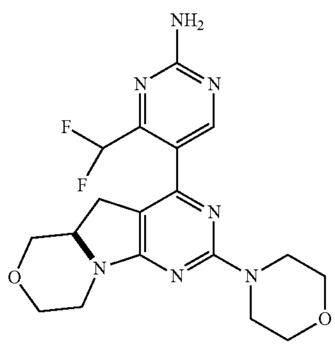 [SMILES: Nc1ncc(-c2nc(N3CCOCC3)nc3c2C[C@@H]2COCCN32)c(C(F)F)n1] | (R)-4-(difluoromethyl)-5-(2-morpholino-5a,6,8,9-tetrahydro-5H-pyrimido[5',4':4,5]pyrrolo[2,1-c][1,4]oxazin-4-yl)pyrimidin-2-amine |
| 46 | 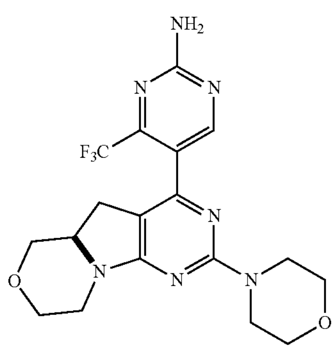 [SMILES: Nc1ncc(-c2nc(N3CCOCC3)nc3c2C[C@@H]2COCCN32)c(C(F)(F)F)n1] | (R)-5-(2-morpholino-5a,6,8,9-tetrahydro-5H-pyrimido[5',4':4,5]pyrrolo[2,1-c][1,4]oxazin-4-yl)-4-(trifluoromethyl)pyrimidin-2-amine |
| 47 | 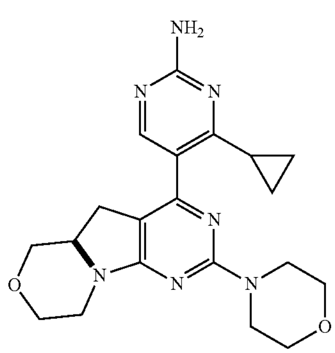 [SMILES: Nc1ncc(-c2nc(N3CCOCC3)nc3c2C[C@@H]2COCCN32)c(C2CC2)n1] | (R)-4-cyclopropyl-5-(2-morpholino-5a,6,8,9-tetrahydro-5H-pyrimido[5',4':4,5]pyrrolo[2,1-c][1,4]oxazin-4-yl)pyrimidin-2-amine |

| Cpd No. | Structure | Name |
|---|---|---|
| 48 | 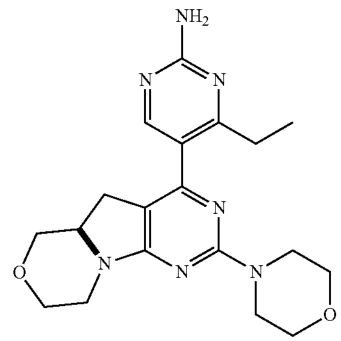 [SMILES: CCc1nc(N)ncc1-c1nc(N2CCOCC2)nc2c1C[C@@H]1COCCN21] | (R)-4-ethyl-5-(2-morpholino-5a,6,8,9-tetrahydro-5H-pyrimido[5',4':4,5]pyrrolo[2,1-c][1,4]oxazin-4-yl)pyrimidin-2-amine |

Table 4 gives the structures and the corresponding IUPAC names (using ChemDraw Ultra, Version 13.0.1 as well as lower and upper software versions thereof, CambridgeSoft Corp., Cambridge Mass.) of exemplary compounds (Cpd) Nos. 49-64 of formula (IIb).

| Cpd No. | Structure | Name |
|---|---|---|
| 49 | 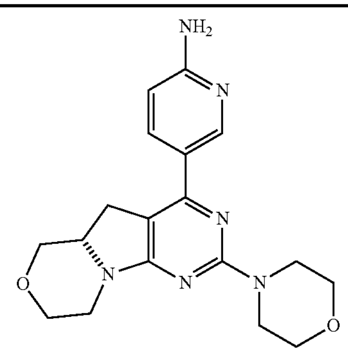 | (S)-5-(2-morpholino-5a,6,8,9-tetrahydro-5H-pyrimido[5',4':4,5]pyrrolo[2,1-c][1,4]oxazin-4-yl)pyridin-2-amine |
| 50 | 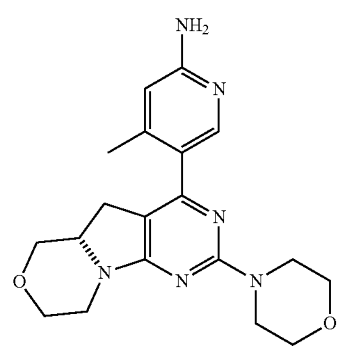 [SMILES: Cc1cc(N)ncc1-c1nc(N2CCOCC2)nc2c1C[C@H]1COCCN21] | (S)-4-methyl-5-(2-morpholino-5a,6,8,9-tetrahydro-5H-pyrimido[5',4':4,5]pyrrolo[2,1-c][1,4]oxazin-4-yl)pyridin-2-amine |
| 51 | 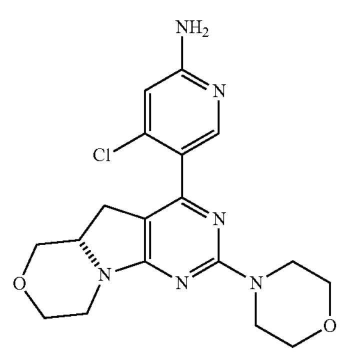 [SMILES: Nc1cc(Cl)c(-c2nc(N3CCOCC3)nc3c2C[C@H]2COCCN32)cn1] | (S)-4-chloro-5-(2-morpholino-5a,6,8,9-tetrahydro-5H-pyrimido[5',4':4,5]pyrrolo[2,1-c][1,4]oxazin-4-yl)pyridin-2-amine |

| Cpd No. | Structure | Name |
|---|---|---|
| 52 | 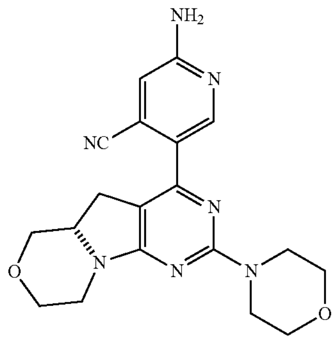 [SMILES: N#Cc1cc(N)ncc1-c1nc(N2CCOCC2)nc2c1C[C@H]1COCCN21] | (S)-2-amino-5-(2-morpholino-5a,6,8,9-tetrahydro-5H-pyrimido[5',4':4,5]pyrrolo[2,1-c][1,4]oxazin-4-yl)isonicotinonitrile |
| 53 | 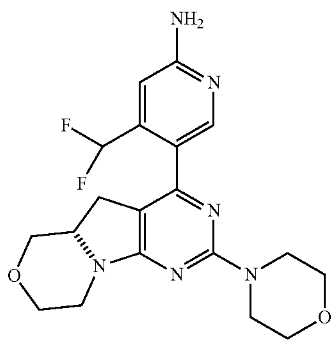 [SMILES: Nc1cc(C(F)F)c(-c2nc(N3CCOCC3)nc3c2C[C@H]2COCCN32)cn1] | (S)-4-(difluoromethyl)-5-(2-morpholino-5a,6,8,9-tetrahydro-5H-pyrimido[5',4':4,5]pyrrolo[2,1-c][1,4]oxazin-4-yl)pyridin-2-amine |
| 54 | 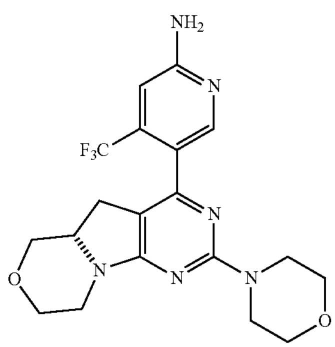 [SMILES: Nc1cc(C(F)(F)F)c(-c2nc(N3CCOCC3)nc3c2C[C@H]2COCCN32)cn1] | (S)-5-(2-morpholino-5a,6,8,9-tetrahydro-5H-pyrimido[5',4':4,5]pyrrolo[2,1-c][1,4]oxazin-4-yl)-4-(trifluoromethyl)pyridin-2-amine |
| 55 | 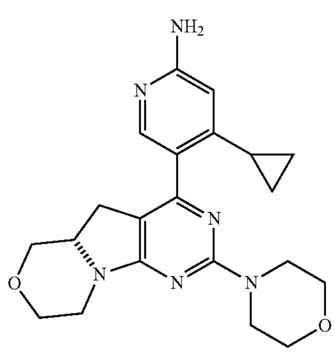 [SMILES: Nc1cc(C2CC2)c(-c2nc(N3CCOCC3)nc3c2C[C@H]2COCCN32)cn1] | (S)-4-cyclopropyl-5-(2-morpholino-5a,6,8,9-tetrahydro-5H-pyrimido[5',4':4,5]pyrrolo[2,1-c][1,4]oxazin-4-yl)pyridin-2-amine |

-continued

| Cpd No. | Structure | Name |
|---|---|---|
| 56 | 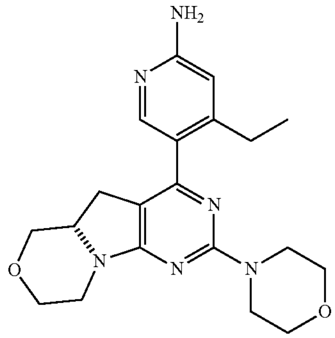 [SMILES: CCc1cc(N)ncc1-c1nc(N2CCOCC2)nc2c1C[C@H]1COCCN21] | (S)-4-ethyl-5-(2-morpholino-5a,6,8,9-tetrahydro-5H-pyrimido[5',4':4,5]pyrrolo[2,1-c][1,4]oxazin-4-yl)pyridin-2-amine |
| 57 | 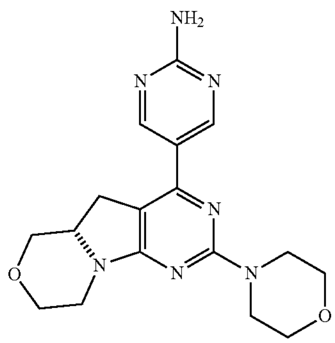 [SMILES: Nc1ncc(-c2nc(N3CCOCC3)nc3c2C[C@H]2COCCN32)cn1] | (S)-5-(2-morpholino-5a,6,8,9-tetrahydro-5H-pyrimido[5',4':4,5]pyrrolo[2,1-c][1,4]oxazin-4-yl)pyrimidin-2-amine |
| 58 | 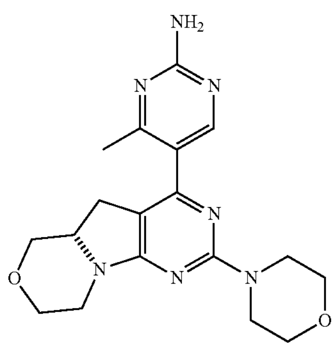 [SMILES: Cc1nc(N)ncc1-c1nc(N2CCOCC2)nc2c1C[C@H]1COCCN21] | (S)-4-methyl-5-(2-morpholino-5a,6,8,9-tetrahydro-5H-pyrimido[5',4':4,5]pyrrolo[2,1-c][1,4]oxazin-4-yl)pyrimidin-2-amine |
| 59 | 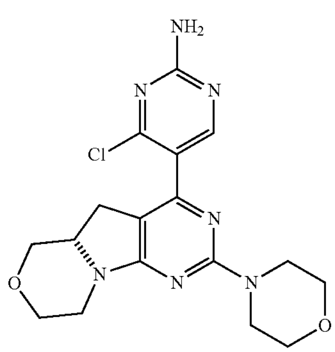 [SMILES: Nc1ncc(-c2nc(N3CCOCC3)nc3c2C[C@H]2COCCN32)c(Cl)n1] | (S)-4-chloro-5-(2-morpholino-5a,6,8,9-tetrahydro-5H-pyrimido[5',4':4,5]pyrrolo[2,1-c][1,4]oxazin-4-yl)pyrimidin-2-amine |

-continued

| Cpd No. | Structure | Name |
|---|---|---|
| 60 | 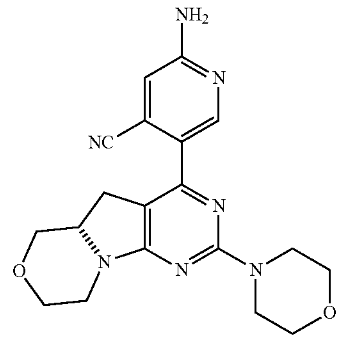 [SMILES: N#Cc1cc(N)ncc1-c1nc(N2CCOCC2)nc2c1C[C@H]1COCCN21] | (S)-2-amino-5-(2-morpholino-5a,6,8,9-tetrahydro-5H-pyrimido[5',4':4,5]pyrrolo[2,1-c][1,4]oxazin-4-yl)isonicotinonitrile |
| 61 | 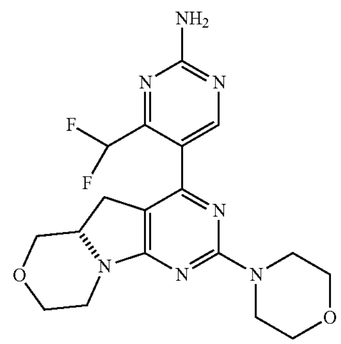 [SMILES: Nc1ncc(-c2nc(N3CCOCC3)nc3c2C[C@H]2COCCN32)c(C(F)F)n1] | (S)-4-(difluoromethyl)-5-(2-morpholino-5a,6,8,9-tetrahydro-5H-pyrimido[5',4':4,5]pyrrolo[2,1-c][1,4]oxazin-4-yl)pyrimidin-2-amine |
| 62 | 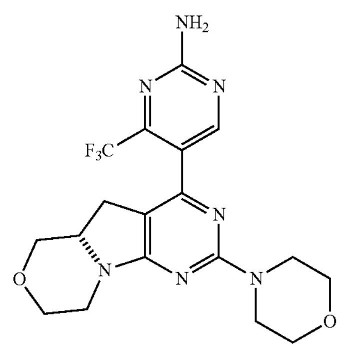 [SMILES: Nc1ncc(-c2nc(N3CCOCC3)nc3c2C[C@H]2COCCN32)c(C(F)(F)F)n1] | (S)-5-(2-morpholino-5a,6,8,9-tetrahydro-5H-pyrimido[5',4':4,5]pyrrolo[2,1-c][1,4]oxazin-4-yl)-4-(trifluoromethyl)pyrimidin-2-amine |
| 63 | 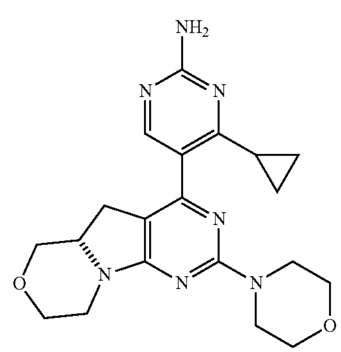 [SMILES: Nc1ncc(-c2nc(N3CCOCC3)nc3c2C[C@H]2COCCN32)c(C2CC2)n1] | (S)-4-cyclopropyl-5-(2-morpholino-5a,6,8,9-tetrahydro-5H-pyrimido[5',4':4,5]pyrrolo[2,1-c][1,4]oxazin-4-yl)pyrimidin-2-amine |

| Cpd No. | Structure | Name |
|---|---|---|
| 64 | 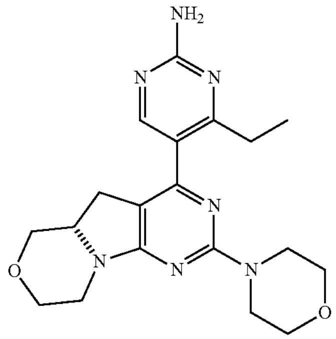 [SMILES: CCc1nc(N)ncc1-c1nc(N2CCOCC2)nc2c1C[C@H]1COCCN21] | (S)-4-ethyl-5-(2-morpholino-5a,6,8,9-tetrahydro-5H-pyrimido[5',4':4,5]pyrrolo[2,1-c][1,4]oxazin-4-yl)pyrimidin-2-amine |

Table 5 gives the structures and the corresponding IUPAC names (using ChemDraw Ultra, Version 13.0.1 as well as lower and upper software versions thereof, CambridgeSoft Corp., Cambridge Mass.) of exemplary compounds (Cpd) Nos. 65-77 of formula (Ia).

| Cpd No. | Structure | Name |
|---|---|---|
| 65 | 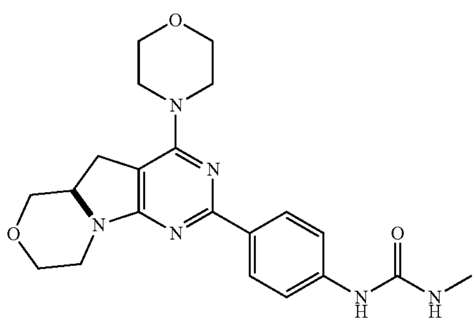 | (R)-1-methyl-3-(4-(4-morpholino-5a,6,8,9-tetrahydro-5H-pyrimido[5',4':4,5]pyrrolo[2,1-c][1,4]oxazin-2-yl)phenyl)urea |
| 66 | 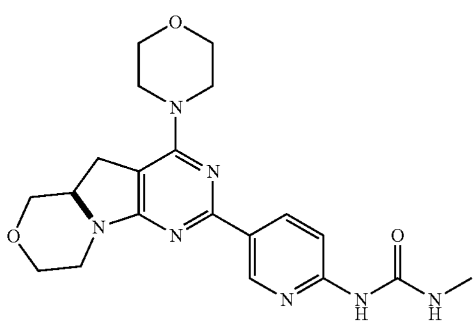 | (R)-1-methyl-3-(5-(4-morpholino-5a,6,8,9-tetrahydro-5H-pyrimido[5',4':4,5]pyrrolo[2,1-c][1,4]oxazin-2-yl)pyridin-2-yl)urea |
| 67 | 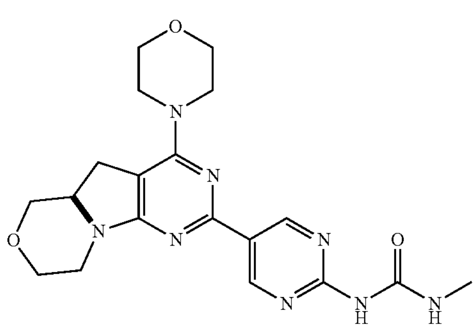 [SMILES: CNC(=O)Nc1ccc(-c2nc(N3CCOCC3)c3c(n2)N2CCOC[C@H]2C3)cn1] | (R)-1-methyl-3-(5-(4-morpholino-5a,6,8,9-tetrahydro-5H-pyrimido[5',4':4,5]pyrrolo[2,1-c][1,4]oxazin-2-yl)pyrimidin-2-yl)urea |

-continued

| Cpd No. | Structure | Name |
|---|---|---|
| 68 | 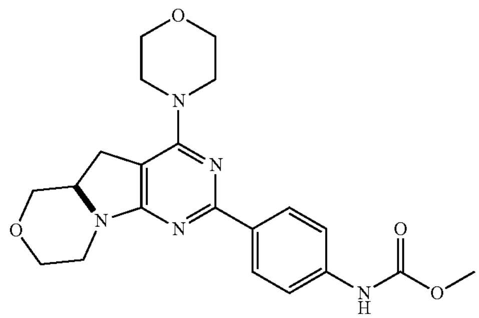 [SMILES: COC(=O)Nc1ccc(-c2nc(N3CCOCC3)c3c(n2)N2CCOC[C@H]2C3)cc1] | methyl (R)-(4-(4-morpholino-5a,6,8,9-tetrahydro-5H-pyrimido[5',4':4,5]pyrrolo[2,1-c][1,4]oxazin-2-yl)phenyl)carbamate |
| 69 | 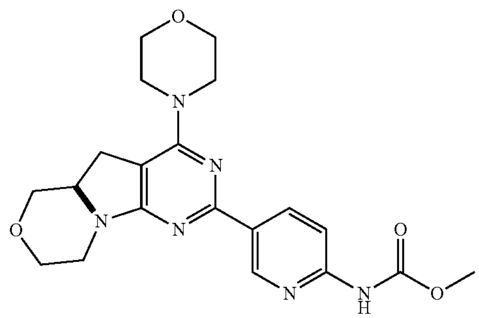 [SMILES: COC(=O)Nc1ccc(-c2nc(N3CCOCC3)c3c(n2)N2CCOC[C@H]2C3)cn1] | methyl (R)-(5-(4-morpholino-5a,6,8,9-tetrahydro-5H-pyrimido[5',4':4,5]pyrrolo[2,1-c][1,4]oxazin-2-yl)pyridin-2-yl)carbamate |
| 70 | 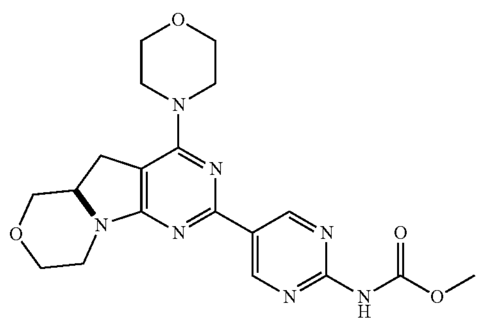 [SMILES: COC(=O)Nc1ncc(-c2nc(N3CCOCC3)c3c(n2)N2CCOC[C@H]2C3)cn1] | methyl (R)-(5-(4-morpholino-5a,6,8,9-tetrahydro-5H-pyrimido[5',4':4,5]pyrrolo[2,1-c][1,4]oxazin-2-yl)pyrimidin-2-yl)carbamate |
| 71 | 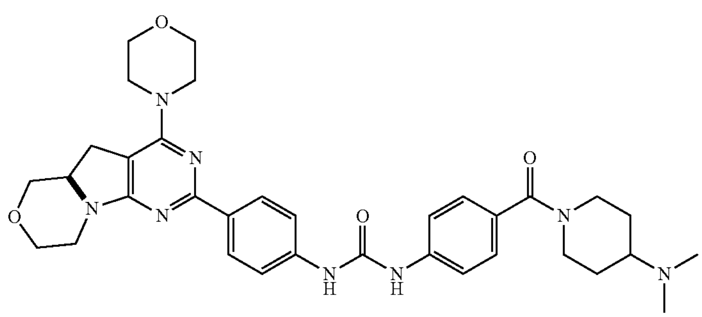 [SMILES: CN(C)C1CCN(C(=O)c2ccc(NC(=O)Nc3ccc(-c4nc(N5CCOCC5)c5c(n4)N4CCOC[C@H]4C5)cc3)cc2)CC1] | (R)-1-(4-(4-(dimethylamino)piperidine-1-carbonyl)phenyl)-3-(4-(4-morpholino-5a,6,8,9-tetrahydro-5H-pyrimido[5',4':4,5]pyrrolo[2,1-c][1,4]oxazin-2-yl)phenyl)urea |
| 72 | 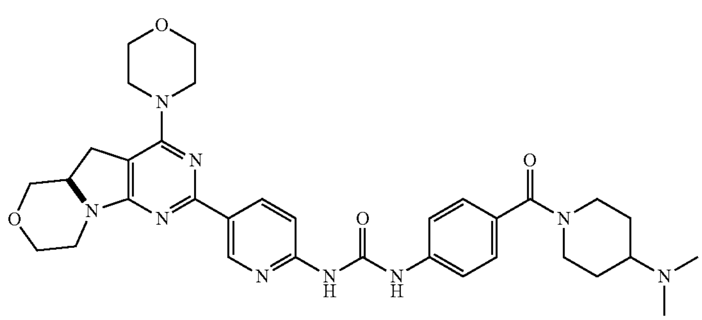 | (R)-1-(4-(4-(dimethylamino)piperidine-1-carbonyl)phenyl)-3-(5-(4-morpholino-5a,6,8,9-tetrahydro-5H-pyrimido[5',4':4,5]pyrrolo[2,1-c][1,4]oxazin-2-yl)pyridin-2-yl)urea |

| Cpd No. | Structure | Name |
|---|---|---|
| 73 | 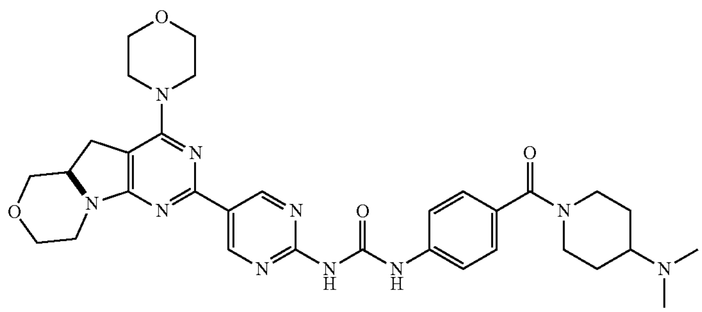 [SMILES: CN(C)C1CCN(C(=O)c2ccc(NC(=O)Nc3ccc(-c4nc(N5CCOCC5)c5c(n4)N4CCOC[C@H]4C5)cn3)cc2)CC1] | (R)-1-(4-(4-(dimethylamino)piperidine-1-carbonyl)phenyl)-3-(5-(4-morpholino-5a,6,8,9-tetrahydro-5H-pyrimido[5',4':4,5]pyrrolo[2,1-c][1,4]oxazin-2-yl)pyrimidin-2-yl)urea |
| 74 | 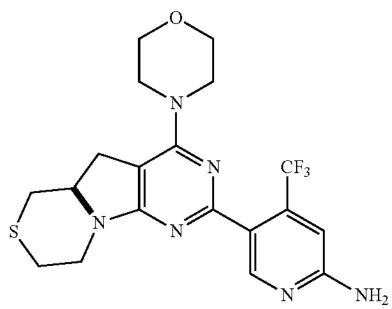 [SMILES: Nc1cc(C(F)(F)F)c(-c2nc(N3CCOCC3)c3c(n2)N2CCSC[C@H]2C3)cn1] | (R)-5-(4-morpholino-5a,6,8,9-tetrahydro-5H-pyrimido[5',4':4,5]pyrrolo[2,1-c][1,4]thiazin-2-yl)-4-(trifluoromethyl)pyridin-2-amine |
| 75 | 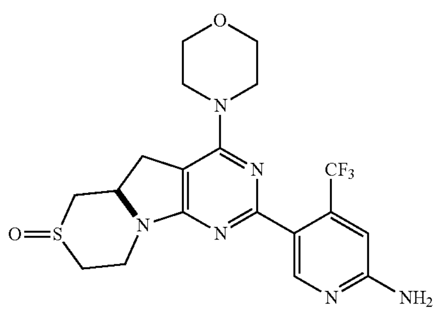 | (5aR)-2-(6-amino-4-(trifluoromethyl)pyridin-3-yl)-4-morpholino-5a,6,8,9-tetrahydro-5H-pyrimido[5',4':4,5]pyrrolo[2,1-c][1,4]thiazine 7-oxide |
| 76 | 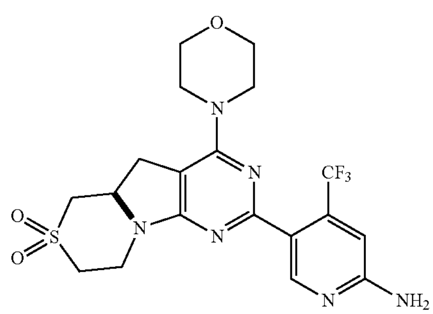 [SMILES: Nc1cc(C(F)(F)F)c(-c2nc(N3CCOCC3)c3c(n2)N2CCS(=O)(=O)C[C@H]2C3)cn1] | (R)-2-(6-amino-4-(trifluoromethyl)pyridin-3-yl)-4-morpholino-5a,6,8,9-tetrahydro-5H-pyrimido[5',4':4,5]pyrrolo[2,1-c][1,4]thiazine 7,7-dioxide |
| 77 | 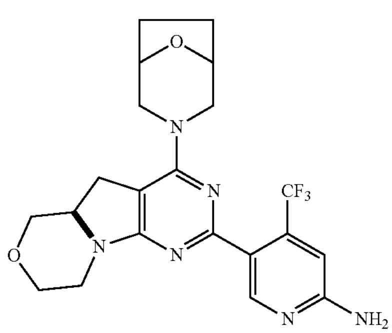 [SMILES: Nc1cc(C(F)(F)F)c(-c2nc(N3CC4CCC(C3)O4)c3c(n2)N2CCOC[C@H]2C3)cn1] | 5-((5aR)-4-(8-oxa-3-azabicyclo[3.2.1]octan-3-yl)-5a,6,8,9-tetrahydro-5H-pyrimido[5',4':4,5]pyrrolo[2,1-c][1,4]oxazin-2-yl)-4-(trifluoromethyl)pyridin-2-amine |

Table 6 gives the structures and the corresponding IUPAC names (using ChemDraw Ultra, Version 13.0.1 as well as lower and upper software versions thereof, CambridgeSoft Corp., Cambridge Mass.) of exemplary compounds (Cpd) Nos. 78-90 of formula (Ib).

| Cpd No. | Structure | Name |
|---|---|---|
| 78 | 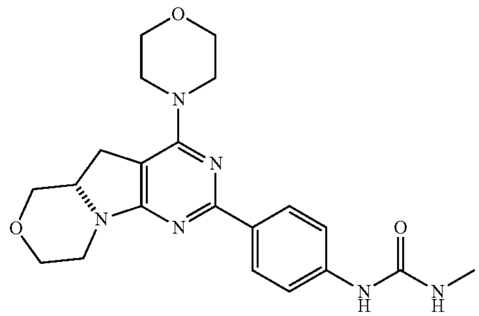 | (S)-1-methyl-3-(4-(4-morpholino-5a,6,8,9-tetrahydro-5H-pyrimido[5',4':4,5]pyrrolo[2,1-c][1,4]oxazin-2-yl)phenyl)urea |
| 79 | 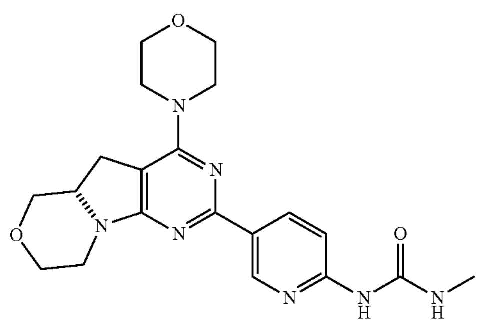 [SMILES: CNC(=O)Nc1ccc(-c2nc(N3CCOCC3)c3c(n2)N2CCOC[C@@H]2C3)cn1] | (S)-1-methyl-3-(5-(4-morpholino-5a,6,8,9-tetrahydro-5H-pyrimido[5',4':4,5]pyrrolo[2,1-c][1,4]oxazin-2-yl)pyridin-2-yl)urea |
| 80 | 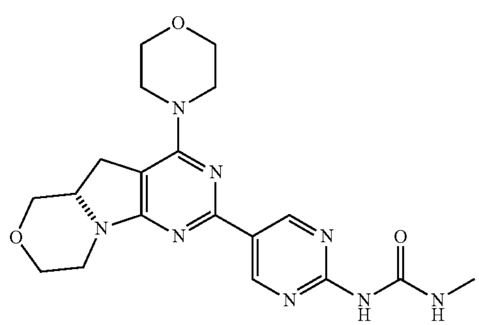 | (S)-1-methyl-3-(5-(4-morpholino-5a,6,8,9-tetrahydro-5H-pyrimido[5',4':4,5]pyrrolo[2,1-c][1,4]oxazin-2-yl)pyrimidin-2-yl)urea |
| 81 | 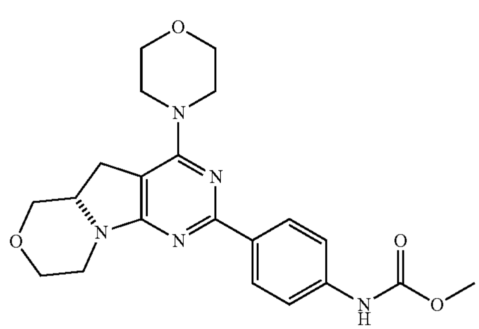 [SMILES: COC(=O)Nc1ccc(-c2nc(N3CCOCC3)c3c(n2)N2CCOC[C@@H]2C3)cc1] | methyl (S)-(4-(4-morpholino-5a,6,8,9-tetrahydro-5H-pyrimido[5',4':4,5]pyrrolo[2,1-c][1,4]oxazin-2-yl)phenyl)carbamate |

-continued

| Cpd No. | Structure | Name |
|---|---|---|
| 82 | 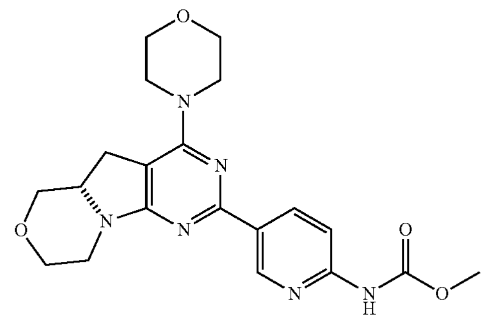 | methyl (S)-(5-(4-morpholino-5a,6,8,9-tetrahydro-5H-pyrimido[5',4':4,5]pyrrolo[2,1-c][1,4]oxazin-2-yl)pyridin-2-yl)carbamate |
| 83 | 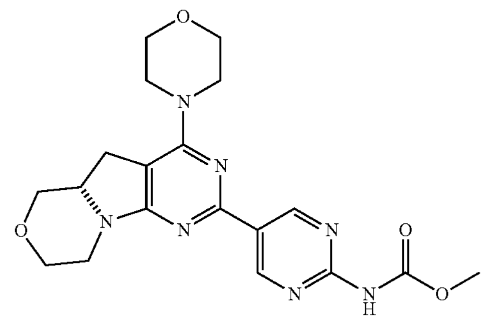 [SMILES: COC(=O)Nc1ncc(-c2nc(N3CCOCC3)c3c(n2)N2CCOC[C@@H]2C3)cn1] | methyl (S)-(5-(4-morpholino-5a,6,8,9-tetrahydro-5H-pyrimido[5',4':4,5]pyrrolo[2,1-c][1,4]oxazin-2-yl)pyrimidin-2-yl)carbamate |
| 84 | 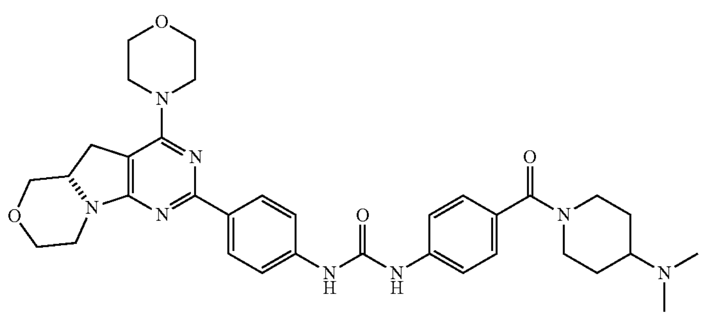 [SMILES: CN(C)C1CCN(C(=O)c2ccc(NC(=O)Nc3ccc(-c4nc(N5CCOCC5)c5c(n4)N4CCOC[C@@H]4C5)cc3)cc2)CC1] | (S)-1-(4-(4-(dimethylamino)piperidine-1-carbonyl)phenyl)-3-(4-(4-morpholino-5a,6,8,9-tetrahydro-5H-pyrimido[5',4':4,5]pyrrolo[2,1-c][1,4]oxazin-2-yl)phenyl)urea |
| 85 | 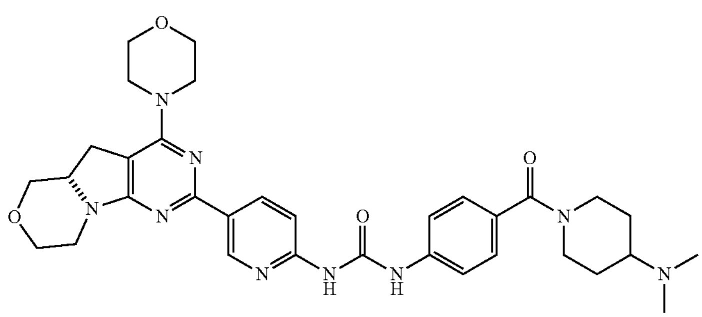 [SMILES: CN(C)C1CCN(C(=O)c2ccc(NC(=O)Nc3ccc(-c4nc(N5CCOCC5)c5c(n4)N4CCOC[C@@H]4C5)cn3)cc2)CC1] | (S)-1-(4-(4-(dimethylamino)piperidine-1-carbonyl)phenyl)-3-(5-(4-morpholino-5a,6,8,9-tetrahydro-5H-pyrimido[5',4':4,5]pyrrolo[2,1-c][1,4]oxazin-2-yl)pyridin-2-yl)urea |
| 86 | 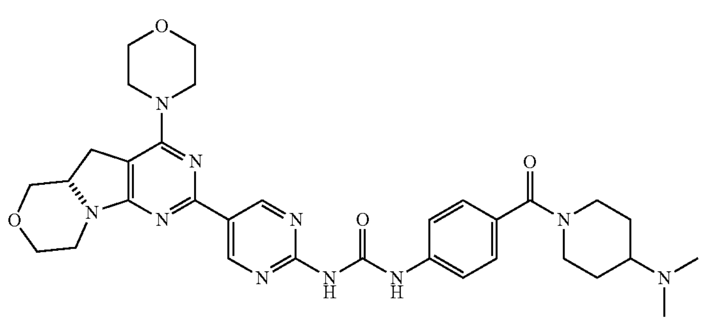 [SMILES: CN(C)C1CCN(C(=O)c2ccc(NC(=O)Nc3ncc(-c4nc(N5CCOCC5)c5c(n4)N4CCOC[C@@H]4C5)cn3)cc2)CC1] | (S)-1-(4-(4-(dimethylamino)piperidine-1-carbonyl)phenyl)-3-(5-(4-morpholino-5a,6,8,9-tetrahydro-5H-pyrimido[5',4':4,5]pyrrolo[2,1-c][1,4]oxazin-2-yl)pyrimidin-2-yl)urea |

| Cpd No. | Structure | Name |
|---|---|---|
| 87 | 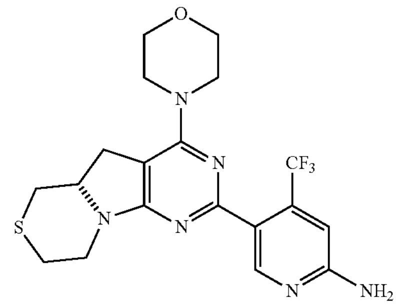 [SMILES: Nc1cc(C(F)(F)F)c(-c2nc(N3CCOCC3)c3c(n2)N2CCSC[C@@H]2C3)cn1] | (S)-5-(4-morpholino-5a,6,8,9-tetrahydro-5H-pyrimido[5',4':4,5]pyrrolo[2,1-c][1,4]thiazin-2-yl)-4-(trifluoromethyl)pyridin-2-amine |
| 88 | 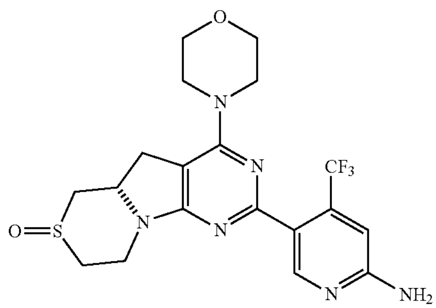 | (5aS)-2-(6-amino-4-(trifluoromethyl)pyridin-3-yl)-4-morpholino-5a,6,8,9-tetrahydro-5H-pyrimido[5',4':4,5]pyrrolo[2,1-c][1,4]thiazine 7-oxide |
| 89 | 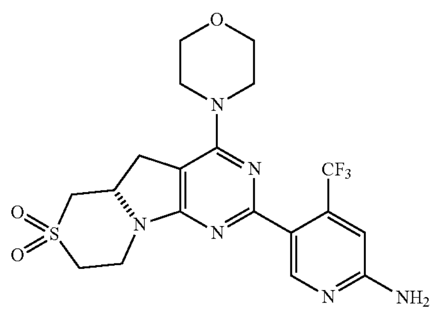 [SMILES: Nc1cc(C(F)(F)F)c(-c2nc(N3CCOCC3)c3c(n2)N2CCS(=O)(=O)C[C@@H]2C3)cn1] | (S)-2-(6-amino-4-(trifluoromethyl)pyridin-3-yl)-4-morpholino-5a,6,8,9-tetrahydro-5H-pyrimido[5',4':4,5]pyrrolo[2,1-c][1,4]thiazine 7,7-dioxide |
| 90 | 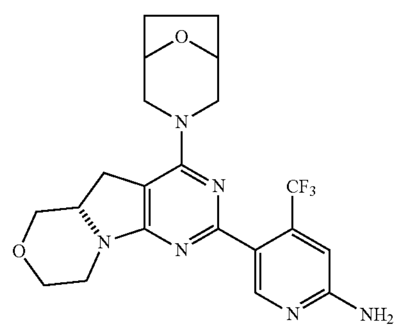 [SMILES: Nc1cc(C(F)(F)F)c(-c2nc(N3CC4CCC(C3)O4)c3c(n2)N2CCOC[C@@H]2C3)cn1] | 5-((5aS)-4-(8-oxa-3-azabicyclo[3.2.1]octan-3-yl)-5a,6,8,9-tetrahydro-5H-pyrimido[5',4':4,5]pyrrolo[2,1-c][1,4]oxazin-2-yl)-4-(trifluoromethyl)pyridin-2-amine |

Preparation of Compounds of the Invention

The compounds of the invention may be synthesized by synthetic routes that include processes analogous to those well known in the chemical arts, particularly in light of the description contained herein. The starting materials are generally available from commercial sources such as Aldrich Chemicals or are readily prepared using methods well known to those skilled in the art (e.g., prepared by methods generally described in Louis F. Fieser and Mary Fieser, Reagents for Organic Synthesis, v. 1-19, Wiley, N.Y. (1967-1999 ed.), or Beilsteins Handbuch der organischen Chemie, 4. Aufl. ed. Springer-Verlag, Berlin, including supplements (also available via the Beilstein online database). In certain embodiments, the compounds of the invention may be readily prepared using procedures well-known to prepare pyrimidines and other heterocycles, which are described in: Comprehensive Heterocyclic Chemistry, Editors Katritzky and Rees, Pergamon Press, 1984.

Compounds of the invention may be prepared singly or as compound libraries comprising at least 2, for example 5 to 1,000 compounds, or 10 to 100 compounds. Libraries of compounds of the invention may be prepared by a combinatorial 'split and mix' approach or by multiple parallel syntheses using either solution phase or solid phase chemistry, by procedures well known to those skilled in the art. Thus according to a further aspect of the invention there is provided a compound library comprising at least 2 compounds, or pharmaceutically acceptable salts thereof.

For illustrative purposes, Schemes 1-6 show general methods for preparing the compounds of the present invention as well as key intermediates. For a more detailed description of the individual reaction steps, see the Examples herein below. Those skilled in the art will appreciate that other synthetic routes may be used to synthesize the compounds of the invention. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In preparing compounds of the invention, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Scheme 1

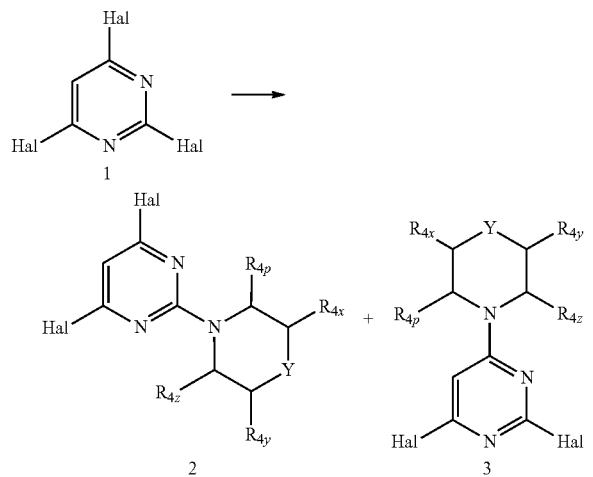

Scheme 1 shows a general method for preparation of the pyrimidine intermediates 2 and 3 from 2,4,6-trihalo-1,3,5-pyrimidine reagent (1), wherein Hal is Cl, Br, or I; and Y, $R_{4p}$, $R_{4x}$, $R_{4y}$, and $R_{4z}$ are as defined above.

Scheme 2

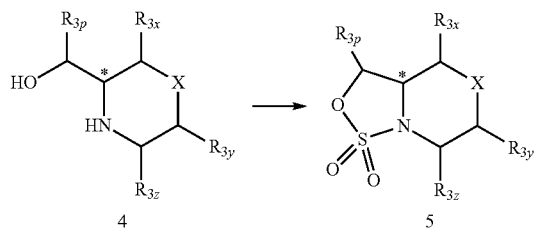

Scheme 2 shows a general method for preparation of sulfamidate intermediate 5 from (R) or (S) functionalized 3-hydroxymethyl morpholine (4).

Scheme 3

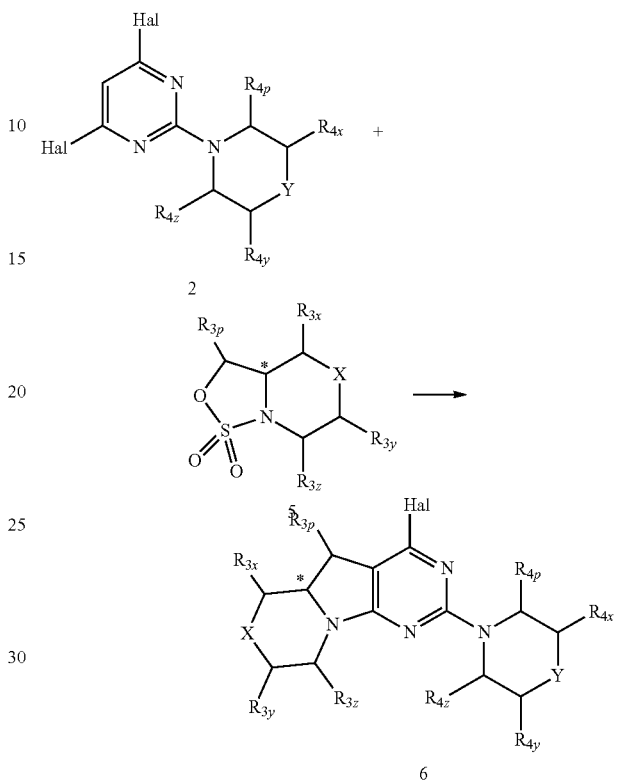

Scheme 3 shows a general method for preparation of fused morpholino pyrimidine 6 from intermediate 2.

Scheme 4

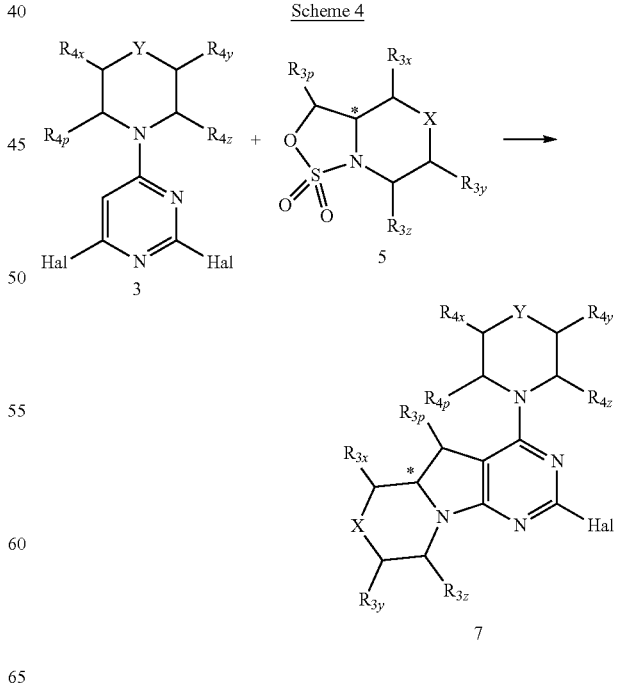

Scheme 4 shows a general method for preparation of fused morpholino pyrimidine 7 from intermediate 3.

Scheme 5

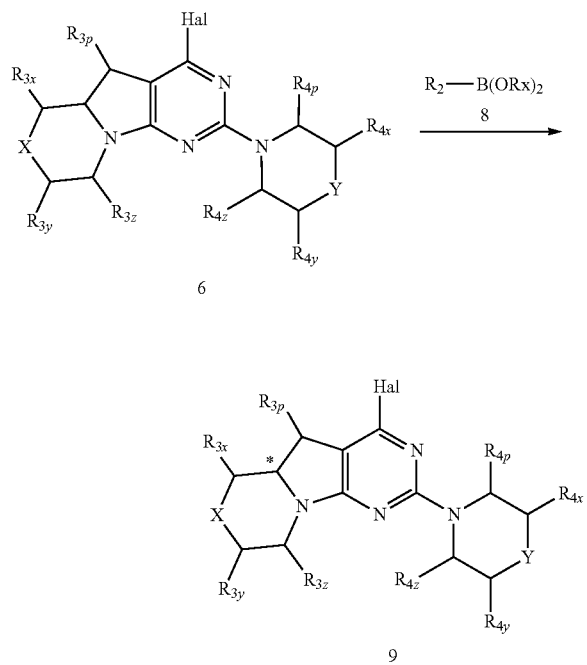

Scheme 5 shows a general method for Suzuki-type coupling of a 4-halo pyrimidine intermediate 6 with a cyclic heteroaryl boronate acid (Rx=H) or ester (Rx=alkyl) reagent 8 to prepare the cyclic heteroaryl ($R_1$) compounds (9) of formula Ia-Ib, wherein Hal is Cl, Br, or I; and R2 residues are as defined for formula Ia-Ib compounds, or precursors thereto. For reviews of the Suzuki reaction, see: Miyaura et al. (1995) Chem. Rev. 95:2457-2483; Suzuki, A. (1999) J. Organomet. Chem. 576:147-168; The palladium catalyst may be any that is typically used for Suzuki-type cross-couplings, such as $PdCl_2(PPh_3)_2$, $Pd(PPh_3)_4$, $Pd(OAc)_2$, $PdCl_2(dppf)$-DCM, $Pd_2(dba)_3$/Pt-Bu)$_3$ (Owens et al. (2003), Bioorganic & Med. Chem. Letters 13:4143-4145; Molander et al. (2002), Organic Letters 4(11):1867-1870; U.S. Pat. No. 6,448,433).

Scheme 6

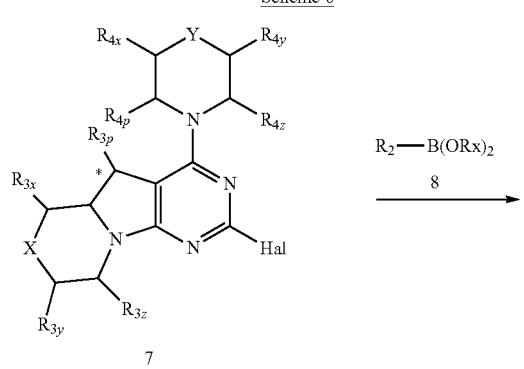

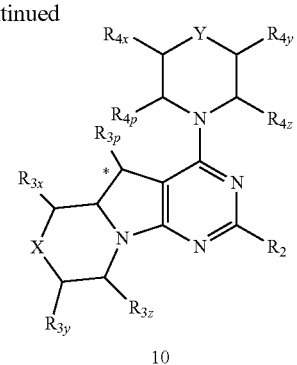

Scheme 6 shows a general method for Suzuki-type coupling of a 2-halo morpholino pyrimidine intermediate 7 with a cyclic heteroaryl boronate acid (Rx=H) or ester (Rx=alkyl) reagent 8 to prepare the cyclic heteroaryl ($R_1$) compounds (10) of formula IIa-IIb, wherein Hal is Cl, Br, or I; and $R_1$ residues are as defined for formula II compounds, or precursors thereto.

Methods of Separation

In the methods of preparing the compounds of this invention, it may be advantageous to separate reaction products from one another and/or from starting materials. The desired products of each step or series of steps are separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved, for example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-trifluoromethyl)phenyl acetate (Jacob III, J. Org. Chem. (1982) 47:4165), of the racemic mixture, and analyzing the $^1$H NMR spectrum for the presence of the two atropisomeric enantiomers or diastereomers.

Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990), 513:375-378). Enriched or purified enantiomers can be distinguished by methods used to distinguish other chiral molecules with asymmetric carbon atoms, such as optical rotation and circular dichroism.

EXAMPLES

The chemical reactions described in the Examples may be readily adapted to prepare a number of other lipid kinase inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the Examples described below, unless otherwise indicated, all temperatures are set forth in degrees Celsius (° C.). Reagents were purchased from commercial suppliers such as Aldrich Chemical Company, Fluorochem, Acros, Lancaster, TCI or Maybridge, and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Column chromatography was conducted by using Merck silica gel. $^1$H NMR spectra were recorded on a Bruker instrument operating at 400 MHz, 500 MHz and 600 MHz. $^1$H NMR spectra were obtained in deuterated CDCl$_3$, D$_6$-DMSO, CD$_3$OD or D$_6$-acetone solutions (reported in ppm), using chloroform as the reference standard (7.25 ppm) or TMS (0 ppm). When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Abbreviations: h (hours), min (minutes), s (seconds), FC (flash chromatography), rt (room temperature), DCM (dichloromethane), ACN (acetonitrile), DMF (dimethylformamide), EtOAc (ethyl acetate), EtOH (ethanol), Cycl (cyclohexane), MeOH (methanol), THF (tetrahydrofuran), DIPEA (N, N-diisopropylethylamine).

Example 1

4-(4,6-Dichloropyrimidin-2-yl)morpholine and 4-(2,6-dichloropyrimidin-4-yl)morpholine

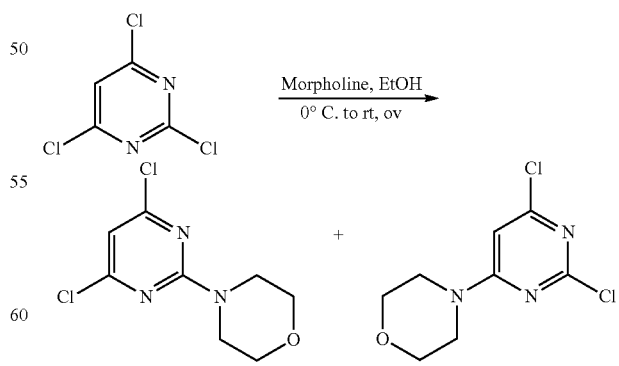

A solution of morpholine (22.4 mL, 512.4 mmol, 4.2 eq) in EtOH (100 mL) is added dropwise to a cooled (0° C.) solution of 2,4,6-trichloropyrimidine (14 mL, 122 mmol, 1 eq) in EtOH (200 mL). The mixture is stirred at rt overnight.

The crude mixture is poured onto a saturated solution of NaHSO₄ (1 L), and the resulting precipitate is collected by filtration. The solid is redissolved in a minimal amount of DCM and adsorbed on silica gel. FC (AcOEt/Cycl 1:3→1:1) gives the desired compounds 4-(4,6-Dichloropyrimidin-2-yl)morpholine (20% yield) and 4-(2,6-dichloropyrimidin-4-yl)morpholine (65% yield).

4-(4,6-Dichloropyrimidin-2-yl)morpholine

¹H NMR (400 MHz, CDCl₃): δ 6.53 (s, 1H), 3.77 (m, 4H), 3.71 (m, 4H). ¹³C NMR (100.6 MHz, CDCl₃): δ 161.6, 160.4, 108.2, 66.5, 44.3.

4-(2,6-dichloropyrimidin-4-yl)morpholine

¹H NMR (400 MHz, CDCl₃): δ 6.34 (s, 1H), 3.70 (m, 4H), 3.58 (m, 4H). ¹³C NMR (100.6 MHz, CDCl₃): δ 162.9, 160.3, 159.5, 99.6, 66.9, 44.3.

Example 2

(R)-Tetrahydro-3H-[1,2,3]oxathiazolo[4,3-c][1,4]oxazine 1,1-dioxide

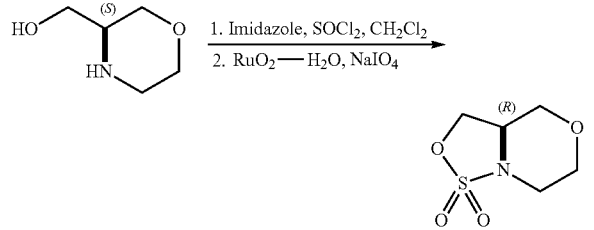

A solution of SOCl₂ (0.82 mL, 11.3 mmol) in DCM (0.8 mL) is added dropwise to a cooled (−5° C.) solution of imidazole (2.38 g, 34.9 mmol) in DCM (15 mL), and the temperature kept at −5° C. The cooling bath is removed and the reaction mixture is stirred over 45 min while allowing it to warm up to rt. The mixture is cooled down to −10° C. A solution of (S)-morpholin-3-ylmethanol (0.68 g, 5.8 mmol) in DCM (5.8 mL) is added dropwise while keeping the temperature around −10° C. The mixture is stirred at −5° C. for 2 h, and then at +5° C. for 1 h. Water (15 mL) is added and the layers are separated. The organic layer is washed with half concentrated brine (15 mL), and cooled to 0° C. A solution of NaIO₄ (3.73 g, 17.4 mmol) in water (40 mL) is added, followed by Ru₂O—H₂O (8 mg). The bath is removed after 15 min and the dark reaction mixture stirred overnight. The layers are separated and the organic layer is filtered through a silica gel column eluting with excess DCM until no more product is observed by TLC.

The corresponding (S) enantiomer is synthesized in the same manner.

¹H NMR (400 MHz, CDCl₃) δ 4.71-4.51 (m, 1H), 4.30 (m, 1H), 4.02 (dd, J=11.6, 3.4 Hz, 1H), 3.94-3.68 (m, 3H), 3.61 (dd, J=11.6, 7.8 Hz, 1H), 3.37 (0, J=12.1, 3.6 Hz, 1H), 3.24-3.07 (m, 1H).

R enantiomer: [α_D]=−42.8 (CHCl₃, c=0.65)
S enantiomer: [α_D]=+53.8 (CHCl₃, c=0.75)

Example 3

(S)-2-Chloro-4-morpholino-5a,6,8,9-tetrahydro-5H-pyrimido[5',4':4,5]pyrrolo[2,1-c][1,4]oxazine

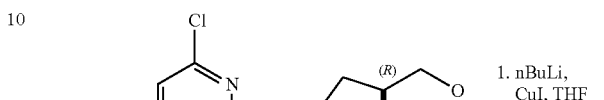

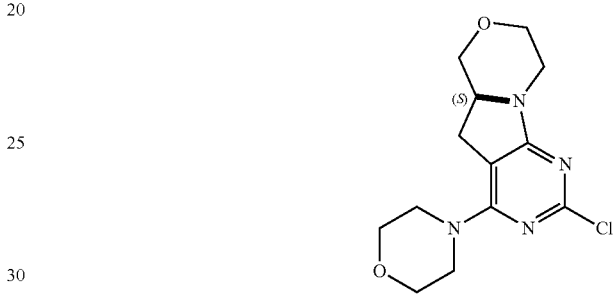

A 1.6 M n-BuLi solution (1.4 mL) is cooled down to −78° C., and a solution of 4-(2,6-dichloropyrimidin-4-yl)morpholine (435 mg, 1.86 mmol) in THF (5 mL) is added dropwise. The mixture is stirred at −78° C. for 35 min. CuI (14 mg, 0.07 mmol) and a solution of (R)-tetrahydro-3H-[1,2,3]oxathiazolo[4,3-c][1,4]oxazine 1,1-dioxide (333 mg, 1.86 mmol) in THF (3 mL) is added. The mixture is stirred at −78° C. and then allowed to warm to rt, then stirred for 16 h. The reaction is quenched by addition of water (1 mL). 15% HCl (10 mL) and methanol (5 mL) are added, and the mixture heated to 60° C. for 5 h. The organic solvents are removed by rotary evaporation and the remaining aqueous layer diluted with 2 M NaOH (5 mL). NaOH pellets are used to adjust the pH to 11. AcOEt (10 mL) is added and the mixture stirred for 30 minutes. The layers are separated and the aqueous layer extracted with AcOEt (2×10 mL). The combined organic layers are dried over sodium sulfate, filtered and concentrated. The product is precipitated as a brown solid (530 mg, 96%), and is used without any further purification.

The corresponding (R) enantiomer is synthesized in the same manner.

¹H NMR (400 MHz, CDCl₃) δ 4.01 (dd, J=13.6, 2.8 Hz, 1H), 3.97-3.85 (m, 1H), 3.75 (m, 2H), 3.66 (m, 4H), 3.61-3.47 (m, 4H), 3.38 (td, J=11.7, 2.9 Hz, 1H), 3.23 (t, J=11.0 Hz, 1H), 3.19-3.04 (m, 2H), 2.50 (dd, J=15.0, 5.1 Hz, 1H).

R enantiomer: [α_D]=−3.3 (CHCl₃, c=1.5)
S enantiomer: [α_D]=+4.0 (CHCl₃, c=1.2)

Example 4

(R)-5-(4-Morpholino-5a,6,8,9-tetrahydro-5H-pyrimido[5',4':4,5]pyrrolo[2,1-c][1,4]oxazin-2-yl)-4-(trifluoromethyl)pyridin-2-amine

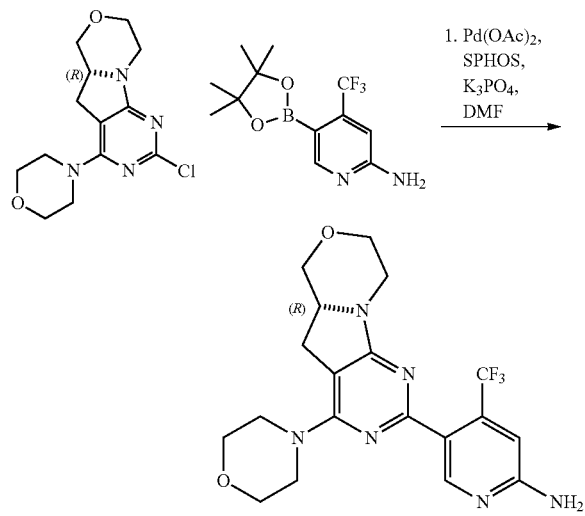

The pyrimidine (147 mg, 0.495 mmol), boronate (255 mg, 0.74 mmol), K$_3$PO$_4$ (250 mg, 1.18 mmol), SPHOS (25 mg, 0.06 mmol) and Pd(OAc)$_2$ (7 mg, 0.03 mmol) are placed into a round bottom flask under nitrogen. DMF (3 mL) is added, and nitrogen bubbled through the mixture for 15 min. The reaction mixture is heated to 100° C. for 18 h, cooled to rt, diluted with AcOEt (10 mL) and poured into saturated NH$_4$Cl (10 mL). The layers are separated and the aqueous layer extracted with AcOEt (2×10 mL). The combined organic layers are dried over sodium sulfate, filtered and concentrated. The crude mixture is purified by column chromatography (1:1→1:3→0:1 Cycl: AcOEt). The product is obtained as a solid (77 mg, 37%).

The corresponding (S) enantiomer is synthesized in the same manner.

$^1$H NMR (400 MHz, CDCl$_3$) δ 8.63 (s, 1H), 6.77 (s, 1H), 4.76 (s, 2H), 4.17-4.05 (m, 1H), 4.03-3.89 (m, 1H), 3.87-3.72 (m, 6H), 3.72-3.56 (m, 6H), 3.47 (td, J=11.7, 2.9 Hz, 1H), 3.35 (t, J=11.0 Hz, 1H), 3.31-3.11 (m, 2H), 2.62 (dd, J=15.0, 4.9 Hz, 1H).

R enantiomer: [α$_D$]=+13.5 (CHCl$_3$, c=1.6)
S enantiomer: [α$_D$]=−13.2 (CHCl$_3$, c=2.0)

Example 5

(S)-4-chloro-2-morpholino-5a,6,8,9-tetrahydro-5H-pyrimido[5',4':4,5]pyrrolo[2,1-c][1,4]oxazine

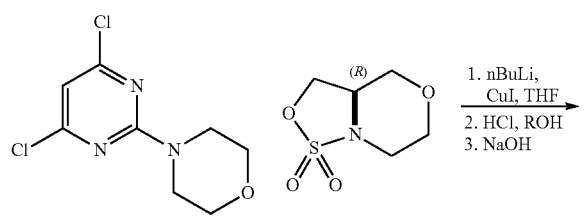

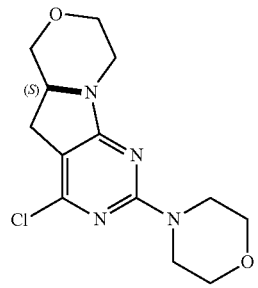

n-BuLi (1.6 M, 1 mL) and THF (1 mL) are placed into a dry round bottom flask under nitrogen and cooled to −78° C. A solution of the pyrimidine (298 mg, 1.27 mmol) in THF (3.5 mL) is slowly added, and the reaction mixture stirred at −78° C. for 30 min. CuI (12 mg, 0.06 mmol) and a solution of sulfamidate (228 mg, 1.27 mmol) in THF (2 mL) are added. The mixture is stirred at −78° C. for 15 min and then allowed to warm up to rt and stirred over 16 h. The reaction mixture is quenched by addition of water (0.5 mL). A solution of 12 M HCl (5 mLl) and EtOH (5 mL) is added, and the mixture heated to 70° C. for 1.5 h. The organic solvents are removed, the residue diluted with 2 M NaOH, and solid NaOH added to adjust the pH to 11. The mixtures is diluted with ethyl acetate and stirred at rt over 1.5 h. The solvent is removed, and the residue re-dissolved in EtOH (7 mL) and acidified with 12 M HCl until pH 1, then stirred at rt over 18 h. The mixture is cooled down, and NaOH is slowly added until pH 11, then stirred over 2 h and diluted with AcOEt. The layers are separated, and the aqueous layer extracted with AcOEt (2×15 mL). The combined organic layers are dried over sodium sulfate, and purified by FC (2:1→1:1 cycl: AcOEt). The desired product is obtained as a white solid (286 mg, 76%).

The corresponding (R) enantiomer is synthesized in the same manner.

$^1$H NMR (400 MHz, CDCl$_3$) δ 4.04-3.90 (m, 2H), 3.87 (dt, J=11.3, 4.4 Hz, 2H), 3.79-3.65 (m, 8H), 3.44 (td, J=11.7, 2.9 Hz, 1H), 3.32-3.14 (m, 2H), 2.99 (dd, J=16.1, 9.4 Hz, 1H), 2.42 (dd, J=16.1, 5.0 Hz, 1H).

R enantiomer: [α$_D$]=+56.2 (CHCl$_3$, c=1.4)
S enantiomer: [α$_D$]=−61.0 (CHCl$_3$, c=1.1)

Example 6

(R)-5-(2-Morpholino-5a,6,8,9-tetrahydro-5H-pyrimido[5',4':4,5]pyrrolo[2,1-c][1,4]oxazin-4-yl)-4-(trifluoromethyl)pyridin-2-amine

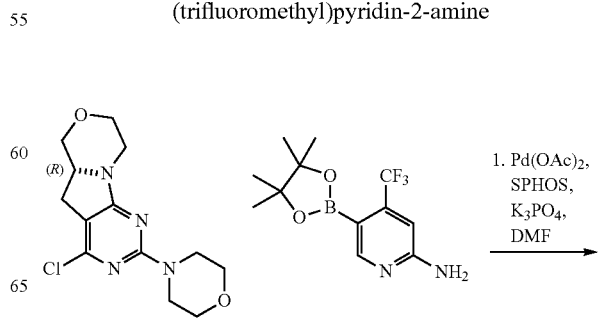

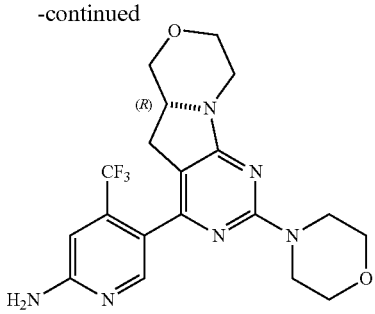

The pyrimidine (94 mg, 0.32 mmol), boronate (141 mg, 0.41 mmol), K$_3$PO$_4$ (134 mg, 0.64 mmol), SPHOS (14 mg, 0.035 mmol) and Pd(OAc)$_2$ (4 mg, 0.016 mmol) are placed into a round bottom flask. DMF (2 mL) is added, and the solution flushed with nitrogen for 10 min, then heated to 100° C. under nitrogen for 3 h. The mixtures is cooled to rt and diluted with AcOEt. Saturated NH$_4$Cl (10 mL) is added and the layers are separated. The aqueous layer is extracted with AcOEt (2×10 mL), dried over sodium sulfate, filtered, concentrated and purified by FC (1:1→1:3 Cycl: AcOEt→100% AcOEt→2% MeOH/AcOEt). The desired product is obtained as a solid (70 mg, 52% yield).

The corresponding (S) enantiomer is synthesized in the same manner.

$^1$H NMR (400 MHz, CDCl$_3$) δ 8.11 (s, 1H), 6.79 (s, 1H), 4.77 (s, 2H), 4.04 (dd, J=13.3, 2.9 Hz, 1H), 4.00-3.78 (m, 2H), 3.78-3.63 (m, 9H), 3.50 (td, J=11.6, 3.0 Hz, 1H), 3.36-3.12 (m, 2H), 2.91 (dd, J=15.8, 9.1 Hz, 1H), 2.32 (dd, J=15.8, 5.2 Hz, 1H).

R enantiomer: [α$_D$]=+20.5 (CHCl$_3$, c=1.5)
S enantiomer: [α$_D$]=−18.9 (CHCl$_3$, c=1.1)

Example 7

(R)-5-(2-Morpholino-5a,6,8,9-tetrahydro-5H-pyrimido[5',4':4,5]pyrrolo[2,1-c][1,4]oxazin-4-yl)pyrimidin-2-amine (R)-4-Chloro-2-morpholino-5a,6,8,9-tetrahydro-5H-pyrimido[5',4':4,5]pyrrolo[2,1-c][1,4]oxazine (40 mg, 0.135 mmol), 5-(4,4,5,5-tetramethyl-1,3,2-dioxaborolan-2-yl)-pyrimidin-2-amine (45 mg, 0.2 mmol), K$_3$PO$_4$ (57 mg, 0.27 mmol), XPhos-Pd-G2 (chloro(2-dicyclohexylphosphino-2',4',6'-triisopropyl-1,1'-biphenyl)[2-(2'-amino-1,1'-biphenyl)]palladium(II)) (5.3 mg, 0.007 mmol) are placed into a round bottom flask under nitrogen. Dioxane (3 mL) is added, followed by water (1.5 mL), and nitrogen bubbled through the mixture for 15 min. The reaction mixture is heated to 95° C. for 2 h, cooled to room temperature, diluted with AcOEt (10 mL) and poured into saturated NH$_4$Cl (10 mL). The layers are separated and the aqueous layer is extracted with AcOEt (2×10 mL). The combined organic layers are dried over sodium sulfate, filtered and concentrated. The crude mixture is purified by column chromatography (CH$_2$Cl$_2$/MeOH 20:1). The title compound is obtained as a solid (44 mg, 92%).

$^1$H NMR (400 MHz, D$_6$-DMSO) δ 8.73 (s, 2H), 7.01 (s, 2H), 3.97-3.90 (m, 2H), 3.81-3.75 (m, 2H), 3.66-3.63 (m, 8H), 3.31-3.11 (m, 4H), 2.67-2.62 (dd, J=16.0, 4.5 Hz, 1H).

$^{13}$C NMR (100 MHz, D$_6$-DMSO) δ 166.8, 163.3, 161.2, 157.3, 150.7, 120.3, 102.9, 70.2, 66.1, 65.6, 57.0, 44.3, 41.3, 27.3. MS (MALDI): 356 (M+H).

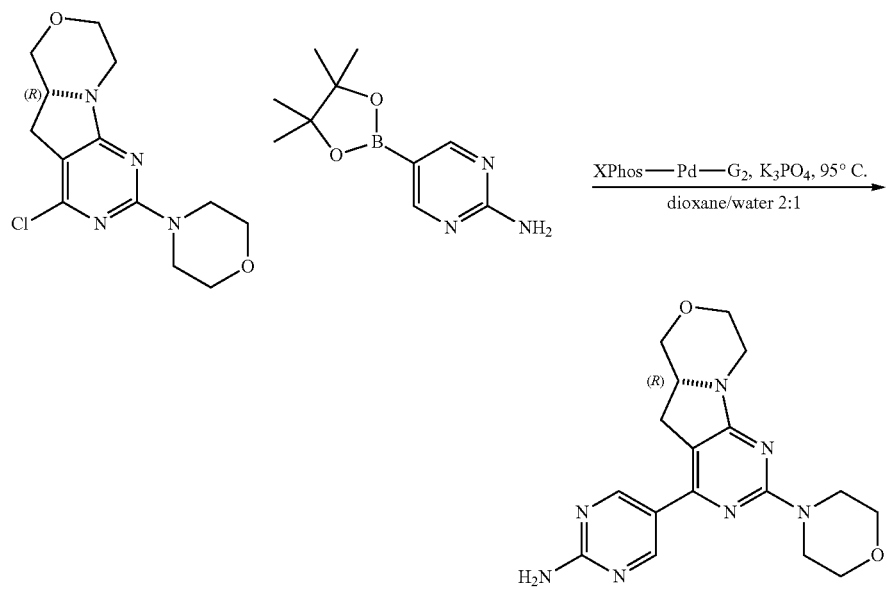

Example 8

(S)-5-(2-Morpholino-5a,6,8,9-tetrahydro-5H-pyrimido[5',4':4,5]pyrrolo[2,1-c][1,4]oxazin-4-yl)pyrimidin-2-amine

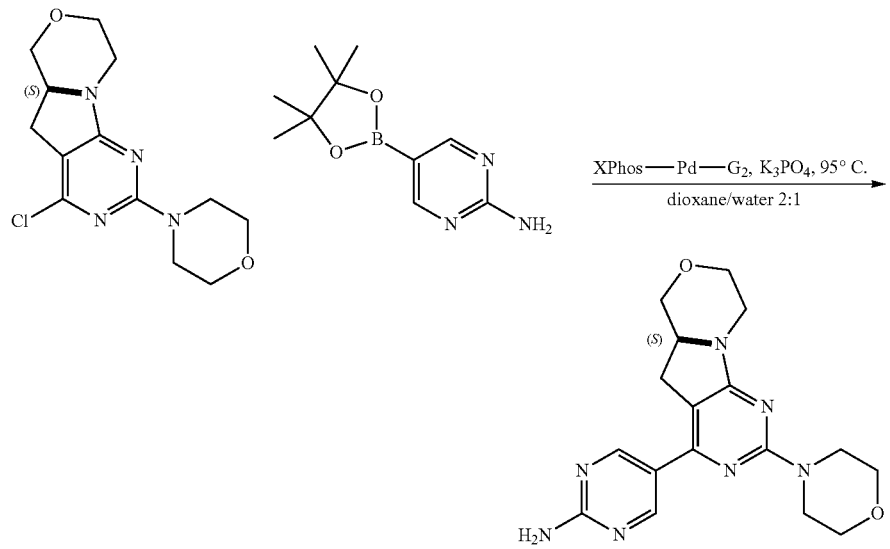

(S)-4-Chloro-2-morpholino-5a,6,8,9-tetrahydro-5H-pyrimido[5',4':4,5]pyrrolo[2,1-c][1,4]oxazine (40 mg, 0.135 mmol), 5-(4,4,5,5-tetramethyl-1,3,2-dioxaborolan-2-yl)-pyrimidin-2-amine (45 mg, 0.2 mmol), $K_3PO_4$ (57 mg, 0.27 mmol), XPhos-Pd-G2 (chloro(2-dicyclohexylphosphino-2',4',6'-triisopropyl-1,1'-biphenyl)[2-(2'-amino-1,1'-biphenyl)]palladium(II)) (5.3 mg, 0.007 mmol) are placed into a round bottom flask under nitrogen. Dioxane (3 mL) is added, followed by water (1.5 mL) and nitrogen bubbled through the mixture for 15 min. The reaction mixture is heated to 95° C. for 2 h, cooled to room temperature, diluted with AcOEt (10 mL) and poured into saturated $NH_4Cl$ (10 mL). The layers are separated and the aqueous layer is extracted with AcOEt (2×10 mL). The combined organic layers are dried over sodium sulfate, filtered and concentrated. The crude mixture is purified by column chromatography ($CH_2Cl_2$/MeOH 20:1). The title compound is obtained as a solid (42 mg, 88%).

$^1$H NMR (400 MHz, $D_6$-DMSO) δ 8.73 (s, 2H), 7.01 (s, 2H), 3.97-3.90 (m, 2H), 3.81-3.75 (m, 2H), 3.66-3.63 (m, 8H), 3.31-3.11 (m, 4H), 2.67-2.62 (dd, J=16.0, 4.5 Hz, 1H).
$^{13}$C NMR (100 MHz, $D_6$-DMSO) δ 166.8, 163.3, 161.2, 157.3, 150.7, 120.3, 102.9, 70.2, 66.1, 65.6, 57.0, 44.3, 41.3, 27.3. MS (MALDI): 356 (M+H).

Example 9

(R)-5-(4-Morpholino-5a,6,8,9-tetrahydro-5H-pyrimido[5',4':4,5]pyrrolo[2,1-c][1,4]oxazin-2-yl)pyrimidin-2-amine

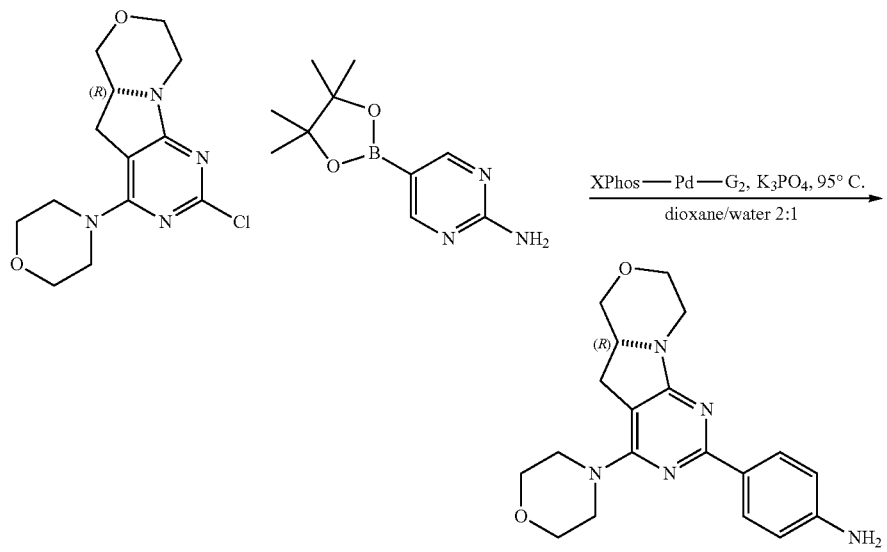

(R)-2-Chloro-4-morpholino-5a,6,8,9-tetrahydro-5H-pyrimido[5',4':4,5]pyrrolo[2,1-c][1,4]oxazine (40 mg, 0.135 mmol), 5-(4,4,5,5-tetramethyl-1,3,2-dioxaborolan-2-yl)-pyrimidin-2-amine (45 mg, 0.2 mmol), K$_3$PO$_4$ (57 mg, 0.27 mmol), XPhos-Pd-G2 (Chloro(2-dicyclohexylphosphino-2',4',6'-triisopropyl-1,1'-biphenyl)[2-(2'-amino-1,1'-biphenyl)]palladium(II)) (5.3 mg, 0.007 mmol) are placed into a round bottom flask under nitrogen. Dioxane (3 mL) is added, followed by water (1.5 mL) and nitrogen bubbled through the mixture for 15 min. The reaction mixture is heated to 95° C. for 2 h, cooled to room temperature, diluted with AcOEt (10 mL) and poured into saturated NH$_4$Cl (10 mL). The layers are separated and the aqueous layer is extracted with AcOEt (2×10 mL). The combined organic layers are dried over sodium sulfate, filtered and concentrated. The crude mixture is purified by column chromatography (CH$_2$Cl$_2$/MeOH 20:1). The title compound is obtained as a solid (46 mg, 96%).

$^1$H NMR (400 MHz, D$_6$-DMSO) δ 9.0 (s, 2H), 7.01 (s, 2H), 4.06-4.02 (dd, J=13.4, 2.6 Hz, 1H), 3.91-3.84 (m, 1H), 3.78-3.70 (m, 2H), 3.67-3.55 (m, 8H), 3.31-3.09 (m, 4H), 2.66-2.61 (dd, J=15.4, 4.6 Hz, 1H). $^{13}$C NMR (100 MHz, D$_6$-DMSO) δ 167.1, 164.0, 158.8, 158.0, 157.7, 120.2, 93.5, 70.2, 69.6, 66.2, 65.7, 56.4, 45.4, 41.6, 28.7. MS (MALDI): 356 (M+H).

Example 10

(S)-5-(4-morpholino-5a,6,8,9-tetrahydro-5H-pyrimido[5',4':4,5]pyrrolo[2,1-c][1,4]oxazin-2-yl)pyrimidin-2-amine

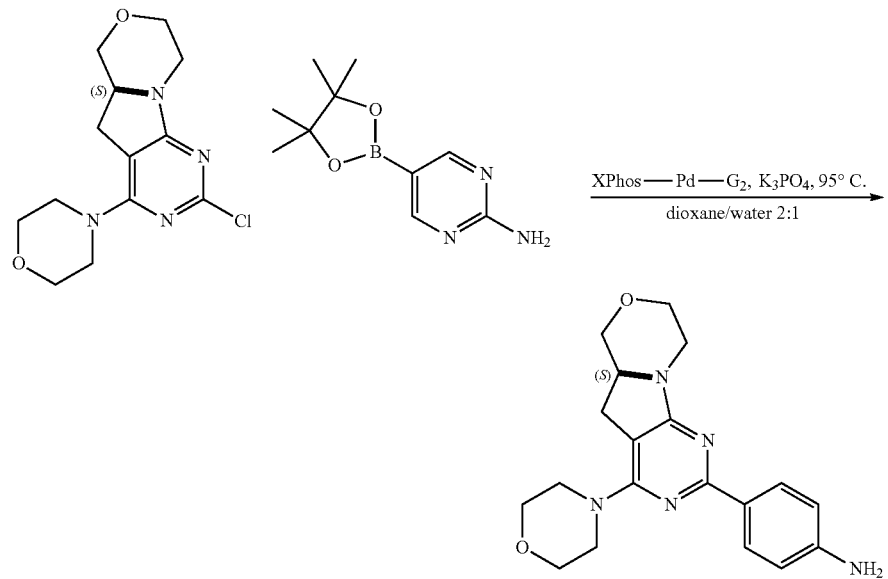

(S)-2-Chloro-4-morpholino-5a,6,8,9-tetrahydro-5H-pyrimido[5',4':4,5]pyrrolo[2,1-c][1,4]oxazine (40 mg, 0.135 mmol), 5-(4,4,5,5-tetramethyl-1,3,2-dioxaborolan-2-yl)-pyrimidin-2-amine (45 mg, 0.2 mmol), K$_3$PO$_4$ (57 mg, 0.27 mmol), XPhos-Pd-G2 (chloro(2-dicyclohexylphosphino-2',4',6'-triisopropyl-1,1'-biphenyl)[2-(2'-amino-1,1'-biphenyl)]palladium(II)) (5.3 mg, 0.007 mmol) are placed into a round bottom flask under nitrogen. Dioxane (3 mL) is added, followed by water (1.5 mL) and nitrogen bubbled through the mixture for 15 min. The reaction mixture is heated to 95° C. for 2 h, cooled to rt, diluted with AcOEt (10 mL) and poured into saturated NH$_4$Cl (10 mL). The layers are separated and the aqueous layer extracted with AcOEt (2×10 mL). The combined organic layers are dried over sodium sulfate, filtered and concentrated. The crude mixture is purified by column chromatography (CH$_2$Cl$_2$/MeOH 20:1). The title compound is obtained as a solid (32 mg, 67%).

$^1$H NMR (400 MHz, D$_6$-DMSO) δ 9.0 (s, 2H), 7.01 (s, 2H), 4.06-4.02 (dd, J=13.4, 2.6 Hz, 1H), 3.91-3.84 (m, 1H), 3.78-3.70 (m, 2H), 3.67-3.55 (m, 8H), 3.31-3.09 (m, 4H), 2.66-2.61 (dd, J=15.4, 4.6 Hz, 1H). $^{13}$C NMR (100 MHz, D$_6$-DMSO) δ 167.1, 164.0, 158.8, 158.0, 157.7, 120.2, 93.5, 70.2, 69.6, 66.2, 65.7, 56.4, 45.4, 41.6, 28.7. MS (MALDI): 356 (M+H).

In-Cell Western Blot

A2058 cells were plated at 20,000 cells/well in a 96-well plate (Perkin Elmer, Cat. No. 6005558) and 24 h later treated with different compounds for 1 h. For each compound 7 different concentrations were applied on cells (5 μM, 1.25 μM, 0.625 μM, 0.3125 μM, 0.155 μM, 0.08 μM and 0.04 μM). Cells were fixed with 4% paraformaldehyde for 30 min at RT, washed 2 times with 1% BSA in PBS, permeabilized with 0.1% Triton X-100 in PBS/1% BSA for 30 min at rt and blocked with 5% goat serum in PBS/1% BSA/0.1% Triton X-100 for 30 min at rt. Cells were stained with primary antibody either with rabbit anti-pPKB S473 (1:500; Cell Signalling Technology, Cat. No. 4058) combined with mouse anti-α-Tubulin (1:2000; used for normalization; Sigma, Cat. No. T9026) or with rabbit anti-pS6 S235/S236 (1:500; Cell Signalling Technology, Cat. No. 4856) combined with mouse anti-α-Tubulin (1:2000; used for normalization) over night at 4° C. After 3 times 5 min wash with PBS/1% BSA/0.1% Triton cells were treated with the secondary antibodies goat-anti-mouse IRDye680 (LICOR, Cat. No. 926-68070) and goat-anti-rabbit IRDye800 (LICOR, 926-32211) (each diluted 1:500 in PBS/1% BSA/0.1% Triton) for 1 h while shaking in the dark. Cells were washed 3 times 5 min with PBS/1% BSA/0.1% Triton and plate scanned with the Odyssey Infrared Scanning system using both 700 and 800 nm channels. As control for 0% inhibition vehicle (0.2% DMSO) was added to cells. To correct for background staining in the data analysis wells were treated only with secondary antibodies.

For data analysis the mean background signal from channel 700 nm and 800 nm were subtracted from each signal in channel 700 nm and 800 nm, respectively. The signals in each channel were normalized to the 0% inhibition and then signal ratio 800 nm over 700 nm was performed to obtain the values for either pPBK S473 or pS6 S235/S236 normalized to α-Tubulin.

$IC_{50}$ values of each compound were determined by plotting the normalized pPBK S473 and pS6 S235/S236 signals, respectively, versus the compound concentrations (in logarithmic scale) and then by fitting a sigmoidal dose-response curve with variable slope to the data using GraphPad™ Prism.

In Vitro PI3K Alpha Binding Assay

N-terminally His-tagged PI3K alpha (Cat. No. PV4789; 0.49 mg/ml), Alexa Fluor® 647 labeled kinase Tracer 314 (Cat. No. PV6087), Biotin anti-His Tag antibody (Cat. No PV6089) and LanthaScreen® Eu-Streptavidin (Cat. No. PV5899) were purchased from Life Technologies. The 1× Kinase Buffer A consists of 50 mM HEPES pH 7.5, 10 mM $MgCl_2$, 1 mM EGTA, and 0.01% (v/v) Brij-35 (Sigma Cat. No. B4184-100ML).

A 4-fold serial dilution of each compound to be tested was prepared in DMSO (master dilution) in a 96-well polystyrene plate (Falcon Cat. No. 353072, flat bottom) with the highest concentration at 1000 μM and the lowest at 0.004 μM. The master dilution series were diluted further 33.3-fold into Kinase Buffer A by transferring 5 μl of each concentration of diluted compound to 162 μl Kinase Buffer A in a new 96-well plate resulting to a 3-fold serially compound dilution. Based on a Tracer 314 titration experiment a working concentration of 20 nM was chosen. Therefore a 60 nM Tracer 314 solution in Kinase Buffer A was prepared resulting in a 3-fold concentrated solution. A 3-fold concentrated kinase/antibody solution at 15 nM kinase, 6 nM antibody and 6 nM Eu-Streptavidin was prepared in Kinase Buffer A. Five μl of each 3× serially diluted compound were dispensed in a 384-well plate in duplicate. Then to each well 5 μl of 3× kinase/antibody mixture was added followed by the addition of 5 μl 3× Tracer 314 solution. After 1 h incubation at rt, time-resolved FRET was measured with a Synergy 4 multi-mode microplate reader (Biotek Instruments) using the following settings: 100 μs delay before data collection, 200 μs time for data collection, 10 measurements per data point. Emission filter: 665 nm/8 nm with sensitivity set to 163 and 620 nm/10 nm with sensitivity set to 135; Excitation filter: 340 nm/30 nm; Dichroic mirror 400 nm.

For data analysis, emission ratio was calculated by dividing the signal emitted at 665 nm from the acceptor (Alexa Fluor® 647 labeled Tracer 314) by the signal emitted at 620 nm from the donor (Eu-labeled antibody). $IC_{50}$ values of each compound were determined by plotting the emission ratio versus the compound concentrations (in logarithmic scale) and then by fitting a sigmoidal dose-response curve with variable slope to the data using GraphPad™ Prism.

Results

| | In-cell Western blot | | in vitro PI3K alpha binding | |
|---|---|---|---|---|
| Compound | pPKB S473 IC50 [nM] | pS6 S235/236 IC50 [nM] | p110α IC50 [nM] | p110α Ki [nM] |
| 6 | 425.4 | 695.9 | 390.4 | n.d. |
| 9 | 145 | 65 | 411 | 42 |
| 22 | 428.5 | 1088 | 98.1 | n.d. |
| 25 | 154 | 98 | 76 | 8 |
| 38 | 5909 | 9080 | 2623 | n.d. |
| 41 | 575 | 574 | 231 | 23 |
| 54 | 833 | 2111 | 383.1 | n.d. |
| 57 | 1261 | 594 | 1637 | 166 | n.d. = not determined

The invention claimed is:
1. Compounds of formula (I) and (II),

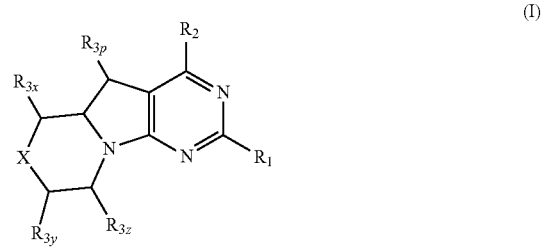

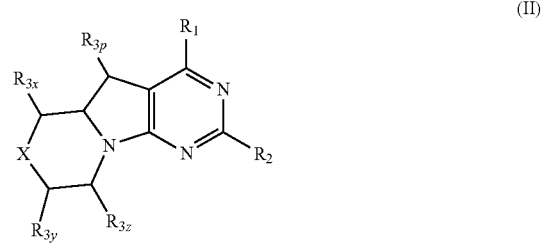

and stereoisomers, geometric isomers, tautomers, solvates, and pharmaceutically acceptable salts thereof, wherein $R_1$ is

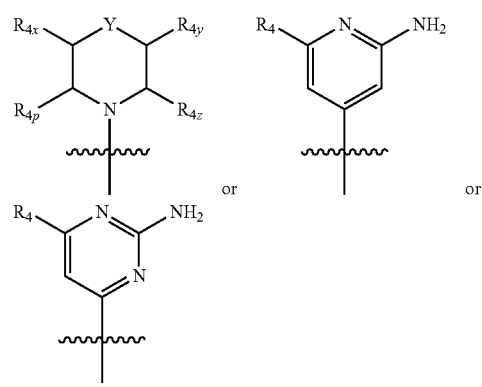

X and Y are independently selected from the group consisting of $C(R_8)_2$, O, S, SO, $SO_2$, and $NR_7$;

$R_{3x}$, $R_{3y}$, $R_{3z}$, $R_{3p}$ and $R_4$ are independently selected from the group consisting of hydrogen, D, F, Cl, Br, I, $C_1$-$C_{12}$ alkyl, $C_2$-$C_8$ alkenyl, $C_2$-$C_8$ alkynyl, —($C_1$-$C_{12}$ alkylene)-($C_3$-$C_{12}$ carbocyclyl), —($C_1$-$C_{12}$ alkylene)-(heterocyclyl having 3-20 ring atoms), —($C_1$-$C_{12}$ alkylene)-C(=O)-(heterocyclyl having 3-20 ring atoms), —($C_1$-$C_{12}$ alkylene)-($C_6$-$C_{20}$ aryl) and —($C_1$-$C_{12}$ alkylene)-(heteroaryl having 5-20 ring atoms), —C(($C_1$-$C_6$ alkyl)$_2$NR$_5$R$_6$, —(CR$_8$R$_9$)$_t$NR$_5$R$_6$, —(CR$_8$R$_9$)$_n$NR$_7$C(=Z)R$_8$, (CR$_8$R$_9$)$_n$NR$_7$S(O)$_2$R$_5$, —CH(OR$_5$)R$_6$, —(CR$_8$R$_9$)$_n$OR$_5$, —(CR$_8$R$_9$)$_n$S(O)$_2$R$_5$, —(CR$_8$R$_9$)$_n$S(O)$_2$NR$_5$R$_6$, —C(=Z)R$_5$, —C(=Z)OR$_5$, C(=Z)NR$_5$R$_6$, —C(=Z)NR$_7$OR$_5$, —C(=O)NR$_7$S(O)$_2$R$_5$, —C(=O)NR$_7$(CR$_8$R$_9$)$_m$NR$_5$R$_6$, —NO$_2$, —NHR$_7$, —NR$_7$C(=Z)R$_5$, —NR$_7$C(=Z)OR$_5$, —NR$_7$C(=Z)NR$_5$R$_6$, —NR$_7$S(O)$_2$R$_5$, —NR$_7$SO$_2$NR$_5$R$_6$, —S(O)$_2$R$_5$, —S(O)$_2$NR$_5$R$_6$, —SC(=Z)R$_5$, —SC(=Z)OR$_5$, C$_3$-C$_{12}$ carbocyclyl, C$_2$-C$_{20}$ heterocyclyl, C$_6$-C$_{20}$ aryl, and C$_1$—C=NR$_7$, OR$_5$, —OC(=Z)R$_5$, —OC(=Z)OR$_5$, —OC(=Z)NR$_5$R$_6$, and —OS(O)$_2$(OR$_5$);

R$_{4x}$, R$_{4y}$, R$_{4z}$, and R$_{4p}$ are independently selected from the group consisting of hydrogen, D, F, Cl, Br, I, C$_1$-C$_{12}$ alkyl, C$_2$-C$_8$ alkenyl, C$_2$-C$_8$ alkynyl, or one or two of R$_{4x}$, R$_{4y}$, R$_{4z}$, and R$_{4p}$ are two geminal substituents methyl and the other ones are hydrogen, or R$_{4x}$ and R$_{4y}$, or R$_{4z}$ and R$_{4p}$ form together an annullated five- or six-membered carbocyclyl, heterocyclyl, aryl or heteroaryl ring, or R$_{4x}$ and R$_{4y}$, form together bridging ethylene or methylene, R$_{4p}$ and R$_{4z}$ form together bridging ethylene or methylene, or R$_{4y}$ and R$_{4p}$ form together bridging ethylene or methylene;

wherein said alkyl, alkenyl, alkynyl, carbocyclyl, heterocyclyl, aryl and heteroaryl are optionally substituted with one or more groups independently selected from F, Cl, Br, I, CN, CF$_3$, NO$_2$, oxo, —C(=Z)R$_5$, —C(=Z)OR$_5$, —C(=Z)NR$_5$R$_6$, —(CR$_8$R$_9$)$_n$NR$_5$R$_6$, —(CR$_8$R$_9$)$_n$C(=Z)NR$_5$R$_6$, —(CR$_8$R$_9$)$_n$C(=Z)OR$_5$, —(CR$_8$R$_9$)$_n$NR$_7$SO$_2$R$_5$, —(CR$_8$R$_9$)$_n$OR$_5$, —(CR$_8$R$_9$)$_n$R$_5$, —(CR$_8$R$_9$)$_n$SO$_2$R$_5$, —NR$_5$R$_6$, —NR$_7$C(=Z)R$_5$, —NR$_7$C(=Z)OR$_5$, —NR$_7$C(=Z)NR$_5$R$_6$, —NR$_7$SO$_2$R$_5$), —OP(OR$_5$)(OR$_6$), SR$_5$, —S(O)R$_5$, —S(O)$_2$R$_5$, —S(O)$_2$NR$_5$R$_6$, —S(O)(OR$_5$), —S(O)$_2$(OR$_5$), —SC(=Z)R$_5$, —SC(=Z)OR$_5$, —SC(=Z)NR$_5$R$_6$, optionally substituted C$_1$-C$_{12}$ alkyl, optionally substituted C$_2$-C$_8$ alkenyl, optionally substituted C$_2$-C$_8$ alkynyl, optionally substituted C$_3$-C$_{12}$ carbocyclyl, optionally substituted C$_2$-C$_{20}$ heterocyclyl, optionally substituted C$_6$-C$_{20}$ aryl, and optionally substituted C$_1$-C$_{20}$ heteroaryl;

R$_5$, R$_6$ and R$_7$ are independently selected from H, D, C$_1$-C$_{12}$ alkyl, C$_2$-C$_8$ alkenyl, C$_3$-C$_8$ alkynyl, C$_3$-C$_{12}$ carbocyclyl, C$_2$-C$_{20}$ heterocyclyl, C$_6$-C$_{20}$ aryl, and C$_1$-C$_{20}$ heteroaryl, or R$_5$ and R$_6$ together with the nitrogen to which they are attached form a C$_3$-C$_{20}$ heterocyclic ring optionally containing one or more additional ring atoms selected from N, O or S, wherein said heterocyclic ring is optionally substituted with one or more groups independently selected from oxo, CF$_3$, F, Cl, Br, I, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl and C$_1$-C$_{20}$ heteroaryl;

R$_8$ and R$_9$ are independently selected from H, D, C$_1$-C$_{12}$ alkyl, and —(CH$_2$)$_n$-aryl, or R$_8$ and R$_9$ together with the atoms to which they are attached form a saturated or partially unsaturated C$_3$-C$_{12}$ carbocyclic ring;

m is 0, 1, 2, 3, 4, 5 or 6;

n is 1, 2, 3, 4, 5, or 6;

t is 2, 3, 4, 5 or 6; and

R$_2$ is independently selected from the groups consisting of a monocyclic or bicyclic aryl or heteroaryl with 1-6 heteroatoms selected from O, N, S, with 1-4 substituents selected from C$_1$-C$_4$ alkyl, D, F, Cl, Br, I, —OR$_5$, —COOH, COORS, —CONR$_5$R$_6$, —SO$_2$NR$_5$R$_6$, CN, CF$_3$, CHF$_2$, CFH$_2$, OCF$_3$, OCOR$_5$, NR$_7$COR$_5$, NR$_7$SO$_2$R$_5$, NR$_5$R$_6$, SO$_2$R$_5$, SOR$_5$, and SR$_5$.

2. The compound of claim 1 wherein R$_2$ is

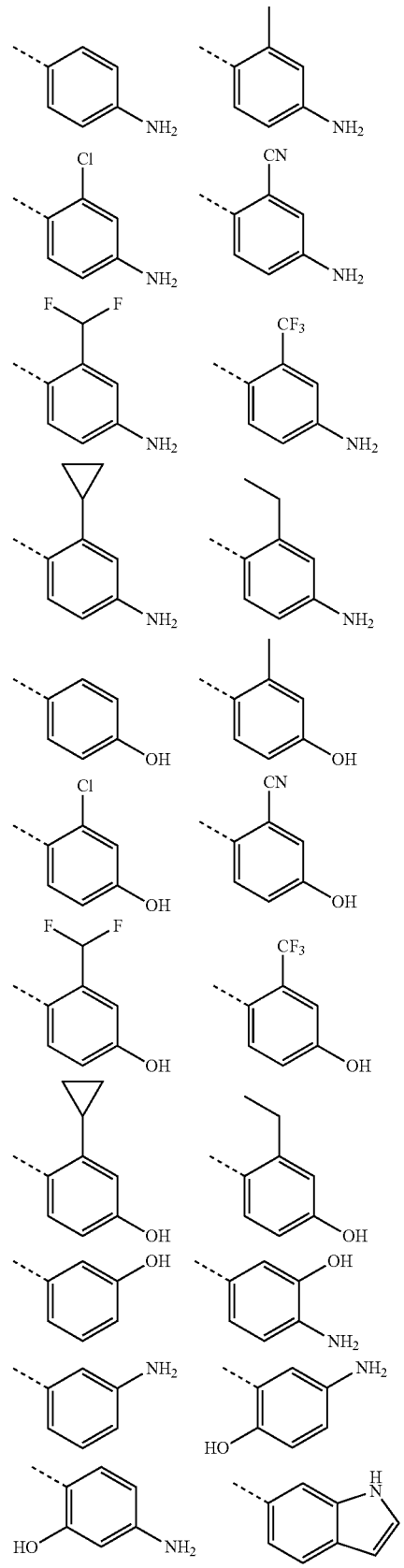

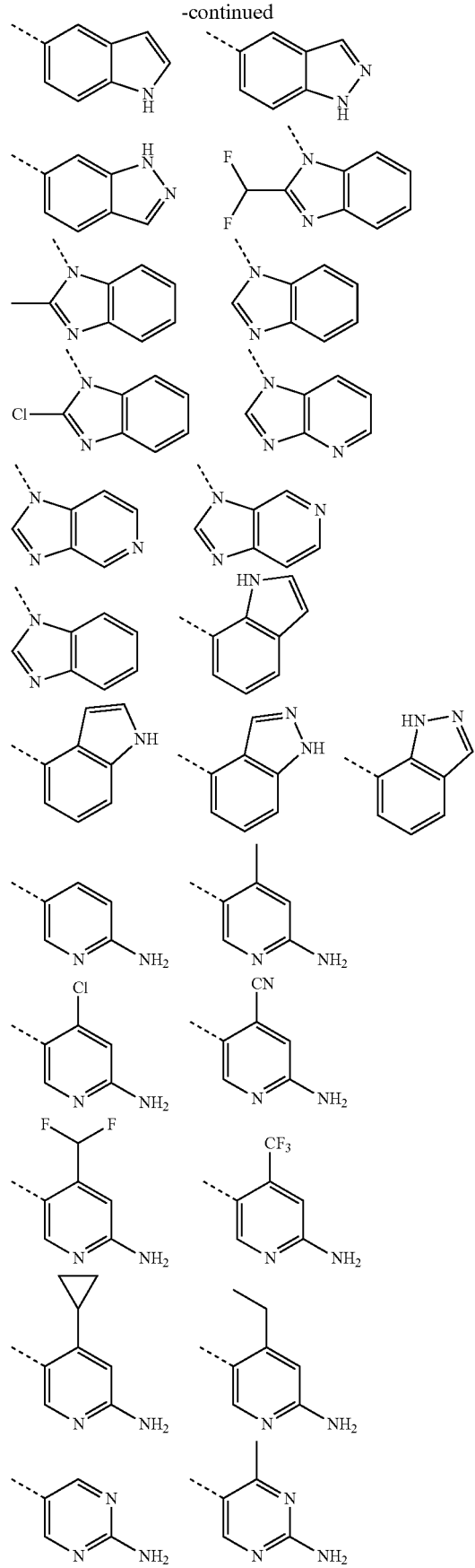
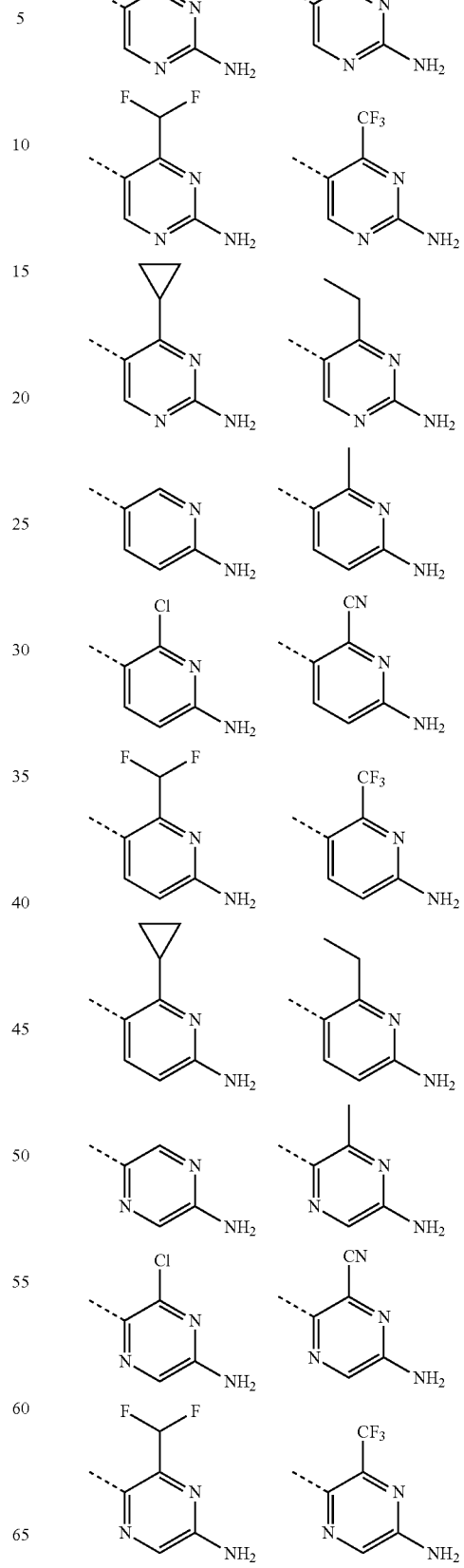

87

-continued

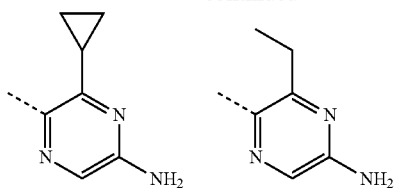

wherein the dotted line indicates the point of attachment of $R_2$, the amino function may be further substituted with $C_1$-$C_8$-acyl, oxycarbonyl or aminocarbonyl, and the other substituents have the meaning indicated in claim 1.

3. The compound of claim 1 wherein $R_2$ is

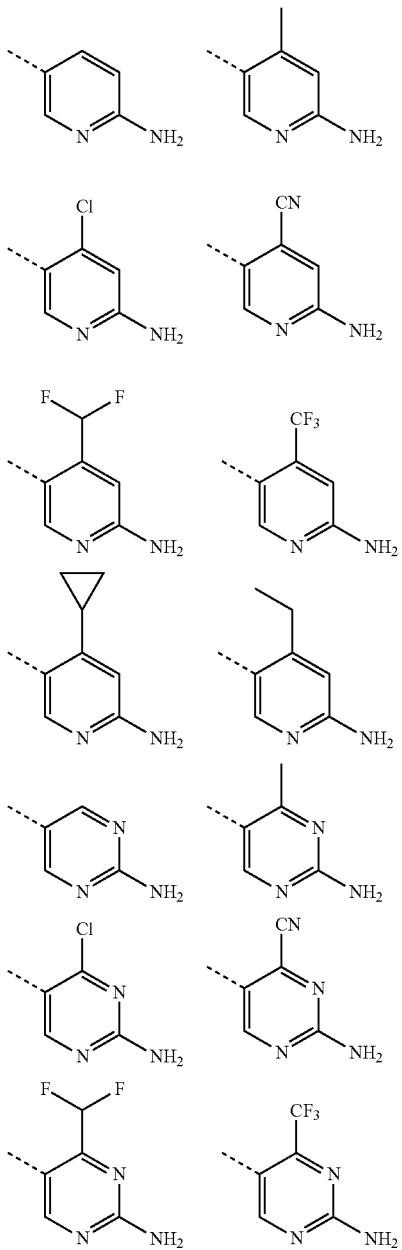

88

-continued

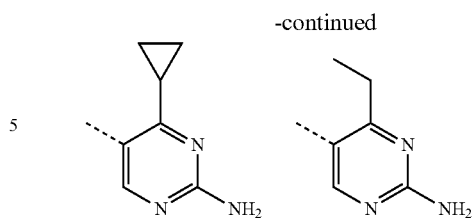

wherein the dotted line indicates the point of attachment of $R_2$, the amino function may be further substituted with $C_1$-$C_8$-acyl, oxycarbonyl or aminocarbonyl, and the other substituents have the meaning indicated in claim 1.

4. The compound of claim 1 wherein $R_1$ is

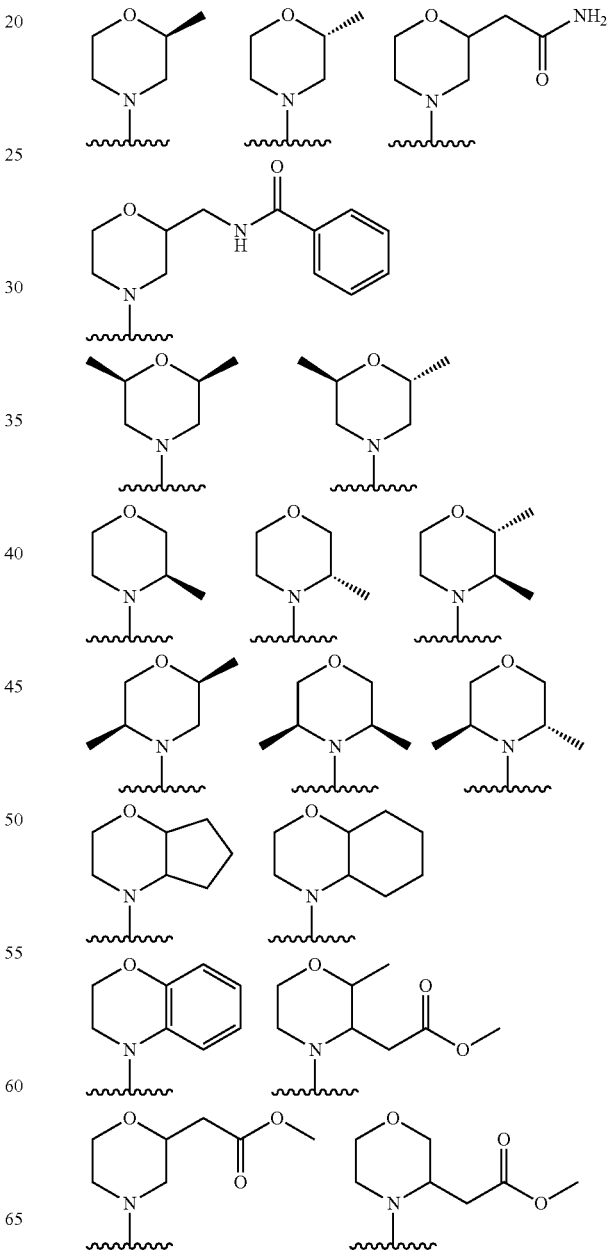

-continued

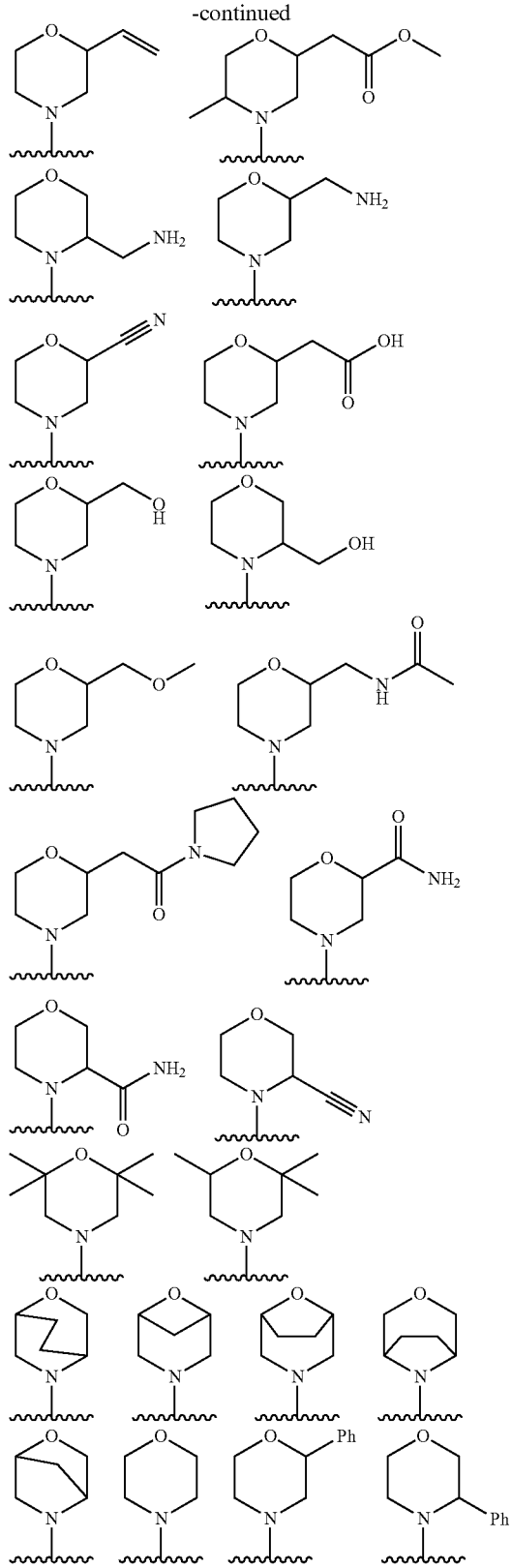

optionally further substituted with one or more groups independently selected from D, F, Cl, Br, I, —CH$_3$, —CH$_2$CH$_3$, —CH$_2$CH$_2$CH$_3$, —CH(CH$_3$)$_2$, —C(CH$_3$)$_3$, —CH$_2$OCH$_3$, —CHF$_2$, —CN, —CF$_3$, —CH$_2$OH, —CH$_2$OCH$_3$, —CH$_2$CH$_2$OH, —CH$_2$C(CH$_3$)$_2$OH, —CH(CH$_3$)OH, —CH(CH$_2$CH$_3$)OH—CH$_2$CH(OH)CH$_3$, —C(CH$_3$)$_2$OH, —C(CH$_3$)$_2$OCH$_3$, —CH(CH$_3$)F, —C(CH$_3$)F$_2$, —CH(CH$_2$CH$_3$)F, —C(CH$_2$CH$_3$)$_2$F, —CO$_2$H, —CONH$_2$, —CON(CH$_2$CH$_3$)$_2$, —COCH$_3$, —CON(CH$_3$)$_2$, —NO$_2$, —NH$_2$, —NHCH$_3$, —N(CH$_3$)$_2$, —NHCH$_2$CH$_3$, —NHCH(CH$_3$)$_2$, —NHCH$_2$CH$_2$OH, —NHCH$_2$CH$_2$OCH$_3$, —NHCOCH$_3$, —NHCOCH$_2$CH$_3$, —NHCOCH$_2$OH, —NHS(O)$_2$CH$_3$, —N(CH$_3$)S(O)$_2$CH$_3$, =O, —OH, —OCH$_3$, —OCH$_2$CH$_3$, —OCH(CH$_3$)$_2$, —SH, —NHC(=O)NHCH$_3$, —NHC(=O)NHCH$_2$CH$_3$, —S(O)CH$_3$, —S(O)CH$_2$CH$_3$, —S(O)$_2$CH$_3$, —S(O)$_2$NH$_2$, —S(O)$_2$NHCH$_3$, —S(O)$_2$N(CH$_3$)$_2$, and —CH$_2$S(O)$_2$CH$_3$;

wherein the dotted line indicates the point of attachment of R$_1$, and the other substituents have the meanings indicated in claim 1, 2 or 3.

5. The compound of claim 1 wherein R$_1$ is

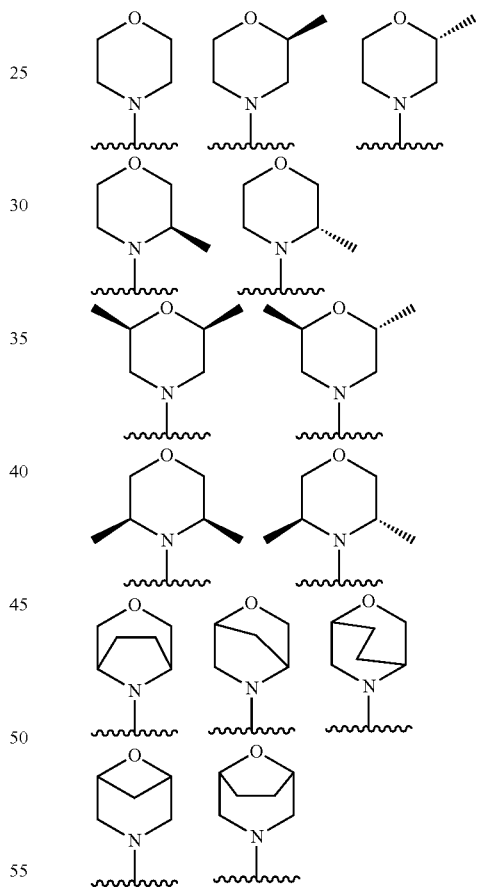

wherein the dotted line indicates the point of attachment of R$_1$, and the other substituents have the meanings indicated in claim 1, 2 or 3.

6. The compound of claim 1 wherein R$_1$ is morpholino; and the other substituents have the meanings indicated in claim 1, 2 or 3.

7. The compound of claim 1 wherein X is O or S.

8. The compound of claim 1 wherein R$_{3x}$, R$_{3y}$, R$_{3z}$, and R$_{3p}$ are H.

9. The compound of claim 1 wherein R₁ is

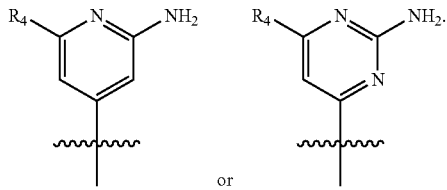

or

10. The compound of any of claim 1 having formula (Ia) or (Ib)

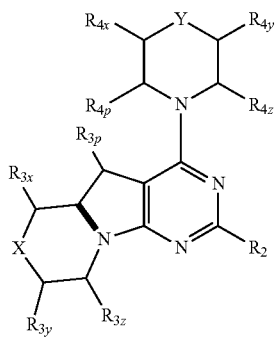

(Ia)

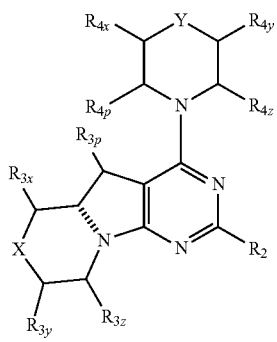

(Ib)

and stereoisomers, geometric isomers, tautomers, solvates, and pharmaceutically acceptable salts thereof, wherein the substituents are as defined as in claim 1.

11. The compound of claim 1 having formula (IIa) or (IIb)

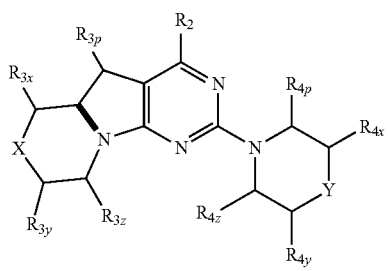

(IIa)

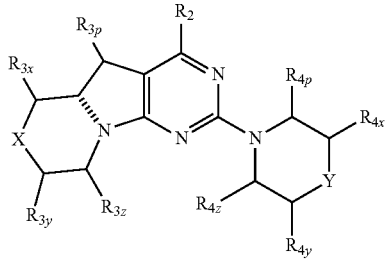

(IIb)

and stereoisomers, geometric isomers, tautomers, solvates, and pharmaceutically acceptable salts thereof, wherein the substituents are as defined as in claim 1.

12. The compound of claim 1 selected from the group consisting of
- (R)-5-(4-morpholino-5a,6,8,9-tetrahydro-5H-pyrimido[5',4':4,5]pyrrolo[2,1-c][1,4]oxazin-2-yl)pyridin-2-amine
- (R)-4-methyl-5-(4-morpholino-5a,6,8,9-tetrahydro-5H-pyrimido[5',4':4,5]pyrrolo[2,1-c][1,4]oxazin-2-yl)pyridin-2-amine
- (R)-4-chloro-5-(4-morpholino-5a,6,8,9-tetrahydro-5H-pyrimido[5',4':4,5]pyrrolo[2,1-c][1,4]oxazin-2-yl)pyridin-2-amine
- (R)-2-amino-5-(4-morpholino-5a,6,8,9-tetrahydro-5H-pyrimido[5',4':4,5]pyrrolo[2,1-c][1,4]oxazin-2-yl)isonicotinonitrile
- (R)-4-(difluoromethyl)-5-(4-morpholino-5a,6,8,9-tetrahydro-5H-pyrimido[5',4':4,5]pyrrolo[2,1-c][1,4]oxazin-2-yl)pyridin-2-amine
- (R)-5-(4-morpholino-5a,6,8,9-tetrahydro-5H-pyrimido[5',4':4,5]pyrrolo[2,1-c][1,4]oxazin-2-yl)-4-(trifluoromethyl)pyridin-2-amine
- (R)-4-cyclopropyl-5-(4-morpholino-5a,6,8,9-tetrahydro-5H-pyrimido[5',4':4,5]pyrrolo[2,1-c][1,4]oxazin-2-yl)pyridin-2-amine
- (R)-4-ethyl-5-(4-morpholino-5a,6,8,9-tetrahydro-5H-pyrimido[5',4':4,5]pyrrolo[2,1-c][1,4]oxazin-2-yl)pyridin-2-amine
- (R)-5-(4-morpholino-5a,6,8,9-tetrahydro-5H-pyrimido[5',4':4,5]pyrrolo[2,1-c][1,4]oxazin-2-yl)pyrimidin-2-amine
- (R)-4-methyl-5-(4-morpholino-5a,6,8,9-tetrahydro-5H-pyrimido[5',4':4,5]pyrrolo[2,1-c][1,4]oxazin-2-yl)pyrimidin-2-amine
- (R)-4-chloro-5-(4-morpholino-5a,6,8,9-tetrahydro-5H-pyrimido[5',4':4,5]pyrrolo[2,1-c][1,4]oxazin-2-yl)pyrimidin-2-amine
- (R)-2-amino-5-(4-morpholino-5a,6,8,9-tetrahydro-5H-pyrimido[5',4':4,5]pyrrolo[2,1-c][1,4]oxazin-2-yl)pyrimidine-4-carbonitrile
- (R)-4-(difluoromethyl)-5-(4-morpholino-5a,6,8,9-tetrahydro-5H-pyrimido[5',4':4,5]pyrrolo[2,1-c][1,4]oxazin-2-yl)pyrimidin-2-amine
- (R)-5-(4-morpholino-5a,6,8,9-tetrahydro-5H-pyrimido[5',4':4,5]pyrrolo[2,1-c][1,4]oxazin-2-yl)-4-(trifluoromethyl)pyrimidin-2-amine
- (R)-4-cyclopropyl-5-(4-morpholino-5a,6,8,9-tetrahydro-5H-pyrimido[5',4':4,5]pyrrolo[2,1-c][1,4]oxazin-2-yl)pyrimidin-2-amine
- (R)-4-ethyl-5-(4-morpholino-5a,6,8,9-tetrahydro-5H-pyrimido[5',4':4,5]pyrrolo[2,1-c][1,4]oxazin-2-yl)pyrimidin-2-amine (S)-5-(4-morpholino-5a,6,8,9-tetrahydro-5H-pyrimido[5',4':4,5]pyrrolo[2,1-c][1,4]oxazin-2-yl)pyridin-2-amine (S)-4-methyl-5-(4-morpholino-5a,6,8,9-tetrahydro-5H-pyrimido[5',4':4,5]pyrrolo[2,1-c][1,4]oxazin-2-yl)pyridin-2-amine (S)-4-chloro-5-(4-morpholino-5a,6,8,9-tetrahydro-5H-pyrimido[5',4':4,5]pyrrolo[2,1-c][1,4]oxazin-2-yl)pyridin-2-amine (S)-2-amino-5-(4-morpholino-5a,6,8,9-tetrahydro-5H-pyrimido[5',4':4,5]pyrrolo[2,1-c][1,4]oxazin-2-yl)isonicotinonitrile (S)-4-(difluoromethyl)-5-(4-morpholino-5a,6,8,9-tetrahydro-5H-pyrimido[5',4':4,5]pyrrolo[2,1-c][1,4]oxazin-2-yl)pyridin-2-amine (S)-5-(4-morpholino-5a,6,8,9-tetrahydro-5H-pyrimido[5',4':4,5]pyrrolo[2,1-c][1,4]oxazin-2-yl)-4-(trifluoromethyl)pyridin-2-amine (S)-4-cyclopropyl-5-(4-morpholino-5a,6,8,9-tetrahydro-5H-pyrimido[5',4':4,5]pyrrolo[2,1-c][1,4]oxazin-2-yl)pyridin-2-amine (S)-4-ethyl-5-(4-morpholino-5a,6,8,9-tetrahydro-5H-pyrimido[5',4':4,5]pyrrolo[2,1-c][1,4]oxazin-2-yl)pyridin-2-amine (S)-5-(4-morpholino-5a,6,8,9-tetrahydro-5H-pyrimido[5',4':4,5]pyrrolo[2,1-c][1,4]oxazin-2-yl)pyrimidin-2-amine (S)-4-methyl-5-(4-morpholino-5a,6,8,9-tetrahydro-5H-pyrimido[5',4':4,5]pyrrolo[2,1-c][1,4]oxazin-2-yl)pyrimidin-2-amine (S)-4-chloro-5-(4-morpholino-5a,6,8,9-tetrahydro-5H-pyrimido[5',4':4,5]pyrrolo[2,1-c][1,4]oxazin-2-yl)pyrimidin-2-amine (S)-2-amino-5-(4-morpholino-5a,6,8,9-tetrahydro-5H-pyrimido[5',4':4,5]pyrrolo[2,1-c][1,4]oxazin-2-yl)pyrimidine-4-carbonitrile (S)-4-(difluoromethyl)-5-(4-morpholino-5a,6,8,9-tetrahydro-5H-pyrimido[5',4':4,5]pyrrolo[2,1-c][1,4]oxazin-2-yl)pyrimidin-2-amine (S)-5-(4-morpholino-5a,6,8,9-tetrahydro-5H-pyrimido[5',4':4,5]pyrrolo[2,1-c][1,4]oxazin-2-yl)-4-(trifluoromethyl)pyrimidin-2-amine (S)-4-cyclopropyl-5-(4-morpholino-5a,6,8,9-tetrahydro-5H-pyrimido[5',4':4,5]pyrrolo[2,1-c][1,4]oxazin-2-yl)pyrimidin-2-amine (S)-4-ethyl-5-(4-morpholino-5a,6,8,9-tetrahydro-5H-pyrimido[5',4':4,5]pyrrolo[2,1-c][1,4]oxazin-2-yl)pyrimidin-2-amine (R)-5-(2-morpholino-5a,6,8,9-tetrahydro-5H-pyrimido[5',4':4,5]pyrrolo[2,1-c][1,4]oxazin-4-yl)pyridin-2-amine (R)-4-methyl-5-(2-morpholino-5a,6,8,9-tetrahydro-5H-pyrimido[5',4':4,5]pyrrolo[2,1-c][1,4]oxazin-4-yl)pyridin-2-amine (R)-4-chloro-5-(2-morpholino-5a,6,8,9-tetrahydro-5H-pyrimido[5',4':4,5]pyrrolo[2,1-c][1,4]oxazin-4-yl)pyridin-2-amine (R)-2-amino-5-(2-morpholino-5a,6,8,9-tetrahydro-5H-pyrimido[5',4':4,5]pyrrolo[2,1-c][1,4]oxazin-4-yl)isonicotinonitrile (R)-4-(difluoromethyl)-5-(2-morpholino-5a,6,8,9-tetrahydro-5H-pyrimido[5',4':4,5]pyrrolo[2,1-c][1,4]oxazin-4-yl)pyridin-2-amine (R)-5-(2-morpholino-5a,6,8,9-tetrahydro-5H-pyrimido[5',4':4,5]pyrrolo[2,1-c][1,4]oxazin-4-yl)-4-(trifluoromethyl)pyridin-2-amine (R)-4-cyclopropyl-5-(2-morpholino-5a,6,8,9-tetrahydro-5H-pyrimido[5',4':4,5]pyrrolo[2,1-c][1,4]oxazin-4-yl)pyridin-2-amine (R)-4-ethyl-5-(2-morpholino-5a,6,8,9-tetrahydro-5H-pyrimido[5',4':4,5]pyrrolo[2,1-c][1,4]oxazin-4-yl)pyridin-2-amine (R)-5-(2-morpholino-5a,6,8,9-tetrahydro-5H-pyrimido[5',4':4,5]pyrrolo[2,1-c][1,4]oxazin-4-yl)pyrimidin-2-amine (R)-4-methyl-5-(2-morpholino-5a,6,8,9-tetrahydro-5H-pyrimido[5',4':4,5]pyrrolo[2,1-c][1,4]oxazin-4-yl)pyrimidin-2-amine (R)-4-chloro-5-(2-morpholino-5a,6,8,9-tetrahydro-5H-pyrimido[5',4':4,5]pyrrolo[2,1-c][1,4]oxazin-4-yl)pyrimidin-2-amine (R)-2-amino-5-(2-morpholino-5a,6,8,9-tetrahydro-5H-pyrimido[5',4':4,5]pyrrolo[2,1-c][1,4]oxazin-4-yl)isonicotinonitrile (R)-4-(difluoromethyl)-5-(2-morpholino-5a,6,8,9-tetrahydro-5H-pyrimido[5',4':4,5]pyrrolo[2,1-c][1,4]oxazin-4-yl)pyrimidin-2-amine (R)-5-(2-morpholino-5a,6,8,9-tetrahydro-5H-pyrimido[5',4':4,5]pyrrolo[2,1-c][1,4]oxazin-4-yl)-4-(trifluoromethyl)pyrimidin-2-amine (R)-4-cyclopropyl-5-(2-morpholino-5a,6,8,9-tetrahydro-5H-pyrimido[5',4':4,5]pyrrolo[2,1-c][1,4]oxazin-4-yl)pyrimidin-2-amine (R)-4-ethyl-5-(2-morpholino-5a,6,8,9-tetrahydro-5H-pyrimido[5',4':4,5]pyrrolo[2,1-c][1,4]oxazin-4-yl)pyrimidin-2-amine (S)-5-(2-morpholino-5a,6,8,9-tetrahydro-5H-pyrimido[5',4':4,5]pyrrolo[2,1-c][1,4]oxazin-4-yl)pyridin-2-amine (S)-4-methyl-5-(2-morpholino-5a,6,8,9-tetrahydro-5H-pyrimido[5',4':4,5]pyrrolo[2,1-c][1,4]oxazin-4-yl)pyridin-2-amine (S)-4-chloro-5-(2-morpholino-5a,6,8,9-tetrahydro-5H-pyrimido[5',4':4,5]pyrrolo[2,1-c][1,4]oxazin-4-yl)pyridin-2-amine (S)-2-amino-5-(2-morpholino-5a,6,8,9-tetrahydro-5H-pyrimido[5',4':4,5]pyrrolo[2,1-c][1,4]oxazin-4-yl)isonicotinonitrile (S)-4-(difluoromethyl)-5-(2-morpholino-5a,6,8,9-tetrahydro-5H-pyrimido[5',4':4,5]pyrrolo[2,1-c][1,4]oxazin-4-yl)pyrimidin-2-amine (S)-5-(2-morpholino-5a,6,8,9-tetrahydro-5H-pyrimido[5',4':4,5]pyrrolo[2,1-c][1,4]oxazin-4-yl)-4-(trifluoromethyl)pyridin-2-amine (S)-4-cyclopropyl-5-(2-morpholino-5a,6,8,9-tetrahydro-5H-pyrimido[5',4':4,5]pyrrolo[2,1-c][1,4]oxazin-4-yl)pyridin-2-amine (S)-4-ethyl-5-(2-morpholino-5a,6,8,9-tetrahydro-5H-pyrimido[5',4':4,5]pyrrolo[2,1-c][1,4]oxazin-4-yl)pyridin-2-amine (S)-5-(2-morpholino-5a,6,8,9-tetrahydro-5H-pyrimido[5',4':4,5]pyrrolo[2,1-c][1,4]oxazin-4-yl)pyrimidin-2-amine (S)-4-methyl-5-(2-morpholino-5a,6,8,9-tetrahydro-5H-pyrimido[5',4':4,5]pyrrolo[2,1-c][1,4]oxazin-4-yl)pyrimidin-2-amine (S)-4-chloro-5-(2-morpholino-5a,6,8,9-tetrahydro-5H-pyrimido[5',4':4,5]pyrrolo[2,1-c][1,4]oxazin-4-yl)pyrimidin-2-amine (S)-2-amino-5-(2-morpholino-5a,6,8,9-tetrahydro-5H-pyrimido[5',4':4,5]pyrrolo[2,1-c][1,4]oxazin-4-yl)isonicotinonitrile (S)-4-(difluoromethyl)-5-(2-morpholino-5a,6,8,9-tetrahydro-5H-pyrimido[5',4':4,5]pyrrolo[2,1-c][1,4]oxazin-4-yl)pyrimidin-2-amine (S)-5-(2-morpholino-5a,6,8,9-tetrahydro-5H-pyrimido[5',4':4,5]pyrrolo[2,1-c][1,4]oxazin-4-yl)-4-(trifluoromethyl)pyrimidin-2-amine (S)-4-cyclopropyl-5-(2-morpholino-5a,6,8,9-tetrahydro-5H-pyrimido[5',4':4,5]pyrrolo[2,1-c][1,4]oxazin-4-yl)pyrimidin-2-amine, —(S)-4-ethyl-5-(2-morpholino-5a,6,8,9-tetrahydro-5H-pyrimido[5',4':4,5]pyrrolo[2,1-c][1,4]oxazin-4-yl)pyrimidin-2-amine (R)-1-methyl-3-(4-(4-morpholino-5a,6,8,9-tetrahydro-5H-pyrimido[5',4':4,5]pyrrolo[2,1-c][1,4]oxazin-2-yl)phenyl)urea (R)-1-methyl-3-(5-(4-morpholino-5a,6,8,9-tetrahydro-5H-pyrimido[5',4':4,5]pyrrolo[2,1-c][1,4]oxazin-2-yl)pyridin-2-yl)urea (R)-1-methyl-3-(5-(4-morpholino-5a,6,8,9-tetrahydro-5H-pyrimido[5',4':4,5]pyrrolo[2,1-c][1,4]oxazin-2-yl)pyrimidin-2-yl)urea methyl (R)-(4-(4-morpholino-5a,6,8,9-tetrahydro-5H-pyrimido[5',4':4,5]pyrrolo[2,1-c][1,4]oxazin-2-yl)phenyl)carbamate methyl (R)-(5-(4-morpholino-5a,6,8,9-tetrahydro-5H-pyrimido[5',4':4,5]pyrrolo[2,1-c][1,4]oxazin-2-yl)pyridin-2-yl)carbamate methyl (R)-(5-(4-morpholino-5a,6,8,9-tetrahydro-5H-pyrimido[5',4':4,5]pyrrolo[2,1-c][1,4]oxazin-2-yl)pyrimidin-2-yl)carbamate (R)-1-(4-(4-(dimethylamino)piperidine-1-carbonyl)phenyl)-3-(4-(4-morpholino-5a,6,8,9-tetrahydro-5H-pyrimido[5',4':4,5]pyrrolo[2,1-c][1,4]oxazin-2-yl)phenyl)urea (R)-1-(4-(4-(dimethylamino)piperidine-1-carbonyl)phenyl)-3-(5-(4-morpholino-5a,6,8,9-tetrahydro-5H-pyrimido[5',4':4,5]pyrrolo[2,1-c][1,4]oxazin-2-yl)pyridin-2-yl)urea (R)-1-(4-(4-(dimethylamino)piperidine-1-carbonyl)phenyl)-3-(5-(4-morpholino-5a,6,8,9-tetrahydro-5H-pyrimido[5',4':4,5]pyrrolo[2,1-c][1,4]oxazin-2-yl)pyrimidin-2-yl)urea (R)-5-(4-morpholino-5a,6,8,9-tetrahydro-5H-pyrimido[5',4':4,5]pyrrolo[2,1-c][1,4]thiazin-2-yl)-4-(trifluoromethyl)pyridin-2-amine (5aR)-2-(6-amino-4-(trifluoromethyl)pyridin-3-yl)-4-morpholino-5a,6,8,9-tetrahydro-5H-pyrimido[5',4':4,5]pyrrolo[2,1-c][1,4]thiazine 7-oxide (R)-2-(6-amino-4-(trifluoromethyl)pyridin-3-yl)-4-morpholino-5a,6,8,9-tetrahydro-5H-pyrimido[5',4':4,5]pyrrolo[2,1-c][1,4]thiazine 7,7-dioxide 5-((5aR)-4-(8-oxa-3-azabicyclo[3.2.1]octan-3-yl)-5a,6,8,9-tetrahydro-5H-pyrimido[5',4':4,5]pyrrolo[2,1-c][1,4]oxazin-2-yl)-4-(trifluoromethyl)pyridin-2-amine (S)-1-methyl-3-(4-(4-morpholino-5a,6,8,9-tetrahydro-5H-pyrimido[5',4':4,5]pyrrolo[2,1-c][1,4]oxazin-2-yl)phenyl)urea (S)-1-methyl-3-(5-(4-morpholino-5a,6,8,9-tetrahydro-5H-pyrimido[5',4':4,5]pyrrolo[2,1-c][1,4]oxazin-2-yl)pyridin-2-yl)urea (S)-1-methyl-3-(5-(4-morpholino-5a,6,8,9-tetrahydro-5H-pyrimido[5',4':4,5]pyrrolo[2,1-c][1,4]oxazin-2-yl)pyrimidin-2-yl)urea methyl (S)-(4-(4-morpholino-5a,6,8,9-tetrahydro-5H-pyrimido[5',4':4,5]pyrrolo[2,1-c][1,4]oxazin-2-yl)phenyl)carbamate methyl (S)-(5-(4-morpholino-5a,6,8,9-tetrahydro-5H-pyrimido[5',4':4,5]pyrrolo[2,1-c][1,4]oxazin-2-yl)pyridin-2-yl)carbamate methyl (S)-(5-(4-morpholino-5a,6,8,9-tetrahydro-5H-pyrimido[5',4':4,5]pyrrolo[2,1-c][1,4]oxazin-2-yl)pyrimidin-2-yl)carbamate (S)-1-(4-(4-(dimethylamino)piperidine-1-carbonyl)phenyl)-3-(4-(4-morpholino-5a,6,8,9-tetrahydro-5H-pyrimido[5',4':4,5]pyrrolo[2,1-c][1,4]oxazin-2-yl)phenyl)urea (S)-1-(4-(4-(dimethylamino)piperidine-1-carbonyl)phenyl)-3-(5-(4-morpholino-5a,6,8,9-tetrahydro-5H-pyrimido[5',4':4,5]pyrrolo[2,1-c][1,4]oxazin-2-yl)pyridin-2-yl)urea (S)-1-(4-(4-(dimethylamino)piperidine-1-carbonyl)phenyl)-3-(5-(4-morpholino-5a,6,8,9-tetrahydro-5H-pyrimido[5',4':4,5]pyrrolo[2,1-c][1,4]oxazin-2-yl)pyrimidin-2-yl)urea (S)-5-(4-morpholino-5a,6,8,9-tetrahydro-5H-pyrimido[5',4':4,5]pyrrolo[2,1-c][1,4]thiazin-2-yl)-4-(trifluoromethyl)pyridin-2-amine (5aS)-2-(6-amino-4-(trifluoromethyl)pyridin-3-yl)-4-morpholino-5a,6,8,9-tetrahydro-5H-pyrimido[5',4':4,5]pyrrolo[2,1-c][1,4]thiazine 7-oxide (S)-2-(6-amino-4-(trifluoromethyl)pyridin-3-yl)-4-morpholino-5a,6,8,9-tetrahydro-5H-pyrimido[5',4':4,5]pyrrolo[2,1-c][1,4]thiazine 7,7-dioxide 5-((5aS)-4-(8-oxa-3-azabicyclo[3.2.1]octan-3-yl)-5a,6,8,9-tetrahydro-5H-pyrimido[5',4':4,5]pyrrolo[2,1-c][1,4]oxazin-2-yl)-4-(trifluoromethyl)pyridin-2-amine.

13. The compound of claim 1 selected from the group consisting of (R)-5-(4-morpholino-5a,6,8,9-tetrahydro-5H-pyrimido[5',4':4,5]pyrrolo[2,1-c][1,4]oxazin-2-yl)-4-(trifluoromethyl)pyridin-2-amine, (S)-5-(4-morpholino-5a,6,8,9-tetrahydro-5H-pyrimido[5',4':4,5]pyrrolo[2,1-c][1,4]oxazin-2-yl)-4-(trifluoromethyl)pyridin-2-amine, (R)-5-(2-morpholino-5a,6,8,9-tetrahydro-5H-pyrimido[5',4':4,5]pyrrolo[2,1-c][1,4]oxazin-4-yl)-4-(trifluoromethyl)pyridin-2-amine, and (S)-5-(2-morpholino-5a,6,8,9-tetrahydro-5H-pyrimido[5',4':4,5]pyrrolo[2,1-c][1,4]oxazin-4-yl)-4-(trifluoromethyl)pyridin-2-amine.

14. The compound of claim 1 selected from the group consisting of (R)-5-(2-morpholino-5a,6,8,9-tetrahydro-5H-pyrimido[5',4':4,5]pyrrolo[2,1-c][1,4]oxazin-4-yl)pyrimidin-2-amine (S)-5-(2-morpholino-5a,6,8,9-tetrahydro-5H-pyrimido[5',4':4,5]pyrrolo[2,1-c][1,4]oxazin-4-yl)pyrimidin-2-amine (R)-5-(4-morpholino-5a,6,8,9-tetrahydro-5H-pyrimido[5',4':4,5]pyrrolo[2,1-c][1,4]oxazin-2-yl)pyrimidin-2-amine (S)-5-(4-morpholino-5a,6,8,9-tetrahydro-5H-pyrimido[5',4':4,5]pyrrolo[2,1-c][1,4]oxazin-2-yl)pyrimidin-2-amine.

15. A pharmaceutical composition comprising a compound of claim 1 and a pharmaceutically acceptable carrier.

16. A compound of claim 1 for use in the treatment of cancer.

* * * * *